US010632208B2

(12) United States Patent
Bhunia et al.

(10) Patent No.: US 10,632,208 B2
(45) Date of Patent: Apr. 28, 2020

(54) PEPTIDE-MEDIATED DRUG DELIVERY ACROSS EPITHELIAL BARRIER

(71) Applicant: Purdue Research Foundation, West Lafayette, IN (US)

(72) Inventors: Arun K. Bhunia, West Lafayette, IN (US); Rishi Drolia, West Lafayette, IN (US); Manalee Samaddar, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/151,484

(22) Filed: Oct. 4, 2018

(65) Prior Publication Data

US 2019/0105401 A1 Apr. 11, 2019

Related U.S. Application Data

(60) Provisional application No. 62/569,020, filed on Oct. 6, 2017.

(51) Int. Cl.

| | |
|---|---|
| ***A61K 47/64*** | (2017.01) |
| ***A61K 31/337*** | (2006.01) |
| ***A61K 38/16*** | (2006.01) |
| ***A61K 9/00*** | (2006.01) |

(52) U.S. Cl.

CPC .............. *A61K 47/64* (2017.08); *A61K 9/006* (2013.01); *A61K 9/0031* (2013.01); *A61K 9/0034* (2013.01); *A61K 31/337* (2013.01); *A61K 38/164* (2013.01)

(58) Field of Classification Search

CPC .... A61K 31/337; A61K 38/164; A61K 47/64; A61K 9/0031; A61K 9/0034; A61K 9/006; B60P 1/26

See application file for complete search history.

(56) References Cited

U.S. PATENT DOCUMENTS

2020/0000876 A1* 1/2020 Bhunia ................ A61K 38/164

FOREIGN PATENT DOCUMENTS

WO WO2012109121 * 8/2012 .............. A61P 31/04

OTHER PUBLICATIONS

Al-Sadi, R., (2014), Interleukin-6 modulation of intestinal epithelial tight junction permeability is mediated by JNK pathway activation of claudin-2 gene, PLoS One 9.

Burkholder, K., Listeria monocytogenes uses Listeria adhesion protein (LAP) to promote bacterial transepithelial translocation, and induces expression of LAP receptor Hsp60, Infect. Immun., 78, 5062-5073.

Chiba, S., (2011), Listerial invasion protein internalin B promotes entry into ileal Peyer's patches in vivo, Microbiol. Immunol., 55, 123-129.

Disson, O., (2008), Conjugated action of two species-specific invasion proteins for fetoplacental listeriosis, Nature 455, 1114-1118.

Freitag, N., (2009), Listeria monocytogenes from saprophyte to intracellular pathogen, Nat. Rev., Microbiol. 7, 623-628.

Jadadeesan, B., (2010) LAP, an alcohol acetaldehyde dehydrogenase enzyme in Listeria, promotes bacterial adhesion to enterocyte-like Caco-2 cells only in pathogenic species, Microbiology, 156, 2782-2795.

Lecuit, M., (1999), A single amino acid in E-cadherin responsible for host specificity towards the human pathogen Listeria monocytogenes, EMBO J., 18, 3956-3963.

Lecuit, M., (2007), Functional genomic studies of the intestinal response to a foodbome enteropathogen in a humanized gnotobiotic mouse model, J. Biol. Chem., 282, 15065-15072.

Lecuit, M., (2001), A transgenic model for listeriosis: role of intemalin in crossing the intestinal barrier, Science 292, 1722-1725.

Ma, T. (2005), Mechanism of TNF-a modulation of Caco-2 intestinal epithelial tight junction barrier: Role of myosin light-chain kinase protein expression, Am. J. Physiol. Gastrointest. Liver Physiol., 288, G422-G430.

Ma, T., (2004), TNF-a induced increase in intestinal epithelial tight junction permeability requires NF-kB activation, Am. J. Physiol. Gastrointes. Liver Physiol., 286, G367-G376.

Marchiando, A., (2011), The epithelial barrier is maintained by in vivo tight junction expansion during pathologic intestinal epithelial shedding, Gastroenterology 140, 1208-1218. e1202.

Meddings, J., (2000), Environmental stress-induced gastrointestinal permeability is mediated by endogenous glucocorticoids in the rat, Gastroenterology 119, 1019-1028.

Nikitas, G., (2011), Transcytosis of Listeria monocytogenes across the intestinal barrier upon specific targeting of goblet cell accessible E-cadherin, J. Exp. Med. 208, 2263-2277.

Wang, L., (2015), Methods to determine intestinal permeability and bacterial translocation during liver disease, J. Immunol. Methods, 421, 44-53.

Zhang, T., (2017), Deciphering the landscape of host barriers to Listeria monocytogenes infection, Proc Nat Acad Sci U S A 114, 6334-6339.

Zolotarevsky, Y., (2002), A membrane-permeant peptide that inhibits MLC kinase restores barrier function in in vitro models of intestinal disease, Gastroenterology 123, 163-172.

Patel, S., (2012), Synthesis, characterization and brain targeting potential of paclitaxel loaded thiamine-PPI nanoconjugates, Journal of drug targeting, 20(10), 841-849.

(Continued)

*Primary Examiner* — Marcela M Cordero Garcia
(74) *Attorney, Agent, or Firm* — Purdue Research Foundation; Liang Zeng Yan

(57) ABSTRACT

This present application relates to a drug delivery method. In particular, the present invention discloses a non-invasive drug delivery method using *Listeria* adhesion protein (LAP) an analogue, or a fragment thereof. Incorporation of those peptides or a fragment thereof, either by a physical mixture of a pharmaceutical formulation or as a covalent construction at a molecular level or nanoscale is within the scope of this disclosure.

20 Claims, 29 Drawing Sheets

Specification includes a Sequence Listing.

(56) References Cited

OTHER PUBLICATIONS

Sakamoto, S., (2017), Ultrasensitive immunoassay for monocrotaline using monoclonal antibody produced by N, N'-carbonyldiimidazole mediated hapten-carrier protein conjugates, Talanta, 168, 67-72.

Ikeno, S., Boost Protein Expression through Co-Expression of LEA-Like Peptide in *Escherichia coli,* PloS One, 2013, 8(12), e82824).

* cited by examiner

SEQUENCE LISTING

<160> NUMBER OF SEQ ID NOS: 14

<210> SEQ ID NO 1
<211> LENGTH: 866
<212> TYPE: PRT

-continued

<213> ORGANISM: Listeria monocytogenes

<400> SEQUENCE: 1

```
Met Ala Ile Lys Glu Asn Ala Ala Gln Glu Val Leu Glu Val Gln Lys
1               5                   10                  15

Val Ile Asp Arg Leu Ala Asp Asn Gly Gln Lys Ala Leu Lys Ala Phe
            20                  25                  30

Glu Ser Tyr Asn Gln Glu Gln Val Asp Asn Ile Val His Ala Met Ala
        35                  40                  45

Leu Ala Gly Leu Asp Gln His Met Pro Leu Ala Lys Leu Ala Val Glu
    50                  55                  60

Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile Asn Glu Asp Val Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Arg Cys Ser Ser Ala Ala Ala Lys
145                 150                 155                 160

Val Val Tyr Asp Ala Ala Ile Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Asp Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240

Asn Asp Ile Ile Leu Ser Lys Ser Phe Asp Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Lys Cys Tyr Phe Val Lys Gly Ala Glu Phe
        275                 280                 285

Lys Lys Leu Glu Ser Tyr Val Ile Asn Pro Glu Lys Gly Thr Leu Asn
    290                 295                 300

Pro Asp Val Val Gly Lys Ser Pro Ala Trp Ile Ala Asn Gln Ala Gly
305                 310                 315                 320

Phe Lys Val Pro Glu Asp Thr Lys Ile Leu Val Ala Glu Ile Lys Gly
                325                 330                 335

Val Gly Asp Lys Tyr Pro Leu Ser His Glu Lys Leu Ser Pro Val Leu
            340                 345                 350

Ala Phe Ile Glu Ala Ala Asn Gln Ala Glu Ala Phe Asp Arg Cys Glu
        355                 360                 365

Glu Met Leu Val Tyr Gly Gly Leu Gly His Ser Ala Val Ile His Ser
    370                 375                 380

Thr Asp Lys Glu Val Gln Lys Ala Phe Gly Ile Arg Met Lys Ala Cys
385                 390                 395                 400
```

-continued

```
Arg Ile Ile Val Asn Ala Pro Ser Ala Gln Gly Gly Ile Gly Asp Ile
                405                 410                 415

Tyr Asn Gly Phe Ile Pro Ser Leu Thr Leu Gly Cys Gly Ser Tyr Gly
            420                 425                 430

Lys Asn Ser Val Ser Gln Asn Val Ser Ala Thr Asn Leu Leu Asn Val
        435                 440                 445

Lys Arg Ile Ala Asp Arg Arg Asn Asn Met Gln Trp Phe Lys Leu Pro
    450                 455                 460

Pro Lys Ile Phe Phe Glu Lys Tyr Ser Thr Gln Tyr Leu Gln Lys Met
465                 470                 475                 480

Glu Gly Val Glu Arg Val Phe Ile Val Thr Asp Pro Gly Met Gly Ser
                485                 490                 495

Phe Lys Tyr Val Asp Val Val Ile Glu His Leu Lys Lys Arg Gly Asn
            500                 505                 510

Asp Val Ala Tyr Gln Val Phe Ala Asp Val Glu Pro Asp Pro Ser Asp
        515                 520                 525

Val Thr Val Tyr Lys Gly Ala Glu Leu Met Lys Asp Phe Lys Pro Asp
    530                 535                 540

Thr Ile Ile Ala Leu Gly Gly Gly Ser Ala Met Asp Ala Ala Lys Gly
545                 550                 555                 560

Met Trp Leu Phe Tyr Glu His Pro Glu Ala Ser Phe Phe Gly Leu Lys
                565                 570                 575

Gln Lys Phe Leu Asp Ile Arg Lys Arg Thr Phe Lys Tyr Pro Lys Leu
            580                 585                 590

Gly Gly Lys Ala Lys Phe Val Ala Ile Pro Thr Thr Ser Gly Thr Gly
        595                 600                 605

Ser Glu Val Thr Pro Phe Ala Val Ile Thr Asp Lys Glu Asn Asn Ile
    610                 615                 620

Lys Tyr Pro Leu Ala Asp Tyr Glu Leu Thr Pro Asp Val Ala Ile Val
625                 630                 635                 640

Asp Ala Gln Tyr Val Thr Thr Val Pro Ala His Ile Thr Ala Asp Thr
                645                 650                 655

Gly Met Asp Val Leu Thr His Ala Ile Glu Ser Tyr Val Ser Val Met
            660                 665                 670

Ala Ser Asp Tyr Thr Arg Gly Leu Ser Ile Arg Ala Ile Glu Leu Val
        675                 680                 685

Phe Glu Asn Leu Arg Glu Ser Val Leu Thr Gly Asp Pro Asp Ala Arg
    690                 695                 700

Glu Lys Met His Asn Ala Ser Ala Leu Ala Gly Met Ala Phe Ala Asn
705                 710                 715                 720

Ala Phe Leu Gly Ile Asn His Ser Leu Ala His Lys Ile Gly Pro Glu
                725                 730                 735

Phe His Ile Pro His Gly Arg Ala Asn Ala Ile Leu Met Pro His Val
            740                 745                 750

Ile Arg Tyr Asn Ala Leu Lys Pro Lys Lys His Ala Leu Phe Pro Arg
        755                 760                 765

Tyr Glu Ser Phe Arg Ala Asp Glu Asp Tyr Ala Arg Ile Ser Arg Ile
    770                 775                 780

Ile Gly Phe Pro Ala Ala Thr Thr Glu Glu Gly Val Lys Ser Leu Val
785                 790                 795                 800

Asp Glu Ile Ile Lys Leu Gly Lys Asp Val Gly Ile Asp Met Ser Leu
                805                 810                 815

Lys Gly Gln Asn Val Ala Lys Lys Asp Leu Asp Ala Val Val Asp Thr
```

```
            820                 825                 830

Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865


<210> SEQ ID NO 2
<211> LENGTH: 188
<212> TYPE: PRT
<213> ORGANISM: Artificial Sequence
<220> FEATURE:
<223> OTHER INFORMATION: Listeria Adhesion Protein N2 domain

<400> SEQUENCE: 2

Gly Asn Val Pro Ala Tyr Ile Asp Lys Thr Ala Lys Ile Lys Arg Ser
1               5                   10                  15

Val Asn Asp Ile Ile Leu Ser Lys Ser Phe Asp Gln Gly Met Ile Cys
            20                  25                  30

Ala Ser Glu Gln Ala Val Ile Val Asp Lys Glu Val Ala Lys Glu Val
        35                  40                  45

Lys Ala Glu Met Glu Ala Asn Lys Cys Tyr Phe Val Lys Gly Ala Glu
    50                  55                  60

Phe Lys Lys Leu Glu Ser Tyr Val Ile Asn Pro Glu Lys Gly Thr Leu
65                  70                  75                  80

Asn Pro Asp Val Val Gly Lys Ser Pro Ala Trp Ile Ala Asn Gln Ala
                85                  90                  95

Gly Phe Lys Val Pro Glu Asp Thr Lys Ile Leu Val Ala Glu Ile Lys
            100                 105                 110

Gly Val Gly Asp Lys Tyr Pro Leu Ser His Glu Lys Leu Ser Pro Val
        115                 120                 125

Leu Ala Phe Ile Glu Ala Ala Asn Gln Ala Glu Ala Phe Asp Arg Cys
    130                 135                 140

Glu Glu Met Leu Val Tyr Gly Gly Leu Gly His Ser Ala Val Ile His
145                 150                 155                 160

Ser Thr Asp Lys Glu Val Gln Lys Ala Phe Gly Ile Arg Met Lys Ala
                165                 170                 175

Cys Arg Ile Ile Val Asn Ala Pro Ser Ala Gln Gly
            180                 185


<210> SEQ ID NO 3
<211> LENGTH: 200
<212> TYPE: PRT
<213> ORGANISM: Artificial Sequence
<220> FEATURE:
<223> OTHER INFORMATION: Listeria Adhesion Protein N2 domain with
      histidine tag

<400> SEQUENCE: 3

His His His His His His Gly Asn Val Pro Ala Tyr Ile Asp Lys Thr
1               5                   10                  15

Ala Lys Ile Lys Arg Ser Val Asn Asp Ile Ile Leu Ser Lys Ser Phe
            20                  25                  30

Asp Gln Gly Met Ile Cys Ala Ser Glu Gln Ala Val Ile Val Asp Lys
        35                  40                  45

Glu Val Ala Lys Glu Val Lys Ala Glu Met Glu Ala Asn Lys Cys Tyr
    50                  55                  60
```

Phe Val Lys Gly Ala Glu Phe Lys Lys Leu Glu Ser Tyr Val Ile Asn
65 70 75 80

Pro Glu Lys Gly Thr Leu Asn Pro Asp Val Val Gly Lys Ser Pro Ala
85 90 95

Trp Ile Ala Asn Gln Ala Gly Phe Lys Val Pro Glu Asp Thr Lys Ile
100 105 110

Leu Val Ala Glu Ile Lys Gly Val Gly Asp Lys Tyr Pro Leu Ser His
115 120 125

Glu Lys Leu Ser Pro Val Leu Ala Phe Ile Glu Ala Ala Asn Gln Ala
130 135 140

Glu Ala Phe Asp Arg Cys Glu Glu Met Leu Val Tyr Gly Gly Leu Gly
145 150 155 160

His Ser Ala Val Ile His Ser Thr Asp Lys Glu Val Gln Lys Ala Phe
165 170 175

Gly Ile Arg Met Lys Ala Cys Arg Ile Ile Val Asn Ala Pro Ser Ala
180 185 190

Gln Gly His His His His His His
195 200

<210> SEQ ID NO 4
<211> LENGTH: 223
<212> TYPE: PRT
<213> ORGANISM: Artificial Sequence
<220> FEATURE:
<223> OTHER INFORMATION: Listeria Adhesion Protein N1 domain

<400> SEQUENCE: 4

Met Ala Ile Lys Glu Asn Ala Ala Gln Glu Val Leu Glu Val Gln Lys
1 5 10 15

Val Ile Asp Arg Leu Ala Asp Asn Gly Gln Lys Ala Leu Lys Ala Phe
20 25 30

Glu Ser Tyr Asn Gln Glu Gln Val Asp Asn Ile Val His Ala Met Ala
35 40 45

Leu Ala Gly Leu Asp Gln His Met Pro Leu Ala Lys Leu Ala Val Glu
50 55 60

Glu Thr Gly Arg Gly Leu Tyr Glu Asp Lys Cys Ile Lys Asn Ile Phe
65 70 75 80

Ala Thr Glu Tyr Ile Trp Asn Asn Ile Lys Asn Asn Lys Thr Val Gly
85 90 95

Val Ile Asn Glu Asp Val Gln Thr Gly Val Ile Glu Ile Ala Glu Pro
100 105 110

Val Gly Val Val Ala Gly Val Thr Pro Val Thr Asn Pro Thr Ser Thr
115 120 125

Thr Leu Phe Lys Ala Ile Ile Ala Ile Lys Thr Arg Asn Pro Ile Ile
130 135 140

Phe Ala Phe His Pro Ser Ala Gln Arg Cys Ser Ser Ala Ala Ala Lys
145 150 155 160

Val Val Tyr Asp Ala Ala Ile Ala Ala Gly Ala Pro Glu His Cys Ile
165 170 175

Gln Trp Val Glu Lys Pro Ser Leu Glu Ala Thr Lys Gln Leu Met Asn
180 185 190

His Asp Lys Val Ala Leu Val Leu Ala Thr Gly Gly Ala Gly Met Val
195 200 205

Lys Ser Ala Tyr Ser Thr Gly Lys Pro Ala Leu Gly Val Gly Pro
210 215 220

-continued

```
<210> SEQ ID NO 5
<211> LENGTH: 238
<212> TYPE: PRT
<213> ORGANISM: Artificial Sequence
<220> FEATURE:
<223> OTHER INFORMATION: Listeria Adhesion Protein C1 domain

<400> SEQUENCE: 5

Gly Gly Ile Gly Asp Ile Tyr Asn Gly Phe Ile Pro Ser Leu Thr Leu
1               5                   10                  15

Gly Cys Gly Ser Tyr Gly Lys Asn Ser Val Ser Gln Asn Val Ser Ala
            20                  25                  30

Thr Asn Leu Leu Asn Val Lys Arg Ile Ala Asp Arg Arg Asn Asn Met
        35                  40                  45

Gln Trp Phe Lys Leu Pro Pro Lys Ile Phe Phe Glu Lys Tyr Ser Thr
    50                  55                  60

Gln Tyr Leu Gln Lys Met Glu Gly Val Glu Arg Val Phe Ile Val Thr
65                  70                  75                  80

Asp Pro Gly Met Gly Ser Phe Lys Tyr Val Asp Val Val Ile Glu His
                85                  90                  95

Leu Lys Lys Arg Gly Asn Asp Val Ala Tyr Gln Val Phe Ala Asp Val
            100                 105                 110

Glu Pro Asp Pro Ser Asp Val Thr Val Tyr Lys Gly Ala Glu Leu Met
        115                 120                 125

Lys Asp Phe Lys Pro Asp Thr Ile Ile Ala Leu Gly Gly Gly Ser Ala
    130                 135                 140

Met Asp Ala Ala Lys Gly Met Trp Leu Phe Tyr Glu His Pro Glu Ala
145                 150                 155                 160

Ser Phe Phe Gly Leu Lys Gln Lys Phe Leu Asp Ile Arg Lys Arg Thr
                165                 170                 175

Phe Lys Tyr Pro Lys Leu Gly Gly Lys Ala Lys Phe Val Ala Ile Pro
            180                 185                 190

Thr Thr Ser Gly Thr Gly Ser Glu Val Thr Pro Phe Ala Val Ile Thr
        195                 200                 205

Asp Lys Glu Asn Asn Ile Lys Tyr Pro Leu Ala Asp Tyr Glu Leu Thr
    210                 215                 220

Pro Asp Val Ala Ile Val Asp Ala Gln Tyr Val Thr Thr Val
225                 230                 235


<210> SEQ ID NO 6
<211> LENGTH: 218
<212> TYPE: PRT
<213> ORGANISM: Artificial Sequence
<220> FEATURE:
<223> OTHER INFORMATION: Listeria Adhesion Protein C2 domain

<400> SEQUENCE: 6

Pro Ala His Ile Thr Ala Asp Thr Gly Met Asp Val Leu Thr His Ala
1               5                   10                  15

Ile Glu Ser Tyr Val Ser Val Met Ala Ser Asp Tyr Thr Arg Gly Leu
            20                  25                  30

Ser Ile Arg Ala Ile Glu Leu Val Phe Glu Asn Leu Arg Glu Ser Val
        35                  40                  45

Leu Thr Gly Asp Pro Asp Ala Arg Glu Lys Met His Asn Ala Ser Ala
    50                  55                  60

Leu Ala Gly Met Ala Phe Ala Asn Ala Phe Leu Gly Ile Asn His Ser
```

-continued

```
65                  70                  75                  80

Leu Ala His Lys Ile Gly Pro Glu Phe His Ile Pro His Gly Arg Ala
                85                  90                  95

Asn Ala Ile Leu Met Pro His Val Ile Arg Tyr Asn Ala Leu Lys Pro
            100                 105                 110

Lys Lys His Ala Leu Phe Pro Arg Tyr Glu Ser Phe Arg Ala Asp Glu
        115                 120                 125

Asp Tyr Ala Arg Ile Ser Arg Ile Ile Gly Phe Pro Ala Ala Thr Thr
    130                 135                 140

Glu Glu Gly Val Lys Ser Leu Val Asp Glu Ile Ile Lys Leu Gly Lys
145                 150                 155                 160

Asp Val Gly Ile Asp Met Ser Leu Lys Gly Gln Asn Val Ala Lys Lys
                165                 170                 175

Asp Leu Asp Ala Val Val Asp Thr Leu Ala Asp Arg Ala Phe Met Asp
            180                 185                 190

Gln Cys Thr Thr Ala Asn Pro Lys Gln Pro Leu Val Ser Glu Leu Lys
        195                 200                 205

Glu Ile Tyr Leu Glu Ala Tyr Lys Gly Val
    210                 215


<210> SEQ ID NO 7
<211> LENGTH: 235
<212> TYPE: PRT
<213> ORGANISM: Artificial Sequence
<220> FEATURE:
<223> OTHER INFORMATION: Listeria Adhesion Protein N1 domain with
      histidine tag

<400> SEQUENCE: 7

His His His His His His Met Ala Ile Lys Glu Asn Ala Ala Gln Glu
1               5                   10                  15

Val Leu Glu Val Gln Lys Val Ile Asp Arg Leu Ala Asp Asn Gly Gln
            20                  25                  30

Lys Ala Leu Lys Ala Phe Glu Ser Tyr Asn Gln Glu Gln Val Asp Asn
        35                  40                  45

Ile Val His Ala Met Ala Leu Ala Gly Leu Asp Gln His Met Pro Leu
    50                  55                  60

Ala Lys Leu Ala Val Glu Glu Thr Gly Arg Gly Leu Tyr Glu Asp Lys
65                  70                  75                  80

Cys Ile Lys Asn Ile Phe Ala Thr Glu Tyr Ile Trp Asn Asn Ile Lys
                85                  90                  95

Asn Asn Lys Thr Val Gly Val Ile Asn Glu Asp Val Gln Thr Gly Val
            100                 105                 110

Ile Glu Ile Ala Glu Pro Val Gly Val Val Ala Gly Val Thr Pro Val
        115                 120                 125

Thr Asn Pro Thr Ser Thr Thr Leu Phe Lys Ala Ile Ile Ala Ile Lys
    130                 135                 140

Thr Arg Asn Pro Ile Ile Phe Ala Phe His Pro Ser Ala Gln Arg Cys
145                 150                 155                 160

Ser Ser Ala Ala Ala Lys Val Val Tyr Asp Ala Ala Ile Ala Ala Gly
                165                 170                 175

Ala Pro Glu His Cys Ile Gln Trp Val Glu Lys Pro Ser Leu Glu Ala
            180                 185                 190

Thr Lys Gln Leu Met Asn His Asp Lys Val Ala Leu Val Leu Ala Thr
        195                 200                 205
```

-continued

```
Gly Gly Ala Gly Met Val Lys Ser Ala Tyr Ser Thr Gly Lys Pro Ala
    210                 215                 220

Leu Gly Val Gly Pro His His His His His His
225                 230                 235


<210> SEQ ID NO 8
<211> LENGTH: 250
<212> TYPE: PRT
<213> ORGANISM: Artificial Sequence
<220> FEATURE:
<223> OTHER INFORMATION: Listeria Adhesion Protein C1 domain with
      histidine tag

<400> SEQUENCE: 8

His His His His His His Gly Gly Ile Gly Asp Ile Tyr Asn Gly Phe
1               5                   10                  15

Ile Pro Ser Leu Thr Leu Gly Cys Gly Ser Tyr Gly Lys Asn Ser Val
            20                  25                  30

Ser Gln Asn Val Ser Ala Thr Asn Leu Leu Asn Val Lys Arg Ile Ala
        35                  40                  45

Asp Arg Arg Asn Asn Met Gln Trp Phe Lys Leu Pro Pro Lys Ile Phe
    50                  55                  60

Phe Glu Lys Tyr Ser Thr Gln Tyr Leu Gln Lys Met Glu Gly Val Glu
65                  70                  75                  80

Arg Val Phe Ile Val Thr Asp Pro Gly Met Gly Ser Phe Lys Tyr Val
                85                  90                  95

Asp Val Val Ile Glu His Leu Lys Lys Arg Gly Asn Asp Val Ala Tyr
            100                 105                 110

Gln Val Phe Ala Asp Val Glu Pro Asp Pro Ser Asp Val Thr Val Tyr
        115                 120                 125

Lys Gly Ala Glu Leu Met Lys Asp Phe Lys Pro Asp Thr Ile Ile Ala
    130                 135                 140

Leu Gly Gly Gly Ser Ala Met Asp Ala Ala Lys Gly Met Trp Leu Phe
145                 150                 155                 160

Tyr Glu His Pro Glu Ala Ser Phe Phe Gly Leu Lys Gln Lys Phe Leu
                165                 170                 175

Asp Ile Arg Lys Arg Thr Phe Lys Tyr Pro Lys Leu Gly Gly Lys Ala
            180                 185                 190

Lys Phe Val Ala Ile Pro Thr Thr Ser Gly Thr Gly Ser Glu Val Thr
        195                 200                 205

Pro Phe Ala Val Ile Thr Asp Lys Glu Asn Asn Ile Lys Tyr Pro Leu
    210                 215                 220

Ala Asp Tyr Glu Leu Thr Pro Asp Val Ala Ile Val Asp Ala Gln Tyr
225                 230                 235                 240

Val Thr Thr Val His His His His His His
                245                 250


<210> SEQ ID NO 9
<211> LENGTH: 230
<212> TYPE: PRT
<213> ORGANISM: Artificial Sequence
<220> FEATURE:
<223> OTHER INFORMATION: Listeria Adhesion Protein C2 domain with
      histidine tag

<400> SEQUENCE: 9

His His His His His His Pro Ala His Ile Thr Ala Asp Thr Gly Met
1               5                   10                  15
```

-continued

```
Asp Val Leu Thr His Ala Ile Glu Ser Tyr Val Ser Val Met Ala Ser
            20                  25                  30

Asp Tyr Thr Arg Gly Leu Ser Ile Arg Ala Ile Glu Leu Val Phe Glu
        35                  40                  45

Asn Leu Arg Glu Ser Val Leu Thr Gly Asp Pro Asp Ala Arg Glu Lys
    50                  55                  60

Met His Asn Ala Ser Ala Leu Ala Gly Met Ala Phe Ala Asn Ala Phe
65                  70                  75                  80

Leu Gly Ile Asn His Ser Leu Ala His Lys Ile Gly Pro Glu Phe His
                85                  90                  95

Ile Pro His Gly Arg Ala Asn Ala Ile Leu Met Pro His Val Ile Arg
            100                 105                 110

Tyr Asn Ala Leu Lys Pro Lys Lys His Ala Leu Phe Pro Arg Tyr Glu
        115                 120                 125

Ser Phe Arg Ala Asp Glu Asp Tyr Ala Arg Ile Ser Arg Ile Ile Gly
    130                 135                 140

Phe Pro Ala Ala Thr Thr Glu Glu Gly Val Lys Ser Leu Val Asp Glu
145                 150                 155                 160

Ile Ile Lys Leu Gly Lys Asp Val Gly Ile Asp Met Ser Leu Lys Gly
                165                 170                 175

Gln Asn Val Ala Lys Lys Asp Leu Asp Ala Val Val Asp Thr Leu Ala
            180                 185                 190

Asp Arg Ala Phe Met Asp Gln Cys Thr Thr Ala Asn Pro Lys Gln Pro
        195                 200                 205

Leu Val Ser Glu Leu Lys Glu Ile Tyr Leu Glu Ala Tyr Lys Gly Val
    210                 215                 220

His His His His His His
225                 230
```

<210> SEQ ID NO 10
<211> LENGTH: 878
<212> TYPE: PRT
<213> ORGANISM: Artificial Sequence
<220> FEATURE:
<223> OTHER INFORMATION: Listeria Adhesion Protein (LAP) with histidine tag

<400> SEQUENCE: 10

```
His His His His His His Met Ala Ile Lys Glu Asn Ala Ala Gln Glu
1               5                   10                  15

Val Leu Glu Val Gln Lys Val Ile Asp Arg Leu Ala Asp Asn Gly Gln
            20                  25                  30

Lys Ala Leu Lys Ala Phe Glu Ser Tyr Asn Gln Glu Gln Val Asp Asn
        35                  40                  45

Ile Val His Ala Met Ala Leu Ala Gly Leu Asp Gln His Met Pro Leu
    50                  55                  60

Ala Lys Leu Ala Val Glu Glu Thr Gly Arg Gly Leu Tyr Glu Asp Lys
65                  70                  75                  80

Cys Ile Lys Asn Ile Phe Ala Thr Glu Tyr Ile Trp Asn Asn Ile Lys
                85                  90                  95

Asn Asn Lys Thr Val Gly Val Ile Asn Glu Asp Val Gln Thr Gly Val
            100                 105                 110

Ile Glu Ile Ala Glu Pro Val Gly Val Val Ala Gly Val Thr Pro Val
        115                 120                 125

Thr Asn Pro Thr Ser Thr Thr Leu Phe Lys Ala Ile Ile Ala Ile Lys
    130                 135                 140
```

-continued

```
Thr Arg Asn Pro Ile Ile Phe Ala Phe His Pro Ser Ala Gln Arg Cys
145                 150                 155                 160

Ser Ser Ala Ala Ala Lys Val Val Tyr Asp Ala Ala Ile Ala Ala Gly
                165                 170                 175

Ala Pro Glu His Cys Ile Gln Trp Val Glu Lys Pro Ser Leu Glu Ala
            180                 185                 190

Thr Lys Gln Leu Met Asn His Asp Lys Val Ala Leu Val Leu Ala Thr
        195                 200                 205

Gly Gly Ala Gly Met Val Lys Ser Ala Tyr Ser Thr Gly Lys Pro Ala
    210                 215                 220

Leu Gly Val Gly Pro Gly Asn Val Pro Ala Tyr Ile Asp Lys Thr Ala
225                 230                 235                 240

Lys Ile Lys Arg Ser Val Asn Asp Ile Ile Leu Ser Lys Ser Phe Asp
                245                 250                 255

Gln Gly Met Ile Cys Ala Ser Glu Gln Ala Val Ile Val Asp Lys Glu
            260                 265                 270

Val Ala Lys Glu Val Lys Ala Glu Met Glu Ala Asn Lys Cys Tyr Phe
        275                 280                 285

Val Lys Gly Ala Glu Phe Lys Lys Leu Glu Ser Tyr Val Ile Asn Pro
    290                 295                 300

Glu Lys Gly Thr Leu Asn Pro Asp Val Val Gly Lys Ser Pro Ala Trp
305                 310                 315                 320

Ile Ala Asn Gln Ala Gly Phe Lys Val Pro Glu Asp Thr Lys Ile Leu
                325                 330                 335

Val Ala Glu Ile Lys Gly Val Gly Asp Lys Tyr Pro Leu Ser His Glu
            340                 345                 350

Lys Leu Ser Pro Val Leu Ala Phe Ile Glu Ala Ala Asn Gln Ala Glu
        355                 360                 365

Ala Phe Asp Arg Cys Glu Glu Met Leu Val Tyr Gly Gly Leu Gly His
    370                 375                 380

Ser Ala Val Ile His Ser Thr Asp Lys Glu Val Gln Lys Ala Phe Gly
385                 390                 395                 400

Ile Arg Met Lys Ala Cys Arg Ile Ile Val Asn Ala Pro Ser Ala Gln
                405                 410                 415

Gly Gly Ile Gly Asp Ile Tyr Asn Gly Phe Ile Pro Ser Leu Thr Leu
            420                 425                 430

Gly Cys Gly Ser Tyr Gly Lys Asn Ser Val Ser Gln Asn Val Ser Ala
        435                 440                 445

Thr Asn Leu Leu Asn Val Lys Arg Ile Ala Asp Arg Arg Asn Asn Met
    450                 455                 460

Gln Trp Phe Lys Leu Pro Pro Lys Ile Phe Phe Glu Lys Tyr Ser Thr
465                 470                 475                 480

Gln Tyr Leu Gln Lys Met Glu Gly Val Glu Arg Val Phe Ile Val Thr
                485                 490                 495

Asp Pro Gly Met Gly Ser Phe Lys Tyr Val Asp Val Val Ile Glu His
            500                 505                 510

Leu Lys Lys Arg Gly Asn Asp Val Ala Tyr Gln Val Phe Ala Asp Val
        515                 520                 525

Glu Pro Asp Pro Ser Asp Val Thr Val Tyr Lys Gly Ala Glu Leu Met
    530                 535                 540

Lys Asp Phe Lys Pro Asp Thr Ile Ile Ala Leu Gly Gly Gly Ser Ala
545                 550                 555                 560
```

-continued

```
Met Asp Ala Ala Lys Gly Met Trp Leu Phe Tyr Glu His Pro Glu Ala
                565                 570                 575

Ser Phe Phe Gly Leu Lys Gln Lys Phe Leu Asp Ile Arg Lys Arg Thr
            580                 585                 590

Phe Lys Tyr Pro Lys Leu Gly Gly Lys Ala Lys Phe Val Ala Ile Pro
        595                 600                 605

Thr Thr Ser Gly Thr Gly Ser Glu Val Thr Pro Phe Ala Val Ile Thr
    610                 615                 620

Asp Lys Glu Asn Asn Ile Lys Tyr Pro Leu Ala Asp Tyr Glu Leu Thr
625                 630                 635                 640

Pro Asp Val Ala Ile Val Asp Ala Gln Tyr Val Thr Thr Val Pro Ala
                645                 650                 655

His Ile Thr Ala Asp Thr Gly Met Asp Val Leu Thr His Ala Ile Glu
            660                 665                 670

Ser Tyr Val Ser Val Met Ala Ser Asp Tyr Thr Arg Gly Leu Ser Ile
        675                 680                 685

Arg Ala Ile Glu Leu Val Phe Glu Asn Leu Arg Glu Ser Val Leu Thr
    690                 695                 700

Gly Asp Pro Asp Ala Arg Glu Lys Met His Asn Ala Ser Ala Leu Ala
705                 710                 715                 720

Gly Met Ala Phe Ala Asn Ala Phe Leu Gly Ile Asn His Ser Leu Ala
                725                 730                 735

His Lys Ile Gly Pro Glu Phe His Ile Pro His Gly Arg Ala Asn Ala
            740                 745                 750

Ile Leu Met Pro His Val Ile Arg Tyr Asn Ala Leu Lys Pro Lys Lys
        755                 760                 765

His Ala Leu Phe Pro Arg Tyr Glu Ser Phe Arg Ala Asp Glu Asp Tyr
    770                 775                 780

Ala Arg Ile Ser Arg Ile Ile Gly Phe Pro Ala Ala Thr Thr Glu Glu
785                 790                 795                 800

Gly Val Lys Ser Leu Val Asp Glu Ile Ile Lys Leu Gly Lys Asp Val
                805                 810                 815

Gly Ile Asp Met Ser Leu Lys Gly Gln Asn Val Ala Lys Lys Asp Leu
            820                 825                 830

Asp Ala Val Val Asp Thr Leu Ala Asp Arg Ala Phe Met Asp Gln Cys
        835                 840                 845

Thr Thr Ala Asn Pro Lys Gln Pro Leu Val Ser Glu Leu Lys Glu Ile
    850                 855                 860

Tyr Leu Glu Ala Tyr Lys Gly Val His His His His His His
865                 870                 875


<210> SEQ ID NO 11
<211> LENGTH: 866
<212> TYPE: PRT
<213> ORGANISM: Listeria ivanovii

<400> SEQUENCE: 11

Met Ala Ile Lys Glu Asn Ala Ala Gln Glu Val Leu Glu Val Gln Lys
1               5                   10                  15

Val Ile Asp Arg Leu Ala Asp Asn Gly Gln Lys Ala Leu Lys Ala Phe
            20                  25                  30

Glu Asn Tyr Asp Gln Glu Gln Val Asp Asn Ile Val His Ala Met Ala
        35                  40                  45

Leu Ala Gly Leu Asp Gln His Met Pro Leu Ala Lys Leu Ala Val Glu
    50                  55                  60
```

-continued

```
Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile Asn Glu Asp Val Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Gly Cys Ser Ser Ala Ala Ala Lys
145                 150                 155                 160

Val Val Tyr Asp Ala Ala Ile Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Glu Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240

Ser Asp Ile Ile Leu Ser Lys Ser Phe Asp Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Lys Cys Tyr Phe Val Lys Gly Ala Glu Phe
        275                 280                 285

Lys Lys Leu Glu Ser Tyr Val Ile Asn Pro Glu Lys Gly Thr Leu Asn
    290                 295                 300

Pro Asp Val Val Gly Lys Ser Pro Ala Trp Ile Ala Asn Gln Ala Gly
305                 310                 315                 320

Phe Lys Ile Pro Glu Asp Thr Lys Ile Leu Val Ala Glu Ile Lys Gly
                325                 330                 335

Val Gly Asp Lys Tyr Pro Leu Ser His Glu Lys Leu Ser Pro Val Leu
            340                 345                 350

Ala Phe Ile Glu Ala Ala Asn Gln Thr Glu Ala Phe Asp Arg Cys Glu
        355                 360                 365

Glu Met Leu Val Tyr Gly Gly Leu Gly His Ser Ala Val Ile His Ser
    370                 375                 380

Thr Asp Lys Glu Val Gln Lys Ala Phe Gly Ile Arg Met Lys Ala Cys
385                 390                 395                 400

Arg Ile Ile Val Asn Ala Pro Ser Ala Gln Gly Gly Ile Gly Asp Ile
                405                 410                 415

Tyr Asn Gly Phe Ile Pro Ser Leu Thr Leu Gly Cys Gly Ser Tyr Gly
            420                 425                 430

Lys Asn Ser Val Ser Gln Asn Val Ser Ala Thr Asn Leu Leu Asn Val
        435                 440                 445

Lys Arg Ile Ala Asp Arg Arg Asn Asn Met Gln Trp Phe Lys Leu Pro
    450                 455                 460

Pro Lys Ile Phe Phe Glu Lys Tyr Ser Thr Gln Tyr Leu Gln Lys Met
465                 470                 475                 480
```

-continued

```
Glu Gly Val Glu Arg Val Phe Ile Val Thr Asp Pro Gly Met Val Gln
                485                 490                 495

Phe Lys Tyr Val Asp Val Val Ile Glu His Leu Lys Lys Arg Gly Asn
            500                 505                 510

Asp Val Ser Tyr Gln Val Phe Ala Asp Val Glu Pro Asp Pro Ser Asp
        515                 520                 525

Val Thr Val Tyr Lys Gly Ala Glu Leu Met Lys Asp Phe Lys Pro Asp
    530                 535                 540

Thr Ile Ile Ala Leu Gly Gly Gly Ser Ala Met Asp Ala Ala Lys Gly
545                 550                 555                 560

Met Trp Leu Phe Tyr Glu His Pro Glu Ala Ser Phe Phe Gly Leu Lys
                565                 570                 575

Gln Lys Phe Leu Asp Ile Arg Lys Arg Thr Phe Lys Tyr Pro Lys Leu
            580                 585                 590

Gly Gly Lys Ala Lys Phe Val Ala Ile Pro Thr Thr Ser Gly Thr Gly
        595                 600                 605

Ser Glu Val Thr Pro Phe Ala Val Ile Thr Asp Lys Glu Asn Asn Ile
    610                 615                 620

Lys Tyr Pro Leu Ala Asp Tyr Glu Leu Thr Pro Asp Val Ala Ile Val
625                 630                 635                 640

Asp Ala Gln Tyr Val Thr Thr Val Pro Ala His Ile Thr Ala Asp Thr
                645                 650                 655

Gly Met Asp Val Leu Thr His Ala Ile Glu Ser Tyr Val Ser Val Met
            660                 665                 670

Ala Ser Asp Tyr Thr Arg Gly Val Ser Ile Arg Ala Ile Glu Leu Val
        675                 680                 685

Phe Glu Asn Leu Arg Asp Ser Val Leu Lys Gly Asp Pro Asp Ala Arg
    690                 695                 700

Glu Lys Met His Asn Ala Ser Ala Leu Ala Gly Met Ala Phe Ala Asn
705                 710                 715                 720

Ala Phe Leu Gly Ile Asn His Ser Leu Ala His Lys Ile Gly Pro Glu
                725                 730                 735

Phe His Ile Pro His Gly Arg Ala Asn Ala Ile Leu Met Pro His Val
            740                 745                 750

Ile Arg Tyr Asn Ala Leu Lys Pro Arg Lys His Ala Leu Phe Pro Arg
        755                 760                 765

Tyr Glu Ser Phe Arg Ala Asp Glu Asp Tyr Ala Arg Ile Ser Arg Ile
    770                 775                 780

Ile Gly Phe Pro Ala Ala Thr Thr Glu Glu Gly Val Lys Ser Leu Val
785                 790                 795                 800

Asp Glu Ile Ile Lys Leu Gly Lys Asp Val Gly Ile Asp Met Ser Leu
                805                 810                 815

Lys Gly Gln Asn Val Ala Lys Lys Asp Leu Asp Ala Val Val Asp Thr
            820                 825                 830

Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865

<210> SEQ ID NO 12
<211> LENGTH: 866
<212> TYPE: PRT
```

-continued

<213> ORGANISM: Listeria seeligeri

<400> SEQUENCE: 12

```
Met Ala Ile Lys Glu Asn Ala Ala Gln Glu Val Leu Glu Val Gln Lys
1               5                   10                  15

Val Ile Asp Arg Leu Ala Asp Asn Gly Gln Lys Ala Leu Lys Ala Phe
            20                  25                  30

Glu Asn Tyr Asp Gln Glu Gln Val Asp Asn Ile Val His Ala Met Ala
        35                  40                  45

Leu Ala Gly Leu Asp Gln His Met Pro Leu Ala Lys Leu Ala Val Glu
    50                  55                  60

Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile Asn Glu Asp Val Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Gly Cys Ser Ser Ala Ala Ala Lys
145                 150                 155                 160

Val Val Tyr Asp Ala Ala Ile Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Glu Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240

Asn Asp Ile Ile Leu Ser Lys Ser Phe Asp Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Asn Cys Tyr Phe Val Lys Gly Ala Glu Phe
        275                 280                 285

Lys Lys Leu Glu Ser Tyr Val Ile Asn Pro Glu Lys Gly Thr Leu Asn
    290                 295                 300

Pro Asp Val Val Gly Lys Ser Pro Ala Trp Ile Ala Asn Gln Ala Gly
305                 310                 315                 320

Phe Lys Val Pro Glu Asp Thr Lys Ile Leu Val Ala Glu Ile Lys Gly
                325                 330                 335

Val Gly Asp Lys Tyr Pro Leu Ser His Glu Lys Leu Ser Pro Val Leu
            340                 345                 350

Ala Phe Ile Glu Ala Ala Asn Gln Ala Glu Ala Phe Asp Arg Cys Glu
        355                 360                 365

Glu Met Leu Val Tyr Gly Gly Leu Gly His Ser Ala Val Ile His Ser
    370                 375                 380

Thr Asp Lys Glu Val Gln Lys Ala Phe Gly Ile Arg Met Lys Ala Cys
385                 390                 395                 400
```

-continued

```
Arg Ile Ile Val Asn Ala Pro Ser Ala Gln Gly Gly Ile Gly Asp Ile
                405                 410                 415

Tyr Asn Gly Phe Ile Pro Ser Leu Thr Leu Gly Cys Gly Ser Tyr Gly
            420                 425                 430

Lys Asn Ser Val Ser Gln Asn Val Ser Ala Thr Asn Leu Leu Asn Val
        435                 440                 445

Lys Arg Ile Ala Asp Arg Arg Asn Asn Met Gln Trp Phe Lys Leu Pro
    450                 455                 460

Pro Lys Ile Phe Phe Glu Lys Tyr Ser Thr Gln Tyr Leu Gln Lys Met
465                 470                 475                 480

Glu Gly Val Glu Arg Val Phe Ile Val Thr Asp Pro Gly Met Val Gln
                485                 490                 495

Phe Lys Tyr Val Asp Val Val Ile Glu His Leu Lys Lys Arg Gly Asn
            500                 505                 510

Asp Val Ser Tyr Gln Val Phe Ala Asp Val Glu Pro Asp Pro Ser Asp
        515                 520                 525

Val Thr Val Tyr Lys Gly Ala Glu Leu Met Lys Asp Phe Lys Pro Asp
    530                 535                 540

Thr Ile Ile Ala Leu Gly Gly Gly Ser Ala Met Asp Ala Ala Lys Gly
545                 550                 555                 560

Met Trp Leu Phe Tyr Glu His Pro Glu Ala Ser Phe Phe Gly Leu Lys
                565                 570                 575

Gln Lys Phe Leu Asp Ile Arg Lys Arg Thr Phe Lys Tyr Pro Lys Leu
            580                 585                 590

Gly Gly Lys Ala Lys Phe Val Ala Ile Pro Thr Thr Ser Gly Thr Gly
        595                 600                 605

Ser Glu Val Thr Pro Phe Ala Val Ile Thr Asp Lys Glu Asn Asn Ile
    610                 615                 620

Lys Tyr Pro Leu Ala Asp Tyr Glu Leu Thr Pro Asp Val Ala Ile Val
625                 630                 635                 640

Asp Ala Gln Tyr Val Thr Thr Val Pro Ala His Ile Thr Ala Asp Thr
                645                 650                 655

Gly Met Asp Val Leu Thr His Ala Ile Glu Ser Tyr Val Ser Val Met
            660                 665                 670

Ala Gly Asp Tyr Thr Arg Gly Leu Ser Ile Arg Ala Ile Glu Leu Val
        675                 680                 685

Phe Glu Asn Leu Arg Asp Ser Val Leu Lys Gly Asp Pro Asp Ala Arg
    690                 695                 700

Glu Lys Met His Asn Ala Ser Ala Leu Ala Gly Met Ala Phe Ala Asn
705                 710                 715                 720

Ala Phe Leu Gly Ile Asn His Ser Leu Ala His Lys Ile Gly Pro Glu
                725                 730                 735

Phe His Ile Pro His Gly Arg Ala Asn Ala Ile Leu Met Pro His Val
            740                 745                 750

Ile Arg Tyr Asn Ala Leu Lys Pro Lys Lys His Ala Leu Phe Pro Arg
        755                 760                 765

Tyr Glu Ser Phe Arg Ala Asp Glu Asp Tyr Ala Arg Ile Ser Arg Ile
    770                 775                 780

Ile Gly Phe Pro Ala Ala Thr Thr Glu Glu Gly Val Lys Ser Leu Val
785                 790                 795                 800

Asp Glu Ile Ile Lys Leu Gly Lys Asp Val Gly Ile Asp Met Ser Leu
                805                 810                 815

Lys Gly Gln Asn Val Asp Lys Lys Asp Leu Asp Ala Val Val Asp Thr
```

-continued

```
            820                 825                 830

Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865


<210> SEQ ID NO 13
<211> LENGTH: 866
<212> TYPE: PRT
<213> ORGANISM: Listeria welshimeri

<400> SEQUENCE: 13

Met Ala Ile Lys Glu Asn Ala Ala Gln Glu Val Leu Glu Val Gln Lys
1               5                   10                  15

Val Ile Asn Arg Leu Ala Asp Asn Gly Gln Gln Ala Leu Lys Ala Phe
            20                  25                  30

Glu Asn Tyr Asp Gln Glu Gln Val Asp Asn Ile Val His Ala Met Ala
        35                  40                  45

Leu Ala Gly Leu Asp Gln His Met Pro Leu Ala Lys Leu Ala Val Glu
    50                  55                  60

Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile His Glu Asp Val Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Arg Cys Ser Ala Ala Ala Ala Lys
145                 150                 155                 160

Val Val Tyr Asp Ala Ala Val Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Asp Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240

Asn Asp Ile Ile Leu Ser Lys Ser Phe Gly Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Lys Cys Tyr Phe Val Lys Gly Ala Glu Phe
        275                 280                 285

Lys Lys Leu Glu Ser Tyr Val Ile Asn Pro Glu Lys Gly Thr Leu Asn
    290                 295                 300

Pro Asp Val Val Gly Lys Ser Pro Ala Trp Ile Ala Asn Gln Ala Gly
305                 310                 315                 320
```

-continued

```
Phe Lys Val Pro Glu Asp Thr Lys Ile Leu Val Ala Glu Ile Lys Gly
                325                 330                 335

Val Gly Asp Lys Tyr Pro Leu Ser His Glu Lys Leu Ser Pro Val Leu
            340                 345                 350

Ala Phe Ile Glu Ala Ala Asn Gln Ala Glu Ala Phe Asp Arg Cys Glu
        355                 360                 365

Glu Met Leu Val Tyr Gly Gly Leu Gly His Ser Ala Val Ile His Ser
    370                 375                 380

Thr Asp Lys Glu Val Gln Lys Ala Phe Gly Ile Arg Met Lys Ala Cys
385                 390                 395                 400

Arg Ile Ile Val Asn Ala Pro Ser Ala Gln Ser Gly Ile Gly Asp Ile
                405                 410                 415

Tyr Asn Gly Phe Ile Pro Ser Leu Thr Leu Gly Cys Gly Ser Tyr Gly
            420                 425                 430

Lys Asn Ser Val Ser Gln Asn Val Ser Ala Thr Asn Leu Leu Asn Val
        435                 440                 445

Lys Arg Ile Ala Asp Arg Arg Asn Asn Met Gln Trp Phe Lys Leu Pro
    450                 455                 460

Pro Lys Ile Phe Phe Glu Lys Tyr Ser Thr Gln Tyr Leu Gln Lys Met
465                 470                 475                 480

Glu Gly Val Glu Arg Val Phe Ile Val Thr Asp Pro Gly Met Val Gln
                485                 490                 495

Phe Lys Tyr Val Asp Val Val Ile Glu His Leu Lys Lys Arg Gly Asn
            500                 505                 510

Asp Val Ala Tyr Gln Val Phe Ala Asp Val Glu Pro Asp Pro Ser Asp
        515                 520                 525

Val Thr Val Tyr Lys Gly Ala Glu Leu Met Lys Asp Phe Lys Pro Asp
    530                 535                 540

Thr Ile Ile Ala Leu Gly Gly Gly Ser Ala Met Asp Ala Ala Lys Gly
545                 550                 555                 560

Met Trp Leu Phe Tyr Glu His Pro Glu Ala Ser Phe Phe Gly Leu Lys
                565                 570                 575

Gln Lys Phe Leu Asp Ile Arg Lys Arg Thr Phe Lys Tyr Pro Lys Leu
            580                 585                 590

Gly Gly Lys Ala Lys Phe Val Ala Ile Pro Thr Thr Ser Gly Thr Gly
        595                 600                 605

Ser Glu Val Thr Pro Phe Ala Val Ile Thr Asp Lys Glu Asn Asn Ile
    610                 615                 620

Lys Tyr Pro Leu Ala Asp Tyr Glu Leu Thr Pro Asp Val Ala Ile Val
625                 630                 635                 640

Asp Ala Gln Tyr Val Thr Thr Val Pro Ala His Ile Thr Ala Asp Thr
                645                 650                 655

Gly Met Asp Val Leu Thr His Ala Ile Glu Ser Tyr Val Ser Val Met
            660                 665                 670

Ala Ser Asp Tyr Thr Arg Gly Leu Ser Ile Arg Ala Ile Glu Leu Val
        675                 680                 685

Phe Glu Asn Leu Arg Glu Ser Val Leu Thr Gly Asp Pro Asp Ala Arg
    690                 695                 700

Glu Lys Met His Asn Ala Ser Ala Leu Ala Gly Met Ala Phe Ala Asn
705                 710                 715                 720

Ala Phe Leu Gly Ile Asn His Ser Leu Ala His Lys Ile Gly Pro Glu
                725                 730                 735

Phe His Ile Pro His Gly Arg Ala Asn Ala Ile Leu Met Pro His Val
```

```
            740                 745                 750

Ile Arg Tyr Asn Ala Leu Lys Pro Lys Lys His Ala Leu Phe Pro Arg
        755                 760                 765

Tyr Glu Ser Phe Arg Ala Asp Glu Asp Tyr Ala Arg Ile Ser Arg Ile
    770                 775                 780

Ile Gly Leu Pro Ala Ala Thr Thr Glu Glu Gly Val Lys Ser Leu Val
785                 790                 795                 800

Asp Ala Ile Ile Lys Leu Gly Lys Asp Val Gly Ile Asp Met Ser Leu
                805                 810                 815

Lys Gly Gln Asn Val Ala Lys Lys Asp Leu Asp Ala Val Val Asp Thr
            820                 825                 830

Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865


<210> SEQ ID NO 14
<211> LENGTH: 866
<212> TYPE: PRT
<213> ORGANISM: Listeria innocua

<400> SEQUENCE: 14

Met Ala Ile Lys Glu Asn Ala Ala Gln Glu Val Leu Glu Val Gln Lys
1               5                   10                  15

Val Ile Asp Arg Leu Ala Asp Asn Gly Gln Lys Ala Leu Lys Ala Phe
            20                  25                  30

Glu Ser Tyr Asn Gln Glu Gln Val Asp Asn Ile Val His Ala Met Ala
        35                  40                  45

Leu Ala Gly Leu Asp Gln His Met Pro Leu Ala Lys Leu Ala Val Glu
    50                  55                  60

Glu Thr Gly Arg Gly Leu Tyr Glu Asp Lys Cys Ile Lys Asn Ile Phe
65                  70                  75                  80

Ala Thr Glu Tyr Ile Trp Asn Asn Ile Lys Asn Asn Lys Thr Val Gly
                85                  90                  95

Val Ile Asn Glu Asp Thr Gln Thr Gly Val Ile Glu Ile Ala Glu Pro
            100                 105                 110

Val Gly Val Val Ala Gly Val Thr Pro Val Thr Asn Pro Thr Ser Thr
        115                 120                 125

Thr Leu Phe Lys Ala Ile Ile Ala Ile Lys Thr Arg Asn Pro Ile Ile
    130                 135                 140

Phe Ala Phe His Pro Ser Ala Gln Arg Cys Ser Ser Glu Ala Ala Lys
145                 150                 155                 160

Val Val Tyr Asp Ala Ala Val Ala Ala Gly Ala Pro Glu His Cys Ile
                165                 170                 175

Gln Trp Val Glu Lys Pro Ser Leu Glu Ala Thr Lys Gln Leu Met Asn
            180                 185                 190

His Asp Lys Val Ala Leu Val Leu Ala Thr Gly Gly Ala Gly Met Val
        195                 200                 205

Lys Ser Ala Tyr Ser Thr Gly Lys Pro Ala Leu Gly Val Gly Pro Gly
    210                 215                 220

Asn Val Pro Ala Tyr Ile Asp Lys Thr Ala Lys Ile Lys Arg Ser Val
225                 230                 235                 240
```

-continued

```
Asn Asp Ile Ile Leu Ser Lys Ser Phe Asp Gln Gly Met Ile Cys Ala
                245                 250                 255

Ser Glu Gln Ala Val Ile Val Asp Lys Glu Val Ala Lys Glu Val Lys
            260                 265                 270

Ala Glu Met Glu Ala Asn Lys Cys Tyr Phe Val Lys Gly Ala Glu Phe
        275                 280                 285

Lys Lys Leu Glu Ser Tyr Val Ile Asn Pro Glu Lys Gly Thr Leu Asn
    290                 295                 300

Pro Asp Val Val Gly Lys Ser Pro Ala Trp Ile Ala Asn Gln Ala Gly
305                 310                 315                 320

Phe Lys Val Pro Glu Asp Thr Lys Ile Leu Val Ala Glu Ile Lys Gly
                325                 330                 335

Val Gly Asp Lys Tyr Pro Leu Ser His Glu Lys Leu Ser Pro Val Leu
            340                 345                 350

Ala Phe Ile Glu Ala Ala Thr Gln Ala Glu Ala Phe Asp Arg Cys Glu
        355                 360                 365

Glu Met Leu Val Tyr Gly Gly Leu Gly His Ser Ala Val Ile His Ser
    370                 375                 380

Thr Asp Lys Glu Val Gln Lys Ala Phe Gly Ile Arg Met Lys Ala Cys
385                 390                 395                 400

Arg Ile Ile Val Asn Ala Pro Ser Ala Gln Gly Gly Ile Gly Asp Ile
                405                 410                 415

Tyr Asn Gly Phe Ile Pro Ser Leu Thr Leu Gly Cys Gly Ser Tyr Gly
            420                 425                 430

Lys Asn Ser Val Ser Gln Asn Val Ser Ala Thr Asn Leu Leu Asn Val
        435                 440                 445

Lys Arg Ile Ala Asp Arg Arg Asn Asn Met Gln Trp Phe Lys Leu Pro
    450                 455                 460

Pro Lys Ile Phe Phe Glu Lys Tyr Ser Thr Gln Tyr Leu Gln Lys Met
465                 470                 475                 480

Glu Gly Val Glu Arg Val Phe Ile Val Thr Asp Pro Gly Met Val Gln
                485                 490                 495

Phe Lys Tyr Val Asp Val Val Ile Glu His Leu Lys Lys Arg Gly Asn
            500                 505                 510

Asp Val Ala Tyr Gln Val Phe Ala Asp Val Glu Pro Asp Pro Ser Asp
        515                 520                 525

Val Thr Val Tyr Lys Gly Ala Glu Leu Met Lys Asp Phe Lys Pro Asp
    530                 535                 540

Thr Ile Ile Ala Leu Gly Gly Gly Ser Ala Met Asp Ala Ala Lys Gly
545                 550                 555                 560

Met Trp Leu Phe Tyr Glu His Pro Glu Ala Ser Phe Phe Gly Leu Lys
                565                 570                 575

Gln Lys Phe Leu Asp Ile Arg Lys Arg Thr Phe Lys Tyr Pro Lys Leu
            580                 585                 590

Gly Gly Lys Ala Lys Phe Val Ala Ile Pro Thr Thr Ser Gly Thr Gly
        595                 600                 605

Ser Glu Val Thr Pro Phe Ala Val Ile Thr Asp Lys Glu Asn Asn Ile
    610                 615                 620

Lys Tyr Pro Leu Ala Asp Tyr Glu Leu Thr Pro Asp Val Ala Ile Val
625                 630                 635                 640

Asp Ala Gln Tyr Val Thr Thr Val Pro Ala His Ile Thr Ala Asp Thr
                645                 650                 655

Gly Met Asp Val Leu Thr His Ala Ile Glu Ser Tyr Val Ser Val Met
```

-continued

```
            660                 665                 670

Ala Ser Asp Tyr Thr Arg Gly Leu Ser Ile Arg Ala Ile Glu Leu Val
        675                 680                 685

Phe Glu Asn Leu Arg Glu Ser Val Leu Thr Gly Asp Pro Asp Ala Arg
    690                 695                 700

Glu Lys Met His Asn Ala Ser Ala Leu Ala Gly Met Ala Phe Ala Asn
705                 710                 715                 720

Ala Phe Leu Gly Ile Asn His Ser Leu Ala His Lys Ile Gly Pro Glu
                725                 730                 735

Phe His Ile Pro His Gly Arg Ala Asn Ala Ile Leu Met Pro His Val
            740                 745                 750

Ile Arg Tyr Asn Ala Leu Lys Pro Lys Lys His Ala Leu Phe Pro Arg
        755                 760                 765

Tyr Glu Ser Phe Arg Ala Asp Glu Asp Tyr Ala Arg Ile Ser Arg Ile
    770                 775                 780

Ile Gly Phe Pro Ala Ala Thr Thr Glu Glu Gly Val Lys Ser Leu Val
785                 790                 795                 800

Asp Glu Ile Ile Lys Leu Gly Lys Asp Val Gly Ile Asp Met Ser Leu
                805                 810                 815

Lys Gly Gln Asn Val Ala Lys Lys Asp Leu Asp Ala Val Val Asp Thr
            820                 825                 830

Leu Ala Asp Arg Ala Phe Met Asp Gln Cys Thr Thr Ala Asn Pro Lys
        835                 840                 845

Gln Pro Leu Val Ser Glu Leu Lys Glu Ile Tyr Leu Glu Ala Tyr Lys
    850                 855                 860

Gly Val
865
```

PEPTIDE-MEDIATED DRUG DELIVERY ACROSS EPITHELIAL BARRIER

CROSS-REFERENCE TO RELATED APPLICATIONS

The present U.S. patent application relates to and claims the priority benefit of U.S. Provisional Patent Application Ser. No. 62/569,020, filed Oct. 6, 2017, the content of which is hereby incorporated by reference in its entirety.

STATEMENT OF SEQUENCE LISTING

A computer-readable form (CRF) of the Sequence Listing is submitted concurrently with this application. The file, generated on Oct. 1, 2018, is entitled Sequence_Listing_67963-02_ST25_txt. Applicant states that the content of the computer-readable form is the same and the information recorded in computer readable form is identical to the written sequence listing.

TECHNICAL FIELD

The present invention generally relates to a method for enhanced delivery of a drug across epithelial barriers using a peptide derived from Listeria Adhesion Protein (LAP). In particular, the present invention discloses a non-invasive drug delivery method using Listeria adhesion protein (LAP) or a fragment of ten or more continuous amino acid residues thereof. Incorporation of those peptides or a fragment thereof, either as a physical mixture of a pharmaceutical formulation or as a covalent construction at a molecular level or nanoscale is within the scope of this disclosure.

BACKGROUND AND BRIEF SUMMARY

This section introduces aspects that may help facilitate a better understanding of the disclosure. Accordingly, these statements are to be read in this light and are not to be understood as admissions about what is or is not prior art.

One of the most common and attractive practices of drug delivery is by oral route. However, overcoming the gastrointestinal epithelial barrier is the major challenge for efficient delivery of drugs, especially for those of peptides, proteins or other therapeutics of biological origins. There are unmet needs in providing patient-friendly, high-compliant, oral dosing therapeutics of biological origins. We have discovered that the para cellular route may be exploited to provide a solution to those unmet needs by using a bacterial-origin peptide for enhanced delivery of drugs through the epithelial barrier to reach the underlying lamina propria and submucosal compartment.

In some illustrative embodiments, the present invention generally relates to a method for enhanced delivery of a drug across epithelial barriers using a peptide derived from Listeria adhesion protein (LAP). In particular, the present invention discloses a non-invasive drug delivery method using Listeria adhesion protein (LAP), an analogue of 90% or higher identity, or a fragment of ten or more continuous amino acid residues thereof.

In some other embodiments, this present invention relates to a method for enhanced delivery of a drug across epithelial barriers by incorporation of those polypeptides disclosed herein, either as a physical mixture of a pharmaceutical formulation or as a covalent construction at molecular level to the drug molecule to be delivered by a selective chemical modification or by a recombinant technology.

BRIEF DESCRIPTION OF THE DRAWINGS

A better understanding of the present invention will be obtained upon reference to the following description in conjunction with the accompanying drawings.

FIGS. 1A-1F show that eight-ten week-old female A/J mice were orally challenged with $1\times10^8$ CFU of WT, $lap^-$ or ΔinlA *L. monocytogenes* bacteria. The plots show the total CFU obtained from the liver (FIG. 1A), spleen (FIG. 1B), MLN (FIG. 1C), ileal mucus layer (FIG. 1D), ileal epithelial cell (intracellular+extracellular) (FIG. 1E), and ileal lamina propria (intracellular+extracellular) (FIG. 1F) of mice (nr=4-12) at 24 and 48 h pi from three independent experiments. Significantly reduced *L. monocytogenes* counts (CFU) were recovered in the liver, spleen, MLN and lamina propria of mice challenged with the $lap^-$ strain. Bar and brackets represent the mean±SEM, respectively, for the data points in each group. Dashed horizontal lines indicate the limit of detection for each organ/tissue. **, P<0.0001; , P<0.01; *, P<0.5; ns, no significance.

FIG. 1G shows confocal immunofluorescence microscopy of ileal tissue sections immunostained for ZO-1 (red), *Listeria* (green, arrows) and DAPI (blue; nucleus) from WT, $lap^-$ or ΔinlA-challenged mice 48 h pi, Bars, 10 μm. The panels below each image show enlargements of the boxed areas. Bars, 1 μm. *L. monocytogenes* was detected in the lamina propria (white arrows) or the epithelial cells (yellow arrows) of the WT and ΔinlA-challenged mice but in the lumen (yellow arrows) of the $lap^-$-challenged mice.

FIG. 1H shows graph representing % of villus positive±SD for *Listeria* in lamina propria, n=50 villi from 2-3 mice.

FIG. 2A shows analysis of the paracellular permeability of 4-kDa FITC-dextran (FD4) through intestinal epithelium of A/J mice, administered orally 4-5 h before sacrifice, in serum at 24 h and 48 h pi. Mice infected with the WT, or ΔinlA strain exhibited significantly increased FD4 flux in comparison with $lap^-$ infected or uninfected mice. Data represent mean±SEM of n=5-7 mice per treatment from three independent experiments. **, P<0.01; *, P<0.5; ns.

FIG. 2B shows analysis of the paracellular permeability of 4-kDa FITC-dextran (FD4) through intestinal epithelium of A/J mice, administered orally 4-5 h before sacrifice, in urine at 24 h and 48 h pi. Mice infected with the WT, or ΔinlA strain exhibited significantly increased FD4 flux in comparison with $lap^-$ infected or uninfected mice. Data represent mean±SEM of n=5-7 mice per treatment from three independent experiments. **, P<0.01; *, P<0.5; ns.

FIGS. 2C-2F show two representative confocal immunofluorescence microscopy images of 5 μm thick, ileal tissue sections immunostained for ZO-1 (red), *Listeria* (green, arrows) and DAPI (blue; nucleus) from WT (FIGS. 2C, 2D) or ΔinlA (FIGS. 2E, 2F)-challenged mice 48 h pi. Bars, 1 μm. *L. monocytogenes* (arrows, green) was co-localized (yellow in merged images) with the tight junction protein ZO-1 (red) in WT (FIG. 2C) or ΔinlA (FIG. 2E)-challenged mice. *L. monocytogenes* (arrows, yellow in merged images) was also observed exiting the epithelial cell and in the lamina propria in WT (FIG. 2D, arrows) or observed exiting the epithelial cell in ΔinlA (FIG. 2F, arrows)-challenged mice. Separated channels are shown individually to the left (FIGS. 2C-2E) or right (FIGS. 2D, 2F) of the merged images. The X-Z and Y-Z cross-sections were produced by orthogonal reconstructions from z-stack scanning. Pictures are representative of five different fields from two mice. LP, Lamina Propria.

FIGS. 2G-2H show analysis of translocation of *L. monocytogenes* WT and isogenic strains; $lap^-$, $lap^-lap^+$, ΔinlA, ΔinlA $inlA^+$ or $lap^-$ stains with exogenously added recombinant LAP ($lap^-$+LAP: 1 μg/ml, 2 μg/mL) and WT (10403s), and isogenic mutant strains, ΔinlB and Δhly, and *L. innocua* (FIG. 2G) or flux of paracellular marker FD4 in *L. monocytogenes* WT and isogenic strains; $lap^-$ or ΔinlA (FIG. 2H) infected at a MOI of 50 through polarized Caco-2 cell monolayers grown on Transwell filter-inserts. Data represent mean±SEM from three independent experiments, n=6. ***, P<0.001; ns, no significance.

FIGS. 2I-2J show effect of recombinant purified LAP on the Transwell filter-insert grown Caco-2 transepithelial electrical resistance (TEER) after pre-treatment of increasing concentrations of LAP (1-1000 ng/mL) added to the apical compartment or human TNF-α (10 ng/mL) for 48 h (FIG. 2I). Time-course effect of LAP (1 μg/mL) or TNF-α (10 ng/mL) on Caco-2 paracellular permeability, where the effect of LAP on the apical (AP)-to-basolateral (BL) flux of paracellular marker FD4 permeability coefficient ($cm^2$/sec) was measured over a 72-h period (FIG. 2J). Data in (FIGS. 2I-2J) represent mean±SEM from three independent experiments, n=6. *, P<0.001; , P<0.01; *, P<0.5; ns, no significance.

FIGS. 3A-3B depict the results of ELISA showing the quantitative measurement of human TNF-α (FIG. 3A) and IL-6 (FIG. 3B) in Caco-2 cell supernatants, and TNF-α (FIG. 3C) and IL-6 (FIG. 3D) in ileal tissues of mice from uninfected (control) or infected with WT, $lap^-$, and ΔinlA at 48 h pi. *L. innocua* (nonpathogen) and the recombinant LAP (1 μg/mL) purified from *Escherichia coli* BL21 (DE3) strain Clear Coli, in which two of the secondary acyl chains of the normally hexa-acylated LPS have been deleted, thus eliminating a key determinant of endotoxicity were used with Caco-2 cells only (FIGS. 3A, 3B). Mice infected with the $lap^-$ strain exhibited significantly decreased protein levels of TNF-α and IL-6 in Caco-2 cells and mouse ileal mucosa. The data from FIGS. 3A and 3B represent mean±SEM, n=4-6 for each treatment; FIGS. 3C and 3D represent the mean±SEM from n=3-4 mice for each treatment. **, P<0.0001; *, P<0.001; **, P<0.01; *, P<0.5; ns, not significant.

FIGS. 3E-3H show analysis of TNF-α and IL-6 mRNA levels in the ileal mucosa of mice. Total RNA was analyzed for TNF-α at 24 h (FIG. 3E) and 48 h pi (FIG. 3F) or for IL-6 at 24 h (FIG. 3G) and 48 h pi (FIG. 3H). Mice infected with the $lap^-$ strain exhibited significantly decreased mRNA levels of TNF-α and IL-6 in the ileal mucosa. The data represent the mean±SEM from n=3-4 mice for each treatment performed in duplicate and normalized to gapdh levels, with the average for untreated samples set at 1. *, P<0.001; , P<0.01; *, P<0.5; ns, not significant.

FIGS. 3I-3K show histological score of ileal tissue sections at 24 h (FIG. 3I), and 48 h (FIG. 3J) and representative H&E stained picto-micrographs (FIG. 3K) of 24 and 48 h pi (bars, 100 μm) from control mice or mice orally gavaged with $1\times10^8$ CFU of *L. monocytogenes* WT, $lap^-$ or ΔinlA strains. The ilea of mice challenged with the WT strain and ΔinlA strain showed an increased number of goblet cells in the villous epithelium, with numerous neutrophils infiltrating the base of the villous lamina propria and surrounding Peyer's patches (FIG. 3K).

FIGS. 4A-4B show immunoblot analysis of *Listeria*-induced NF-κB activation by monitoring p65 (FIG. 4A) and P-p65 (FIG. 4B) expression in the nuclear extracts of Caco-2 cells infected (MOI; 50, 30 min) with *L. monocytogenes* WT, ΔinlA, $lap^-$, and *L. innocua*. TBP (TATA-binding protein), uninfected cells, and TNF-α (10 ng/mL) were used as loading, baseline, and positive control, respectively. Densitometry report of immunoblots in A, B are graphed below each blot. Caco-2 cells infected with the $lap^-$ strain exhibited significantly decreased p65 and P-p65 levels. Immunoblots are representative of three independent experiments and densitometry report represent the mean±SEM of three independent experiments. ***, P<0.001; , P<0.01.

FIGS. 4C-4D show dose-dependent effect of purified LAP treatment: immunoblots showing dose dependent increased levels of IKK-α (FIG. 4C) in the cytoplasmic extracts and of p65 and P-p65 (FIG. 4D) in the nuclear extracts of Caco-2 cells treated with LAP (1-1000 ng/mL) for 30 min. TNF-α (10 ng/mL) was used as a positive control, 3-actin (FIG. 4B) and TBP (FIG. 4C) were used as loading controls in respective cellular fractions. Densitometry report of immunoblots in FIGS. 4B and 4C are graphed below each blot. Immunoblots are representative of three independent experiments and densitometry report represent the mean±SEM of three independent experiments. ***, P<0.001.

FIGS. 4E and 4F show immunoblots showing time dependent kinetics of IκBα decrease (FIG. 4E) and P-IκBα increase (FIG. 4F) in the cytoplasmic fraction and p65 increase (FIG. 4E) and P-p65 increase (FIG. 4F) in the nuclear extracts of Caco-2 cells treated with LAP (1000 ng/mL) or with TNF-α (10 ng/mL) for 0-120 min. β-actin (FIG. 4E) and TBP (FIG. 4F) were used as loading controls in respective cellular fractions. Immunoblots (FIGS. 4E-4F) are representative of two independent experiments.

FIG. 4G shows confocal-immunofluorescence microscopy of Caco-2 cells treated with LAP (1 μg/mL) or human TNF-α (10 ng/mL) for 30 min and immunoprobed with mAbs against p65 (green). Nuclei were counterstained with DAPI (blue). Arrows indicate the nuclear localization of p65 in LAP and TNF-α treated cells. Scale bars, 20 μm. The image is representative of five different fields from two independent experiments.

FIGS. 4H-4I show confocal immunofluorescence microscopy of the ileal tissue sections immunostained for p65 (FIG. 4H, green) and P-p65 (FIG. 4I, green) from unchallenged (control) mice or mice challenged with WT, $lap^-$, and ΔinlA (see FIG. 1G). NF-κB(p65) and P-p65 are labeled in green and the nuclei were counterstained with DAPI (blue). Arrows indicate the nuclear localization of p65 and P-p65 in ileal mucosa of WT and ΔinlA challenged mice. Images are representative of, n=10-15 villi from two-three mice per treatment. Scale bars, 10 μm.

FIG. 4J shows results from FIGS. 4H-4I expressed as mean±SEM p65 and P-p65 nuclear positive intestinal epithelial cells (IEC) per villus from 10-15 villi from two to three mice per treatment. ***, P<0.001.

FIGS. 4K-4L show decreased translocation of *L. monocytogenes* WT, and ΔinlA strains at MOI of 50 through polarized Caco-2 cell monolayers grown on Transwell filter inserts following pretreatment with BAY 11-7085 (10 μM, 30 min) (FIG. 4K) and of *L. monocytogenes* WT, $lap^-lap^+$, ΔinlA, and ΔinlA $inlA^+$ strains following pretreatment with PDTC (100 μM, 30 min) (FIG. 4L). The data represent the mean±SEM of three independent experiments, n=6. *, P<0.001, , P<0.01.

FIGS. 5A and 5B depict immunoblot analysis showing decreased IKK-β levels in cytosolic extract (top) and decreased p65 levels in the nuclear extracts (bottom) of Caco-2 cells with hsp60 knocked-down (hsp60::shRNA) infected with *L. monocytogenes* WT or $lap^-$ strain (MOI; 50, 30 min) (FIG. 5A) or treated with purified LAP (1 μg/mL) (B) relative to *L. monocytogenes* WT infected (A) or LAP-treated (FIG. 5B) vector control shRNA (control) cells. β-actin (top, FIGS. 5A and 5B) and TBP (bottom, FIGS. 5A and 5B) were used as loading controls in respective cellular fractions. Uninfected cells (control) served as baseline controls and treatment with human TNF-α (10 ng/mL) for 30 min (FIG. 5B) was used as a positive control. Densitometry reports are graphed on the right of each blot represent the mean±SEM of three independent experiments (FIGS. 5A and 5B). Immunoblots are representative of three independent experiments. *, P<0.001; , P<0.01; *, P<0.5.

FIG. 5C shows confocal immunofluorescence microscopic analysis showing the nuclear localization of p65 in vector-control shRNA (control shRNA) Caco-2 cells and cytoplasmic localization of p65 in hsp60 knocked-down (hsp60::shRNA) Caco-2 cells treated with LAP (1 μg/mL) or TNF-α (10 ng/mL) for 30 min. Cells were immunoprobed with mAbs against NF-κB (green) or Hsp60 (red). Nuclei were counterstained with DAPI (blue). Arrows indicate the nuclear localization of p65. The data represent five different fields from two independent experiments. Scale bars, 5 μm.

FIG. 5D depicts immunoblot analysis showing decreased IKK-β levels in cytosolic extract (top) and decreased p65 levels in the nuclear extracts (bottom) of Caco-2 cells incubated with anti-Hsp60 mAb (1 μg/ml, 1 h) to block surface Hsp60 prior to treatment with LAP (1 μg/ml, 30 min). β-actin (top) and TBP (bottom) were used as loading controls in respective cellular fractions. Uninfected cells served as baseline controls. Densitometry reports are graphed on the right of the blot and represent the mean±SEM of three independent experiments. Immunoblots are representative of three independent experiments. ***, P<0.001.

FIGS. 5E and 5F show immunoblots showing the interaction of Hsp60 with IKK-β in LAP (1 μg/ml, 30 min)—treated Caco-2 cells. IKK-β (FIG. 5E) or Hsp60 (FIG. 5F) were immunoprecipitated with respective antibodies from Caco-2 cell lysates (500 μg total proteins for each) and immunoprobed with anti-Hsp60 (FIG. 5E) or anti-IKKβ (FIG. 5F) mAb. Arrows indicate co-precipitated IKK-β and Hsp60, respectively in the LAP-treated cells. The 10% input lane represents 50 μg of Caco-2 lysate not subjected to immunoprecipitation, was used as a positive control. No Ab lane represents immunoprecipitation reactions without addition of antibody, was used as a negative control. Rabbit serum (IgG lane) (FIG. 5E) or normal mouse IgG (IgG lane) (FIG. 5F) was used as an isotype control antibody immunoprecipitation reactions. Background observed in the lanes with serum from rabbit used as an isotype control (FIG. 5E) is due to non-specific reaction. Immunoblots are representative of 3 independent experiments.

FIGS. 6A-6B are the immunoblot showing time-dependent increased levels of MLCK in the whole-cell lysate of Caco-2 cells treated with purified LAP (1 μg/mL) for 0-360 min p.i (FIG. 6A). Immunoblot showing time-dependent increased levels of MLCK and P-MLC in whole-cell Caco-2 cell lysates following *L. monocytogenes* infection (MOI, 50), 0-120 min p.i (FIG. 6B). Right panels are showing densitometry data which represent mean±SEM of three independent immunoblot experiments. *, P<0.001; , P<0.01. Immunoblots are representative of three independent experiments.

FIG. 6C depicts immunoblots showing decreased protein expression levels of occludin and claudin-1 in the detergent-insoluble (membrane) fraction of Caco-2 cells infected with the WT or ΔinlA (MOI; 50, 45 min) strain and decreased E-cadherin levels in Caco-2 cells infected with the WT, but unchanged levels with $lap^-$ strain (MOI; 50, 45 min) relative to uninfected (control) cells (top, left). Increased protein levels of MLCK and P-MLC in whole-cell lysate of Caco-2 cells infected with WT or ΔinlA strain, but unchanged levels with lap-strain (MOI; 50, 45 min) relative to uninfected (control) cells (bottom, left). Restoration of occludin, claudin-1 and E-cadherin protein levels in the detergent-insoluble fraction of Caco-2 cells pre-treated with MLCK inhibitor, PIK (150 μM, 30 min maintained during infection) or with NF-κβ inhibitor, BAY (10 μM, 30 min) prior to infection with the WT strain (MOI; 50, 45 min) (top, right). Decreased levels of MLCK and P-MLC in whole cell lysate of Caco-2 cells pre-treated with MLCK inhibitor PIK (as above) and unchanged levels of MLCK and P-MLC pre-treated with NF-κβ inhibitor, BAY (as above) prior to infection with WT strain, relative to uninfected (control) cells (bottom, right). Immunoblots are representative of two independent experiments. Densitometry reports are graphed below each blot which represent mean±SEM of two independent immunoblot experiments. ***, P<0.001; *, P<0.5; ns, no significance.

FIG. 6D-6E show decreased translocation of the *L. monocytogenes* WT and ΔinlA strains pretreated with MLCK inhibitor, PIK (150 μM, 30 min pre-treatment and maintained during 2-h infection) (FIG. 6D) and of *L. monocytogenes* WT, $lap^-lap^+$, ΔinlA, and ΔinlA $inlA^+$ strains, pretreated with MLCK inhibitor, ML-9 (20 μM, 30 min) (FIG. 6E) through Caco-2 cell monolayers on Transwell filter-inserts infected at a MOI of 50. The data represent the mean±SEM of three independent experiments, n=6. ***, P<0.001: *, P<0.5; ns, no significance.

FIGS. 6F-6G depict immunoblot analysis showing decreased levels of occludin, claudin-1 and E-cadherin, in the detergent-insoluble (membrane) fraction (FIG. 6F) and increased levels of MLCK and P-MLC whole-cell lysates (FIG. 6G) in purified ileal intestinal epithelial cells (IEC) from two mice (A/J) per treatment orally challenged with WT and ΔinlA strains (see FIG. 1) but not in $lap^-$ strain, relative to uninfected (control) mice, each sacrificed after 48 h. Densitometry reports are graphed below each blot (6F and 6G) which represent mean±SEM of two independent mice per treatment. *, P<0.001; , P<0.01.

FIG. 6H shows confocal-immunofluorescence microscopy of the ileal tissue sections showing mis-localization of occludin, claudin-1 and E-cadherin (labeled in red) and increased expression of P-MLC (labeled in green) in mice (A/J) orally challenged with WT and ΔinlA strains indicated with yellow arrows but not in $lap^-$ strain relative to uninfected (control) mice, indicated with white arrows each sacrificed after 48 h (see FIGS. 1A-1G). Nuclei were counterstained with DAPI (blue). Pictures are representative of five different fields from two to three mice per treatment. Scale bars, 50 μm.

FIGS. 7A-7E show that six-eight-week-old wild-type C57BL/6 ($MLCK^{+/+}$) or the 210-kDa MLCK knockout mice ($MLCK^{-/-}$) were orally gavaged with $1\times10^9$ CFU of WT, lap or ΔinlA *L. monocytogenes* bacteria. In each group, 2-5 females and 2 males were used. The scatter plot shows the total CFU obtained from the liver (FIG. 7A), spleen (FIG. 7B), MLN (FIG. 7C), ileal mucus layer (FIG. 7D), ileal epithelial cell (intracellular+extracellular) (FIG. 7E), and ileal lamina propria (intracellular+extracellular) (FIG. 7F) of mice (n=4-7) at 24 and 48 h pi from three independent experiments. Reduced *L. monocytogenes* counts (CFU) were recovered in the liver, spleen, MLN and lamina propria of $MLCK^{+/+}$ mice challenged with the $lap^-$ strain or $MLCK^{-/-}$ mice challenged with the WT or the $lap^-$ strain. Bar and brackets represent the mean±SEM, respectively, for the data points in each group. Dashed horizontal lines indicate the limit of detection for each organ/tissue. **, P<0.0001; , P<0.01; *, P<0.5; ns, no significance.

FIGS. 7G-7H show analysis of para-cellular permeability of 4-kDa FITC-dextran (FD4) through intestinal epithelium administered 4-5 h before sacrifice, in serum (FIG. 7G) and urine (FIG. 7H) from the $MLCK^{+/+}$ or the $MLCK^{-/-}$ (n=4-7) mice at 24 and 48 h pi. $MLCK^{+/+}$ mice challenged with the $lap^-$ strain or $MLCK^{-/-}$ mice challenged with the WT or the lap-strain exhibited significantly decreased FD4 flux relative to $MLCK^{+/+}$ mice challenged with the WT or the ΔinlA strains. Data represent mean±SEM of 3-4 control mice and 5-7 challenged mice per treatment from three independent experiments. **, P<0.01; *, P<0.5; ns.

FIG. 7I shows confocal immunofluorescence microscopy of the ileal tissue sections showing mis-localization of occludin, claudin-1 and E-cadherin (labeled in red) and increased expression of P-MLC (labeled in green) in $MLCK^{+/+}$ mice challenged with WT or the ΔinlA strains (yellow arrows) but not in $MLCK^{+/+}$ mice challenged with the $lap^-$ strain or $MLCK^{-/-}$ mice challenged with the WT or the $lap^-$ strain and the uninfected (control) mice (white arrows). Nuclei were counterstained with DAPI (blue). Pictures are representative of five different fields from 2-3 mice per treatment. Scale bars, 50 μm. LP, Lamina Propria.

FIG. 7J shows proposed model of the LAP-mediated translocation of *L. monocytogenes* through the intestinal epithelial barrier. *L. monocytogenes* uses LAP to breach the epithelial barrier through activation of NF-κB and MLCK to facilitate translocation of *Listeria* across the epithelium during the intestinal phase of infection, and during that time, it may facilitate an interaction between InlA and E-cadherin at the adherens junction (AJ) for intracellular translocation in permissive hosts, such as humans and guinea pigs. The LAP-Hsp60 interaction is a key biological event that propels *L. monocytogenes* across the epithelium for extra-intestinal dissemination in the ΔinlA strain or in the absence of an InlA-specific E-cadherin interaction, as in the mouse model.

FIG. 8A (Top) is schematic representation of LAP, an alcohol acetaldehyde dehydrogenase enzyme (AAD; 866 aa) consisting of an N-terminal acetaldehyde dehydrogenase (ALDH) and a C-terminal alcohol dehydrogenase region (ADH); FIG. 8A (Bottom) shows purity of recombinant LAP domains; N1, N2, C1 and C2 (2 μg/lane) was determined by SDS-PAGE and Coomassie blue staining.

FIG. 8B shows analysis of NF-κB stimulating ability of LAP domains using RAW 264.7 NF-κB luciferase reporter cell line. Cells were stimulated with LAP, N1, N2, C1 and C2 (1 μg/ml, each) for 6 h and analyzed for luciferase activity. Bars indicate fold induction compared with unstimulated cells and are represented as mean±SEM (in =6). *p<0.05, **p<0.01; and ns: not significant.

DETAILED DESCRIPTION

Figure 1A:
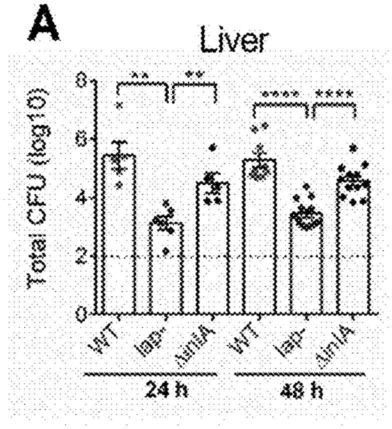
FIGS. 1A-1H demonstrate that *L. monocytogenes* Listeria Adhesion Protein (LAP, SEQ ID NO.: 1) contributes to systemic dissemination and translocation across the intestinal barrier.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

The present invention generally relates to a method for enhanced delivery of a drug across epithelial barriers using a peptide derived from Listeria adhesion protein (LAP). In particular, the present invention discloses a non-invasive drug delivery method using Listeria adhesion protein (LAP) or a fragment of ten or more continuous amino acid residues thereof. Incorporation of those peptides or a fragment thereof, either as a physical mixture of a pharmaceutical formulation or as a covalent construction at a molecular level or nanoscale is within the scope of this disclosure.

In some illustrative embodiments, the present invention relates to a method for enhancing delivery efficiency of a drug to systemic circulation comprising comprising incorporating Listeria Adhesion Protein (LAP, SEQ ID NO: 1), a polypeptide of 90%, or more sequence identity, or a fragment of any 20 or more continuous amino acid residues thereof, by physical mixing or covalent attachment, to said drug to be delivered.

In some illustrative embodiments, the present invention relates to a method for enhancing delivery efficiency of a drug to systemic circulation comprising incorporating a polypeptide of N2 domain of LAP having the sequence of SEQ ID NO: 2, an analogue of 90% or more sequence identity, or a fragment of any ten or more continuous amino acid residues thereof.

In some illustrative embodiments, the present invention relates to a method for enhancing delivery efficiency of a drug to systemic circulation comprising incorporating a polypeptide of N2 domain of LAP having the sequence of SEQ ID NO: 2, an analogue of 90% or more sequence identity, or a fragment of any ten or more continuous amino acid residues thereof, wherein said LAP polypeptide (SEQ ID NO: 1), an analogue of 90% or more sequence identity, or a fragment of any 10 or more continuous amino acid residues thereof, is covalently linked to the drug to be delivered.

In some illustrative embodiments, the present invention relates to a method for enhancing delivery efficiency of a drug to systemic circulation comprising incorporating a polypeptide of N2 domain of LAP having the sequence of SEQ ID NO: 2, an analogue of 900/% or more sequence identity, or a fragment of any ten or more continuous amino acid residues thereof, wherein said LAP polypeptide (SEQ ID NO: 1), an analogue of 90% or more sequence identity, or a fragment of any 10 or more continuous amino acid residues thereof, is co-formulated together with the drug to be delivered.

In some illustrative embodiments, the present invention relates to a method for enhancing delivery efficiency of a drug to systemic circulation comprising incorporating a polypeptide of N2 domain of LAP having the sequence of SEQ ID NO: 2, an analogue of 90% or more sequence identity, or a fragment of any ten or more continuous amino acid residues thereof, wherein the route of drug delivery is via an epithelial surface.

In some illustrative embodiments, the present invention relates to a method for enhancing delivery efficiency of a drug to systemic circulation comprising incorporating a polypeptide of N2 domain of LAP having the sequence of SEQ ID NO: 2, an analogue of 90% or more sequence identity, or a fragment of any ten or more continuous amino acid residues thereof, wherein the route of drug delivery is per oral, via submucosal, virginal or rectal route.

In some illustrative embodiments, the present invention relates to a pharmaceutical composition comprising one or more polypeptides disclosed herein, a pharmaceutically acceptable salt thereof, in combination with one or more therapeutically effective compounds, together with one or more diluents, excipients or carriers.

In some illustrative embodiments, the present invention relates to a pharmaceutical composition comprising one or more polypeptides disclosed herein, a pharmaceutically acceptable salt thereof, in combination with one or more therapeutically effective compounds, together with one or more diluents, excipients or carriers, wherein said polypeptide comprises a Listeria adhesion protein (LAP), having the sequence of SEQ ID NO: 1, a polypeptide of 90% or more sequence identity, or a fragment of any 20 or more continuous amino acid residues thereof.

In some illustrative embodiments, the present invention relates to a pharmaceutical composition comprising one or more polypeptides disclosed herein, a pharmaceutically acceptable salt thereof, in combination with one or more therapeutically effective compounds, together with one or more diluents, excipients or carriers, wherein said polypeptide comprises N2 domain having the sequence of SEQ ID NO: 2, a polypeptide of 90% or more sequence identity, or a fragment of any 10 or more continuous amino acid residues thereof.

In some illustrative embodiments, the present invention relates to a method for enhancing delivery efficiency of a drug to systemic circulation comprising incorporating a polypeptide of N2 domain (SEQ ID NO: 2), an analogue of 90% or more sequence identity, or a fragment of any 10 or more continuous amino acid residues thereof, by physical mixing or covalent attachment, to said drug to be delivered.

In some illustrative embodiments, the present invention relates to a method for enhancing delivery efficiency of a drug to systemic circulation comprising incorporating a polypeptide of N2 domain (SEQ ID NO: 2), an analogue of 90% or more sequence identity, or a fragment of any 10 or more continuous amino acid residues thereof, by physical mixing or covalent attachment, to said drug to be delivered, wherein said polypeptide of N2 domain (SEQ ID NO: 2), an analogue of 90% or more sequence identity, or a fragment of any 10 or more continuous amino acid residues thereof, is covalently linked to the drug to be delivered.

In some illustrative embodiments, the present invention relates to a method for enhancing delivery efficiency of a drug to systemic circulation comprising incorporating a polypeptide of N2 domain (SEQ ID NO: 2), an analogue of 90% or more sequence identity, or a fragment of any 10 or more continuous amino acid residues thereof, by physical mixing or covalent attachment, to said drug to be delivered, wherein said polypeptide of N2 domain (SEQ ID NO: 2), an analogue of 90% or more sequence identity, or a fragment of any 10 or more continuous amino acid residues thereof, is co-formulated together with the drug to be delivered.

In some illustrative embodiments, the present invention relates to a method for enhancing delivery efficiency of a drug to systemic circulation comprising incorporating a polypeptide of N2 domain (SEQ ID NO: 2), an analogue of 90% or more sequence identity, or a fragment of any 10 or more continuous amino acid residues thereof, by physical mixing or covalent attachment, to said drug to be delivered, wherein the route of drug delivery is via an epithelial surface.

In some illustrative embodiments, the present invention relates to a method for enhancing delivery efficiency of a drug to systemic circulation comprising incorporating a polypeptide of N2 domain (SEQ ID NO: 2), an analogue of 90% or more sequence identity, or a fragment of any 10 or more continuous amino acid residues thereof, by physical mixing or covalent attachment, to said drug to be delivered, wherein the route of drug delivery is per oral, via submucosal, virginal or rectal route.

In some illustrative embodiments, the present invention relates to a pharmaceutical composition comprising one or more polypeptides of claim 10, wherein said polypeptide comprises N2 domain having the sequence of SEQ ID NO: 2, a polypeptide of 90% or more sequence identity, or a fragment of any 10 or more continuous amino acid residues thereof, a pharmaceutically acceptable salt thereof, in combination with one or more therapeutically effective compounds.

In some illustrative embodiments, the present invention relates to a method for enhancing delivery efficiency of a drug to systemic circulation comprising incorporating a polypeptide of N2 domain (SEQ ID NO: 3), an analogue of 90% or more sequence identity, or a fragment of any 10 or more continuous amino acid residues thereof, by physical mixing or covalent attachment, to said drug to be delivered.

In some illustrative embodiments, the present invention relates to a method for enhancing delivery efficiency of a drug to systemic circulation comprising incorporating a polypeptide of N2 domain (SEQ ID NO: 3), an analogue of 90% or more sequence identity, or a fragment of any 10 or more continuous amino acid residues thereof, by physical mixing or covalent attachment, to said drug to be delivered, wherein said polypeptide of N2 domain (SEQ ID NO: 3), an analogue of 90% or more sequence identity, or a fragment of any 10 or more continuous amino acid residues thereof, is covalently linked to the drug to be delivered.

In some illustrative embodiments, the present invention relates to a method for enhancing delivery efficiency of a drug to systemic circulation comprising incorporating a polypeptide of N2 domain (SEQ ID NO: 3), an analogue of 90% or more sequence identity, or a fragment of any 10 or more continuous amino acid residues thereof, by physical mixing or covalent attachment, to said drug to be delivered, wherein said polypeptide of N2 domain (SEQ ID NO: 3), an analogue of 90% or more sequence identity, or a fragment of any 10 or more continuous amino acid residues thereof, is co-formulated together with the drug to be delivered.

In some illustrative embodiments, the present invention relates to a method for enhancing delivery efficiency of a drug to systemic circulation comprising incorporating a polypeptide of N2 domain (SEQ ID NO: 3), an analogue of 90% or more sequence identity, or a fragment of any 10 or more continuous amino acid residues thereof, by physical mixing or covalent attachment, to said drug to be delivered, wherein the route of drug delivery is via an epithelial surface.

In some illustrative embodiments, the present invention relates to a method for enhancing delivery efficiency of a drug to systemic circulation comprising incorporating a polypeptide of N2 domain (SEQ ID NO: 3), an analogue of 90% or more sequence identity, or a fragment of any 10 or more continuous amino acid residues thereof, by physical mixing or covalent attachment, to said drug to be delivered, wherein the route of drug delivery is per oral, via submucosal, virginal or rectal route.

In some illustrative embodiments, the present invention relates to a method for enhancing delivery efficiency of a drug to systemic circulation according to the method disclosed herein, wherein the route of drug delivery is per oral.

In some illustrative embodiments, the present invention relates to a method for enhancing delivery efficiency of a drug to systemic circulation according to the method disclosed herein, wherein the route of drug delivery is submucosal.

In some illustrative embodiments, the present invention relates to a method for enhancing delivery efficiency of a drug to systemic circulation according to the method disclosed herein, wherein the route of drug delivery is via virginal or rectal route.

In some illustrative embodiments, the present invention relates to a pharmaceutical composition comprising one or more polypeptides of SEQ ID NO. 1 or 2, a pharmaceutically acceptable salt thereof, in combination with one or more therapeutically effective compounds, together with one or more diluents, excipients or carriers.

In some illustrative embodiments, the present invention relates to a method for enhancing delivery efficiency of a drug to systemic circulation comprising a polypeptide of N2 domain having the sequence of SEQ ID NO: 2 or a fragment of any ten or more continuous amino acid residues thereof, wherein the route of drug delivery is via an epithelial surface.

In some illustrative embodiments, the present invention relates to a method for enhancing delivery efficiency of a drug to systemic circulation comprising a polypeptide of N2 domain having the sequence of SEQ ID NO: 2 or a fragment of any ten or more continuous amino acid residues thereof, wherein the route of drug delivery is per oral.

In some illustrative embodiments, the present invention relates to a method for enhancing delivery efficiency of a drug to systemic circulation comprising a polypeptide of N2 domain having the sequence of SEQ ID NO: 2 or a fragment of any ten or more continuous amino acid residues thereof, wherein the route of drug delivery is submucosal.

In some illustrative embodiments, the present invention relates to a method for enhancing delivery efficiency of a drug to systemic circulation comprising a polypeptide of N2 domain having the sequence of SEQ ID NO: 2 or a fragment of any ten or more continuous amino acid residues thereof, wherein the route of drug delivery is via virginal or rectal route.

In another aspect, the present invention also may include those polypeptides which exhibit at least 85%, more preferably at least 90% identity, and most preferably at least 95% identity to a polypeptide sequence selected from the group of sequences set forth above. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. Computer programs can be used to determine "identity" between two sequences these programs include but are not limited to, GCG; suite of five BLAST programs, three designed for nucleotide sequences queries (BLASTN, BLASTX, and TBLASTX) and two designed for protein sequence queries (BLASTP and TBLASTN). The BLAST X program is publicly available from NCBI and other sources. The well-known Smith Waterman algorithm can also be used to determine identity.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure, the term "substantially" can allow for a degree of variability in a value or range, for example, within 90%, within 95%, 99%, 99.5%, 99.9%, 99.99%, or at least about 99.999% or more of a stated value or of a stated limit of a range.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient, the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

The breaching of host barriers (intestinal, blood-brain, and placental) is a key mechanism of *Listeria monocytogenes* infection. The gastrointestinal tract is the primary route of infection for this foodborne pathogen, and crossing the intestinal epithelial barrier is the first step in the infection process. *L. monocytogenes* is a highly adaptable pathogen and is capable of making a transition from a soil-living saprophyte to a pathogen in the host during foodborne infection (Freitag, N. E. et al., *Nat. Rev. Microbiol.* 2009, 7, 623-628). The importance of the Internalin A (InlA)-mediated epithelial invasion of *L. monocytogenes* via an intracellular route has been demonstrated, and it requires interaction between the *Listeria* surface protein InlA and E-cadherin (Lecuit M., et al., *Science,* 2001, 292, 1722-1725). The InlA/E-cadherin interaction exhibits a species specificity that is attributed to a variation at amino acid sequence position 16, at which Pro is substituted by Glu in the host species' E-cadherin (Lecuit M., et al., *EMBO J.* 1999, 18, 3956-3963). Therefore, InlA does not interact with the mouse or rat E-cadherin, but it does interact with the E-cadherin of permissive hosts, such as humans and guinea pigs (Lecuit M., et al., 1999). E-cadherin is an adherens junction (AJ) protein that is expressed basolaterally and is inaccessible to bacteria located in the intestinal lumen. The proposed mechanisms by which InlA accesses E-cadherin include villous epithelial "cell extrusion" during which the apical junctional complex proteins are redistributed to the lateral membranes (Marchiando, A M, et al., *Gastroenterology,* 2011, 140, 1208-1218. E1202) and the transcytosis of *L. monocytogenes* near mucus-expelling goblet cells (Nikitas, G. et al., *J. Exp. Med.* 2011, 208, 2263-2277). However, the intragastric (ig) inoculation of a ΔinlA mutant strain resulted in high bacterial burdens in the small intestine and mesenteric lymph nodes (MLN) of wild-type mice (Lecuit M., et al., *Science,* 2001, 292, 1722-1725) and small intestine, cecum, colon, and mesenteric lymph nodes (MLN) of transgenic mice expressing "humanized" E-cadherin (Disson, O, et al., *Nature,* 2008, 455, 1114-1118). This suggests that the humanized E-cadherin allele is only relevant to InlA-mediated bacterial invasion and that *L. monocytogenes* use alternate routes to translocate across the gut mucosa. Furthermore, significant differences were not observed in bacterial burdens in the liver, spleen and MLN of mice that were ig-inoculated with *L. monocytogenes* expressing murinized InlA ($InlA^m$), which binds E-cadherin with high affinity compared to mice that were ig-inoculated with the wild-type *L. monocytogenes* for up to 48 h post-infection (pi). This finding further suggests that the InlA-E-cadherin interaction may not be essential for *L. monocytogenes* to cross the intestinal barrier, at least during the early phase of infection. A co-infection study using $InlA^m$, wild-type or ΔinlA mutant strains demonstrated that InlA is not required for the establishment of intestinal infection in mice.

The interaction between InlA and E-cadherin in non-permissive hosts (e.g., mice and rats) is not fully functional (Lecuit M., et al., 1999 and 2001). However, several studies have advocated that *L. monocytogenes* can cross the intestinal barrier and disseminate to the MLN, liver, and spleen following oral infection (Jadadeesan, B. et al., *Microbiology,* 2010, 156, 2782-2795). In non-permissive hosts, the murine M cells in Peyer's patches are considered to be the main invasive route for *L. monocytogenes* translocation and this mechanism is independent of InlA or listeriolysin O (LLO). However, *L. monocytogenes* was found to translocate to deeper tissues and organs with similar efficiencies in a rat ligated ileal loop with or without Peyer's patches. Furthermore, in a Peyer's patches null mouse, *L. monocytogenes* was found to colonize the ileum and disseminate to the MLN, liver and spleen in a ligated loop assay (Chiba, S. et al., *Microbiol. Immunol.* 2011, 55, 123-129). These findings indicate that *L. monocytogenes* also translocates across the epithelium independently of InlA and M cells and that other routes of invasion in the gastrointestinal tract are possible. InlA-mediated uptake and M-cell transcytosis have been systematically studied, but other routes used by *L. monocytogenes* to translocate across and disseminate from the gastrointestinal tract have not been examined (Zhang, T. et al., *Proc Nat Acad Sci USA* 2017, 114, 6334-6339).

We previously reported that the translocation of *L. monocytogenes* across human enterocyte-like Caco-2 barrier is dependent on an interaction of *Listeria* adhesion protein (LAP) with the mammalian host cell receptor chaperonin 60 (Hsp60) and is independent of InlA (Burkholder, K M, et al., *Infect. Immun.* 2010, 78, 5062-5073). LAP (lmo1634) is a moonlighting protein with alcohol acetaldehyde dehydrogenase activity that exhibits adhesion properties in pathogenic *Listeria* species (Jadadeesan, B. et al., 2010). The present study investigates whether LAP contributes to translocation of *L. monocytogenes* across the intestinal barrier independently of InlA and elucidates the molecular mechanism by which LAP facilitates *L. monocytogenes* translocation. We used a mouse model (wild-type and knockout) in combination with human enterocyte-like Caco-2 cells and demonstrate that LAP contributes to *L. monocytogenes* translocation into the lamina propria, systemic dissemination, and increased intestinal epithelial permeability. Further, we show that the increased permeability directly correlates with the increased expression of NF-κB-regulated pro-inflammatory cytokines, such as TNF-α and IL-6, in WT- and ΔinlA-challenged mice, but not lap-deficient *L. monocytogenes*-challenged mice. By using genetic models and pharmacological inhibitors, we establish that LAP directly binds to Hsp60 to activate canonical NF-κB(p65) signaling, thereby facilitating the myosin light chain kinase (MLCK)-mediated opening of the intestinal cell-cell junction barrier via the cellular redistribution of the major junctional proteins, claudin-1, occludin and E-cadherin, and bacterial translocation.

Figure 1B:
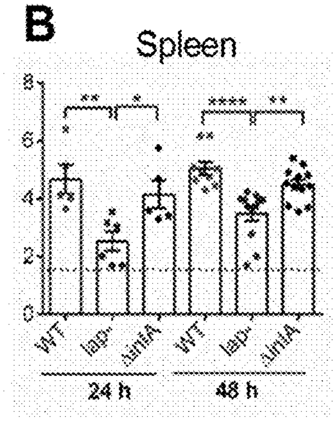
Figure 1C:
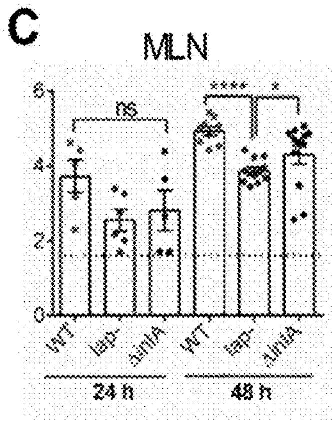

LAP contributes to systemic dissemination and translocation across the intestinal barrier. To determine the impact of LAP on virulence, we orally challenged A/J mice with a wild-type (WT) strain (serotype 4b), an isogenic lap-insertion mutant strain ($lap^-$) and an ΔinlA deletion mutant strain, and enumerated *Listeria* in the extra-intestinal sites at 24 and 48 h pi. The dissemination of $lap^-$ bacteria was significantly impaired (~1.5-2.0 log reduction) in the liver and spleen compared to the WT and ΔinlA strains at 24 and 48 h pi (FIGS. 1A and 1B). The $lap^-$ strain also exhibited a colonization defect in the MLN at 24 h (~1.0 log reduction), and contained significantly lower numbers at 48 h pi (~0.7 log reduction) compared to the WT and ΔinlA strains (FIG. 1C). Reduced numbers of the $lap^-$ strain were observed in the kidneys at 48 h pi, and this strain was undetectable in blood. These results were consistent with the histological analyses of livers and spleens, which identified mild-to-moderate multifocal hepatic necrosis in the livers and multifocal areas of necrosis and neutrophilia in the white and red pulp in spleens of mice challenged with the WT or ΔinlA strain at 48 h pi. However, lesions were not identified in the livers of mice challenged with the $lap^-$ strain, and only a mild inflammatory infiltrate was identified in the spleen of one of the five analyzed mice. Taken together, these data confirm that the $lap^-$ strain exhibited a dissemination defect in trafficking to extra-intestinal sites.

Figure 1D:
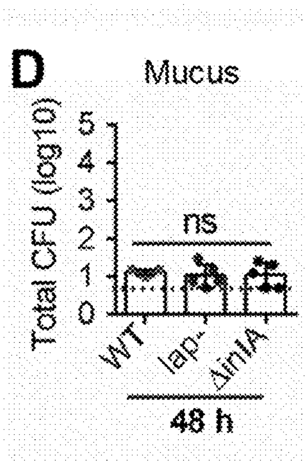
Figure 1E:
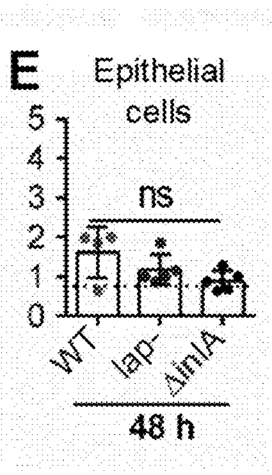
Figure 1F:
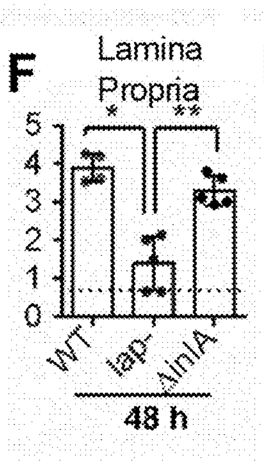
Figure 1H:
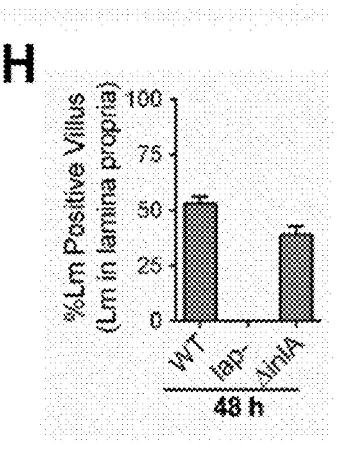
Figure 1G:
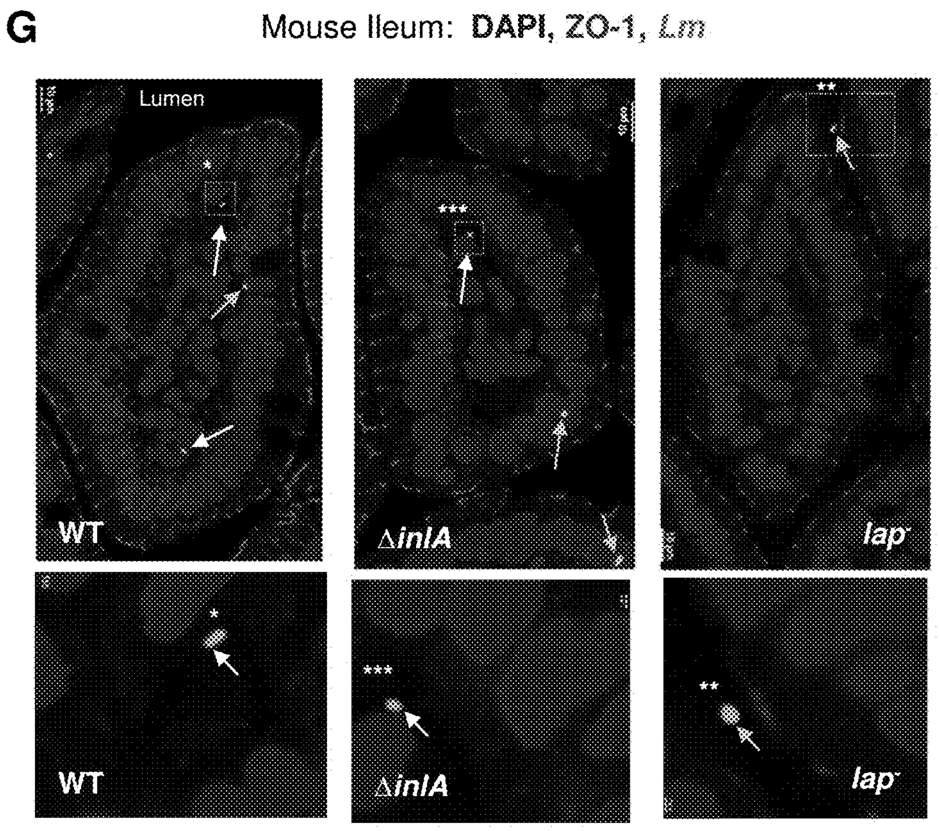

(I) We then determined whether the defect in systemic dissemination of the $lap^-$ strain was due to the defect in translocation of this strain from the intestinal lumen, across the gut epithelium into the underlying lamina propria. We enumerated *L. monocytogenes* counts in the mucus, epithelial cells and lamina propria fractions of the ileal mucosa at 48 h pi. Relative to WT strain, no significant difference was observed in the total number of $lap^-$ bacteria present in the mucus layer (FIG. 1D), and a slight reduction (~0.5 log) in the epithelial cell fraction was observed (FIG. 1E). However, we observed a significantly lower (~2-2.5 log) number of lap-bacteria in the lamina propria, compared to the WT strain or the ΔinlA strain (FIG. 1F). These results were consistent with our immunofluorescence staining observations; where we detected the WT- and ΔinlA strains in the lamina propria of 50% and 38%, respectively of the total villi (n=50) examined (FIGS. 1G, 1H). In contrast, the $lap^-$ strain was not found in the lamina propria, but remained in the lumen of all villi sections examined. As expected, the $lap^-$ bacteria was found in the ileal Peyer's patches. These data suggest that LAP contributes to translocation of *L. monocytogenes* across the intestinal barrier into the underlying lamina propria in a mouse model.

Figure 2A:
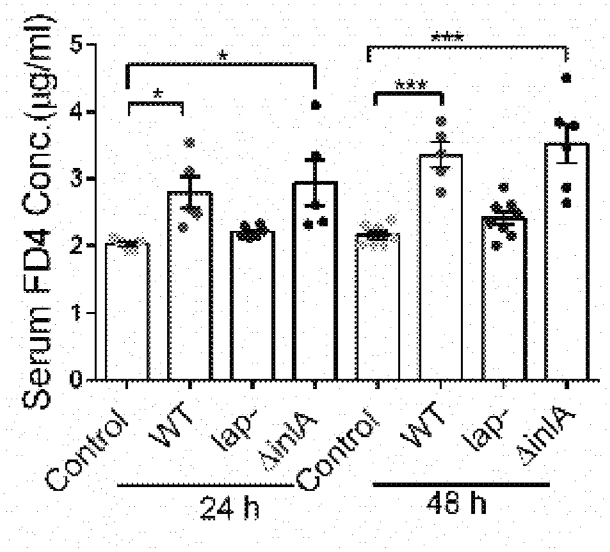
FIGS. 2A-2J show that LAP contributes to intestinal barrier dysfunction.
Figure 2B:
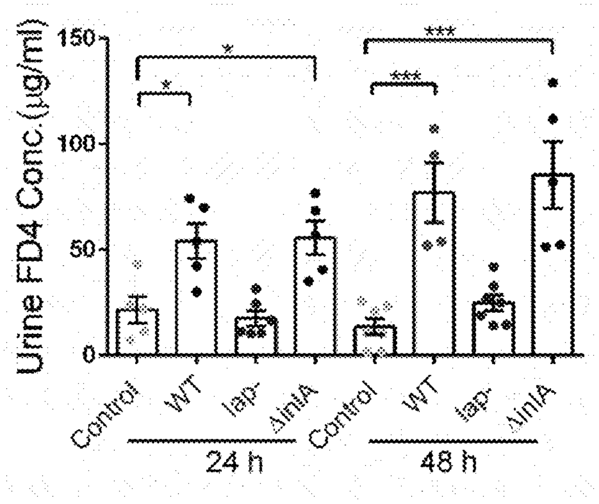
Figure 2C:
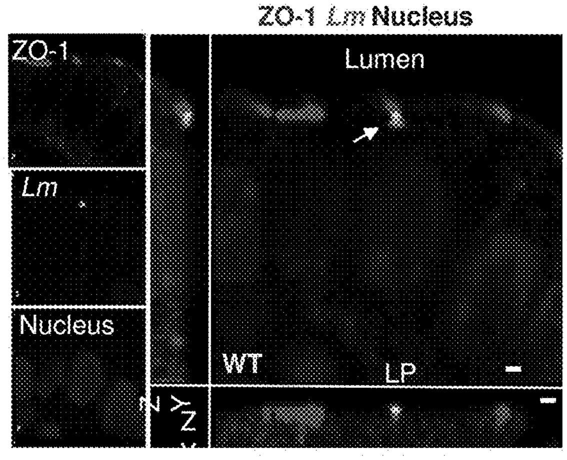
Figure 2D:
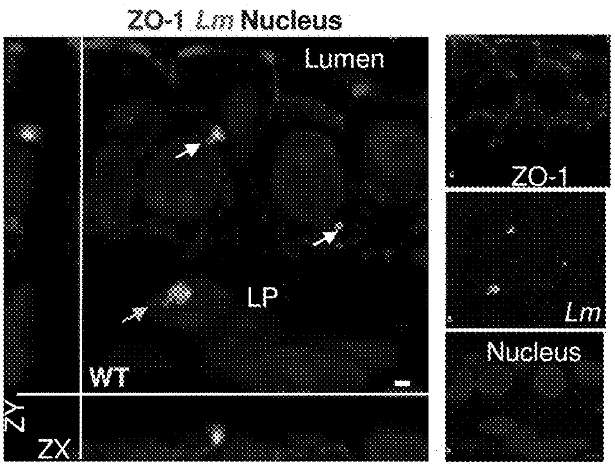
Figure 2E:
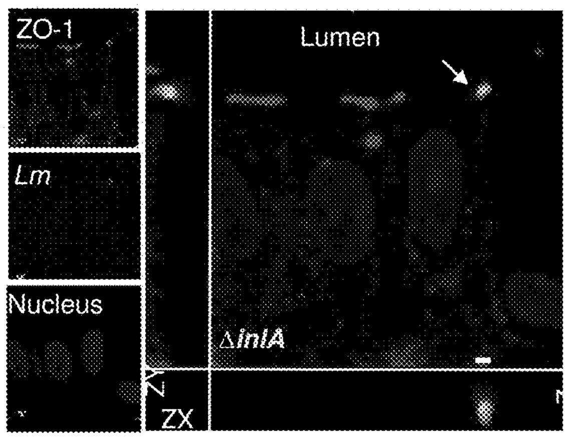
Figure 2F:
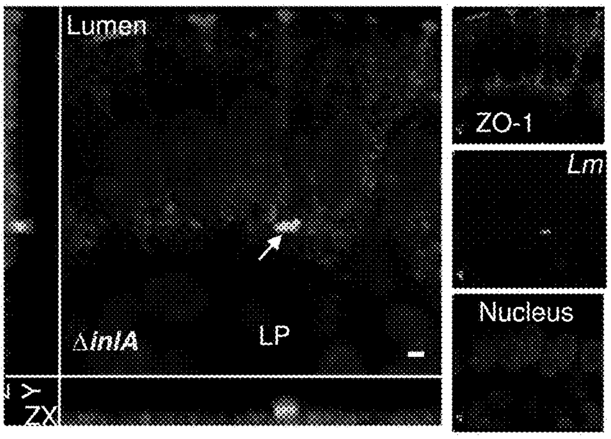

LAP contributes to intestinal barrier dysfunction. We next investigated whether LAP increases epithelial permeability for translocation of *L. monocytogenes* across the intestinal epithelium. We orally gavaged *L. monocytogenes*—infected mice with a marker of paracellular permeability, 4-kDa FITC-dextran (FD4), 4-5 h prior to sacrifice, and measured its concentration in serum and the urine (Meddings, J B et al., *Gastroenterology,* 2000, 119, 1019-1028; Wang L. et al., *J. Immunol. Methods* 2015, 421, 44-53). Relative to the uninfected controls, the FD4 concentrations were significantly increased by approximately 44±5% and 67±8% in the serum at 24 h and 48 h pi, respectively, and by 185±32% and 445±20% in the urine at 24 h and 48 h pi, respectively, in WT and ΔinlA-challenged mice (FIGS. 2A and 2B). However, the FD4 concentrations were significantly lower in mice challenged with the $lap^-$ strain in comparison to WT and ΔinlA-challenged mice, and did not increase significantly relative to the uninfected controls. Additionally, we observed by immunofluorescence staining that *L. monocytogenes* WT and ΔinlA strains localized at the cell-cell junction of epithelial cells in mouse ileum, as evidenced by co-localization of *L. monocytogenes* with the tight junction (TJ) protein, ZO-1 (FIGS. 2C-2F). In contrast, the $lap^-$ strain was predominantly confined in the lumen of the ileal mucosa (FIG. 1G).

Figure 2G:
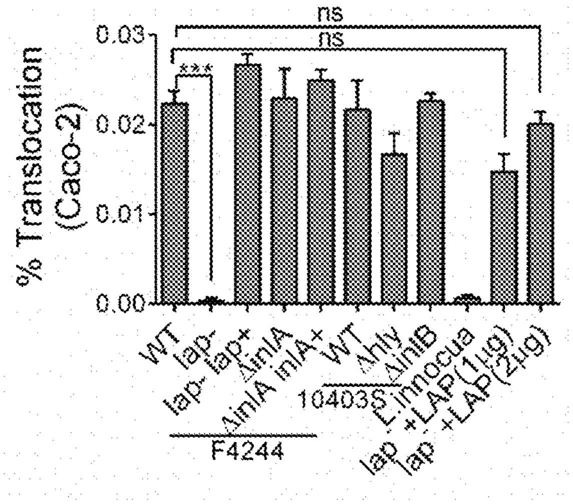
Figure 2H:
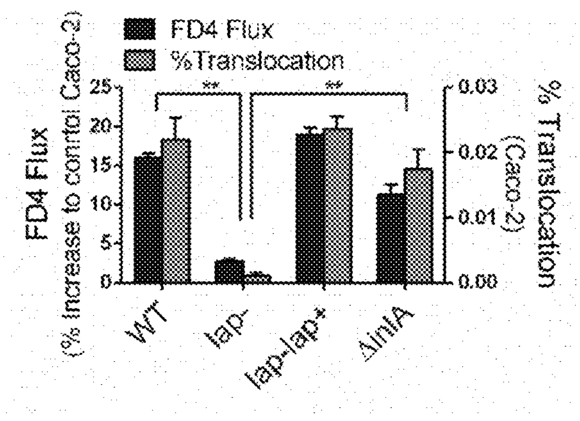

Next we investigated the translocation phenotypes of the ΔinlB and Δhly (LLO) strains in conjunction with the $lap^-$ and ΔinlA strains across Caco-2 monolayers grown on Transwell inserts. The translocation rates of the ΔinlA, ΔinlB and Δhly strains were similar to or higher than their respective WT counterparts (FIG. 2G). By contrast, the $lap^-$ strain exhibited a severely attenuated translocation phenotype and the $lap^-lap^-$ complemented strain, restored translocation equal or higher than the WT strain. These findings are consistent with our previous in vivo observations (Burkholder, et al., 2010), where we observed that the $lap^-lap^+$ complemented strain translocated to the liver and spleen of orally challenged A/J mice to similar levels as the WT strain. These data suggest that the gene complementation with lap sufficiently restored the in vitro and in vivo translocation defect of the *L. monocytogenes* $lap^-$ strain. Additionally, the attenuated translocation of the $lap^-$ strain correlated with significantly decreased (~5 fold) FD4 flux across Caco-2 cells infected with $lap^-$ strain in comparison to cells infected with the WT strain (FIG. 2H). Importantly, the translocation defect observed by the $lap^-$ strain was not due to decreased cytopathic or cytotoxic effects, as Caco-2 cells infected with the $lap^-$ strain showed similar levels of lactate dehydrogenase release as the WT strain.

(II) To delineate the intracellular role of LAP from its role at the bacterial cell surface, we first determined the relevant concentration of LAP available on the bacterial surface during the infection of Caco-2 cells by using purified recombinant LAP protein as the standard. Immunoblotting experiments suggested that approximately 1 μg of LAP was associated with the cell wall of WT bacteria at $1\times10^7$ CFU, and an equivalent CFU was used in our translocation assays to achieve a multiplicity of infection (MOI) of 50. Pre-incubation of lap-bacteria with exogenously purified LAP, at a concentration that is available on the bacterial surface, resulted in a strong association of the protein with the bacterial cell wall and rescued the translocation defect of the $lap^-$ strain across Caco-2 barrier (FIG. 2G). These data suggest that exogenously added purified LAP is able to promote the translocation of the $lap^-$ mutant across Caco-2 barrier.

Figure 2I:
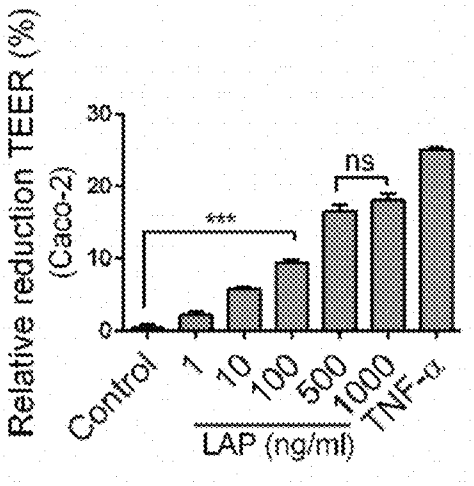
Figure 2J:
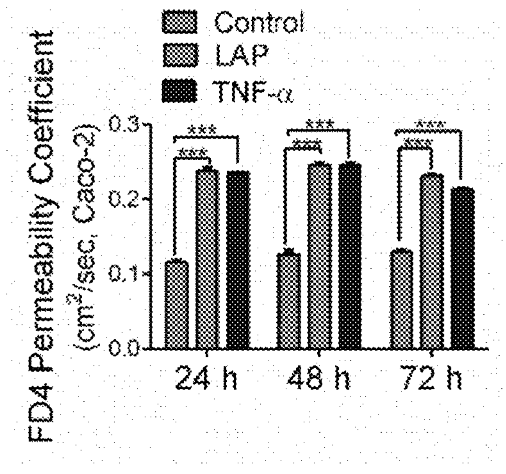

(III) To study the effect of LAP on epithelial permeability, we analyzed transepithelial electrical resistance (TEER), which demonstrated that the addition of purified recombinant LAP to Caco-2 monolayers, produced a 12±1%, 27±1% and 25±2% reduction in TEER, when LAP was added to the apical, basolateral or both the basolateral and apical compartments, respectively. A dose-response study revealed that apical treatment of purified LAP produced a concentration-dependent reduction in TEER during the 48-h experimental period, with a maximum reduction observed at 500-1000 ng/mL of LAP treatment (FIG. 2I). Monitoring of FD4 translocation over a 72-h period suggested that purified LAP caused a significant increase in FD4 permeability equivalent to TNF-α as a positive control (FIG. 2J). These data suggest that purified recombinant LAP is biologically active and sufficient to alter Caco-2 barrier permeability.

Collectively, these data confirm that *L. monocytogenes* increase paracellular permeability, which is LAP-dependent, and suggest a positive correlation between paracellular permeability and *Listeria* translocation in a Caco-2 model and a mouse model, where the InlA-E-cadherin interaction is not fully functional (Lecuit et al., 2001).

Figure 3A:
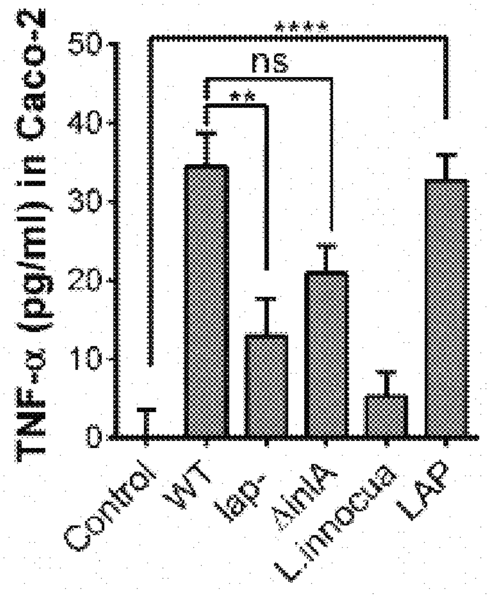
FIGS. 3A-3K demonstrate that LAP regulates the expression of TNF-α and IL-6 in Caco-2 cells and mouse ileal tissue.
Figure 3B:
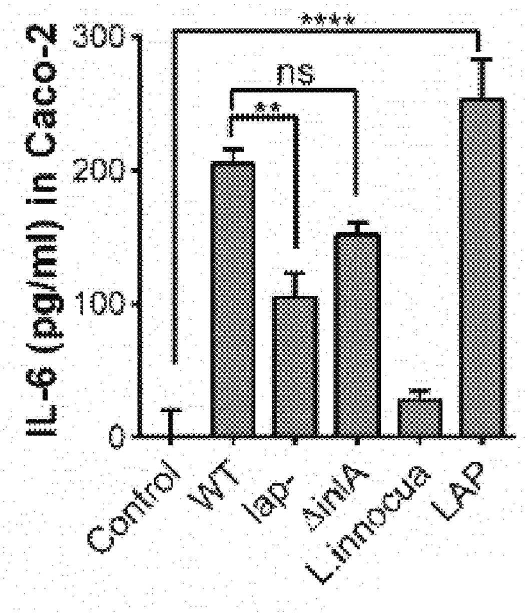
Figure 3C:
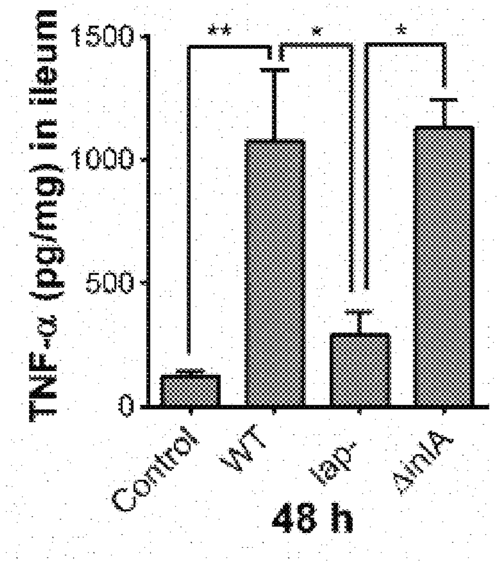
Figure 3D:
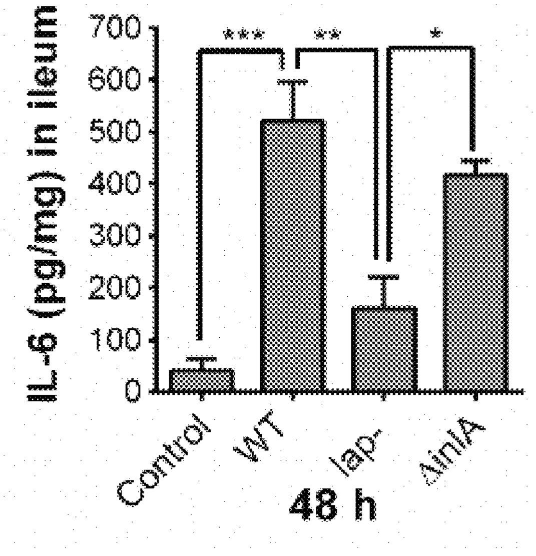
Figure 3E:
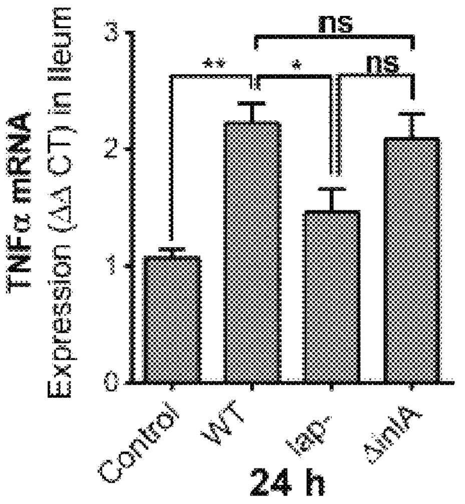
Figure 3F:
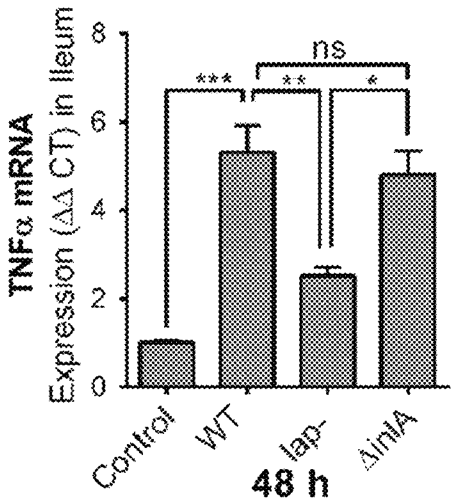
Figure 3G:
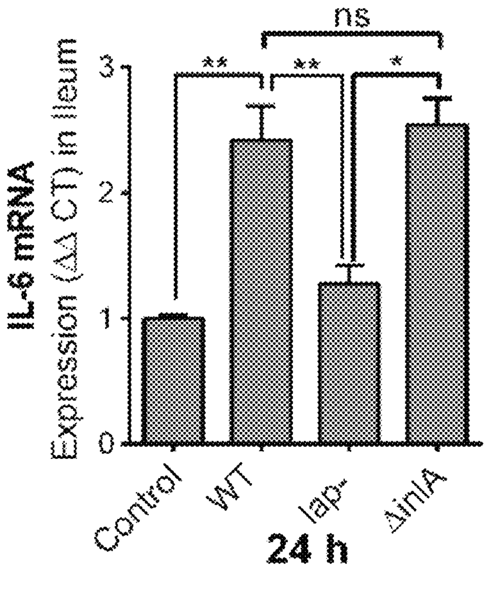
Figure 3H:
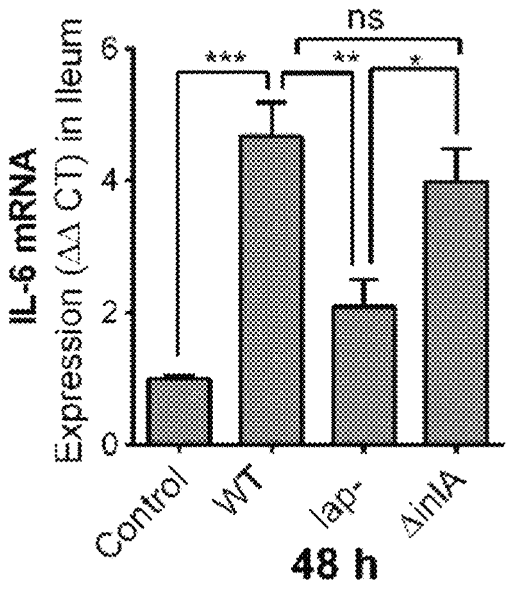

*L. monocytogenes* LAP upregulates TNF-α and L-6 expression in Caco-2 cells and the murine ileal mucosa. Cytokines play a crucial role in the modulation of inflammatory responses in the gastrointestinal tract, and several pro-inflammatory cytokines, such as TNF-α, IL-1, IL-6, IL-8, and IFN-γ, produce disturbances in the intestinal cell-cell junction barrier, which promotes the increased epithelial permeability and penetration of luminal antigens (Al-Sadi, R. et al., PLoS ONE 2014, 9; Ma, T Y et al., *Am. J. Physiol. Gastrointes. Liver Physiol.* 2004, 286, G367-G376). *L. monocytogenes* upregulates IL-8, MCP1, GMCSF, and TNF-α in epithelial cells, including Caco-2 cells, and the intestinal host response is InlA-independent (Lecuit, M. et al., *J. Biol. Chem.* 2007, 282, 15065-15072). Therefore, we investigated whether LAP contributes to cytokine dysregulation. We compared the expression of 40 inflammatory mediators in culture supernatants of Caco-2 monolayers infected with WT or $lap^-$ bacteria using a cytokine dot-blot array. Densitometric analyses of the arrays revealed that many pro-inflammatory cytokines, such as TNF-α, IL-6, IL-8, and IFN-γ, and the chemokine MCP-2 were downregulated when infected with the $lap^-$ strain compared to the WT strain (FIGS. 3A and 3B). Two pro-inflammatory cytokines, TNF-α and IL-6, were downregulated by 26±1% and 47±2%, respectively, in Caco-2 monolayers infected with the $lap^-$ strain. Next, we confirmed these observations by using a more sensitive ELISA technique and examined the levels of TNF-α and IL-6 in Caco-2 cells infected with the WT strain or the $lap^-$ strain in conjunction with the ΔinlA and *L. innocua* strains (nonpathogenic *Listeria*). The Caco-2 cells that were infected with the $lap^-$ strain exhibited a significantly attenuated levels of TNF-α (~2.5-fold reduction) and IL-6 (~2-fold reduction) in comparison to the WT strain (FIGS. 3A and 3B). The $lap^-$ strain also displayed a higher attenuation of TNF-α and IL-6 levels than ΔinlA strain. Moreover, Caco-2 cells treated with purified recombinant LAP displayed significantly higher levels of TNF-α and IL-6 production (FIGS. 3A and 3B), without causing any cytopathic or cytotoxic effects as determined using an LDH assay. Analysis of TNF-α and IL-6 protein and mRNA levels in the ileal mucosa of mice also revealed significantly attenuated levels of these cytokines in mice infected with the $lap^-$ strain (FIGS. 3C-3H). Altogether, these data suggest that LAP in *L. monocytogenes* contributed to TNF-α and IL-6 production in Caco-2 cells and the mouse intestinal epithelia, and the decreased production by the $lap^-$ strain suggests a potential role of LAP in in vivo epithelial permeability dysfunction.

Figure 3I:
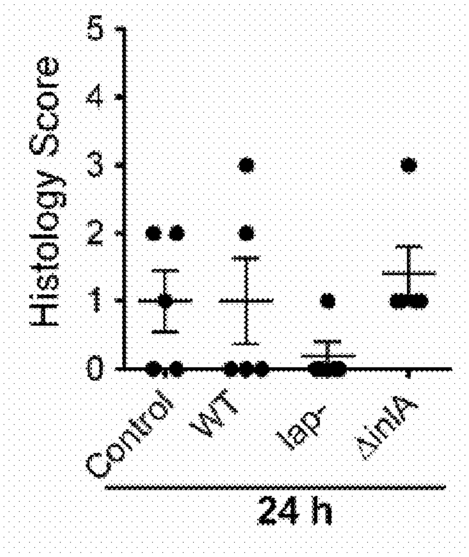
Figure 3J:
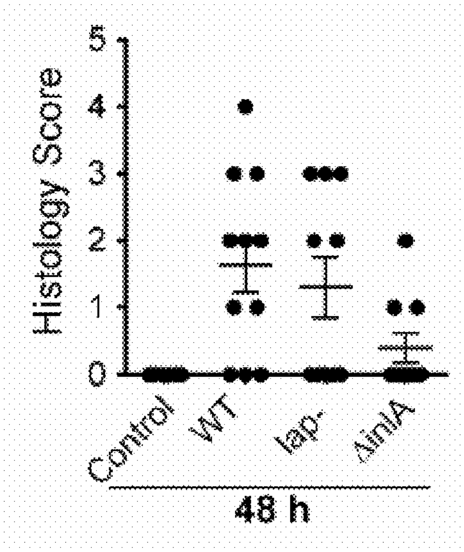
Figure 3K:
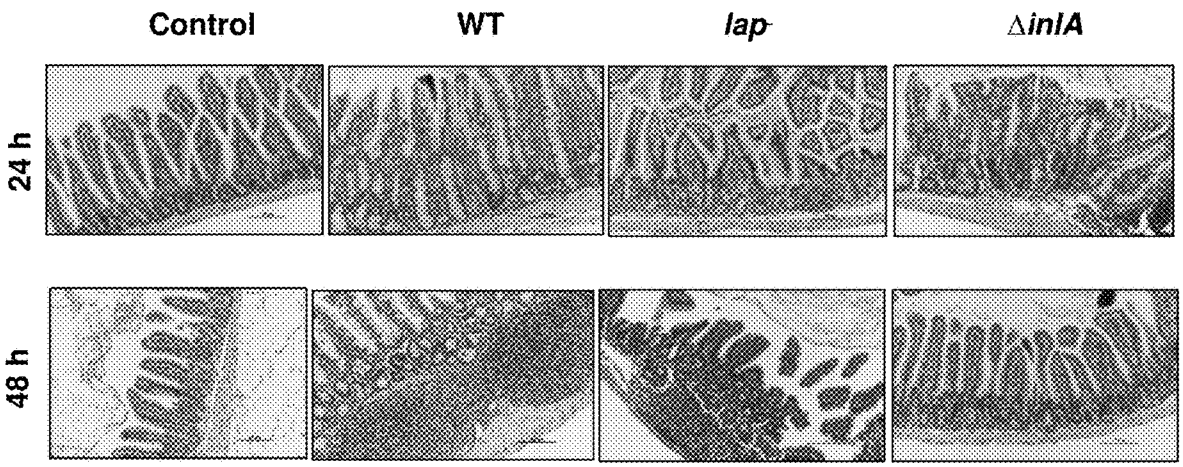

Histopathological analyses of the ileal tissues identified increased numbers of goblet cells in the villous epithelium with numerous neutrophils infiltrating the base of the villous lamina propria in mice challenged with the WT and ΔinlA strains (FIGS. 3I-3K). Differences in intestinal lesions in mice infected with the $lap^-$ strain in comparison to WT or ΔinlA strains were more evident at 24 h pi (FIG. 3I). Notably, ileal tissues of mice infected with the $lap^-$ strain displayed inflammation always located adjacent to and often infiltrating submucosal Peyer's patches (FIG. 3K). Only one specimen exhibited neutrophils that infiltrated beyond the villi immediately adjacent to Peyer's patches (FIG. 3K). Collectively, these data suggest that LAP-mediated epithelial TNF-α and IL-6 production in the early stage of infection (24-48 h) causes mild inflammation without overt histopathological changes, similar to a previous observation.

Figure 4A:
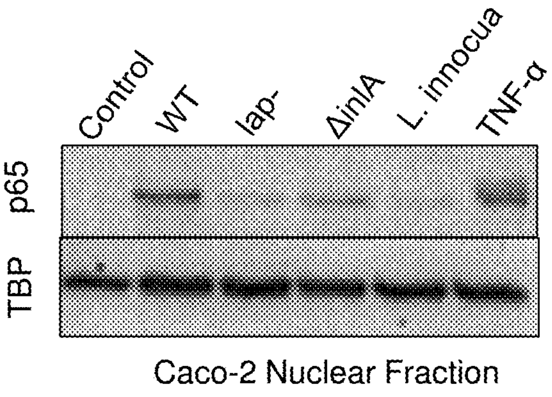
FIGS. 4A-4L show that LAP contributes to *Listeria*-induced NF-κB activation, promotes IκBα degradation, and causes rapid NF-κB(p65) nuclear translocation.
Figure 4B:
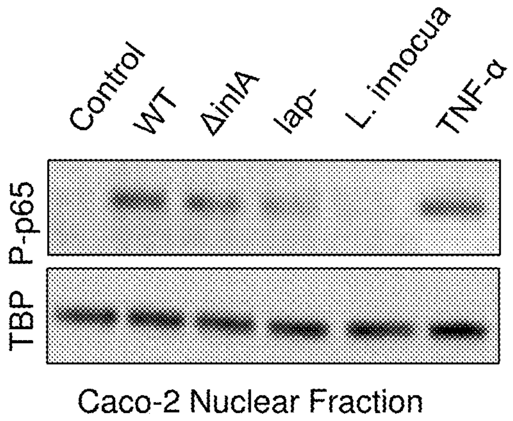
Figure 4C:
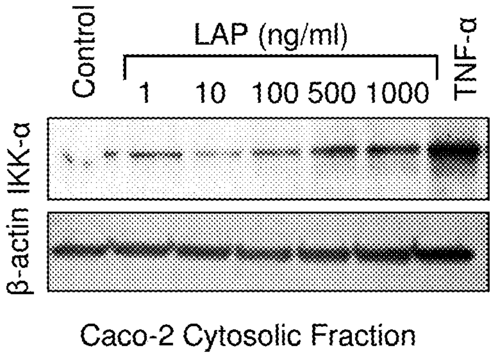
Figure 4D:
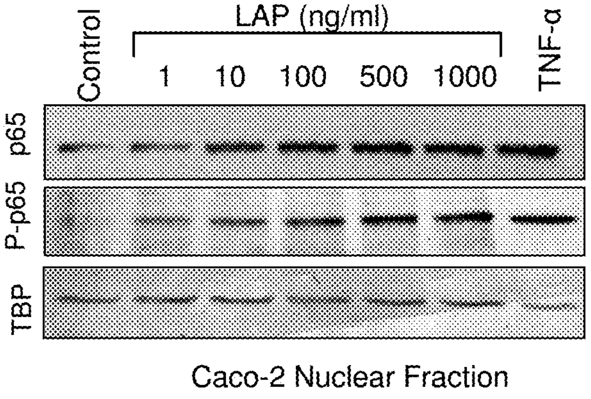

LAP contributes to *Listeria*-induced NF-κB activation and promotes IκBα degradation and nuclear translocation of NF-κB(p65). NF-κB is a central regulator of pro-inflammatory cytokines, including TNF-α and IL-6, and it is strongly activated in Caco-2 cells upon *L. monocytogenes* infection independent of invasion. Moreover, TNF-α induced epithelial permeability also requires NF-κB activation (Ma, T Y, et al., 2004). To investigate whether LAP contributes to NF-κB activation, we measured the nuclear abundance of p65 and its phosphorylation at Ser536 (P-p65) in Caco-2 cells. We observed significantly lower levels of nuclear p65 and P-p65 in the $lap^-$ infected cells relative to the WT (130±10% and 100±3% reduction, respectively) or ΔinlA (120±24% and 70±11% reduction, respectively) infected cells at 30 min pi (FIGS. 4A and 4B). The total cellular p65 was not affected in the WT, $lap^-$ or ΔinlA infected cells. Next, we determined the dose-response of purified recombinant LAP on NF-κB activation. Relative to untreated cells, LAP treatment (1 μg/mL) activated IKKα (267±7% increase) in the cytosol, p65, and P-p65 (218±32% and 120±23% increase, respectively) in the nucleus in a concentration-dependent manner (FIGS. 4C and 4D). These results demonstrate that LAP contributes to *Listeria*-induced NF-κB activation in Caco-2 cells.

Figure 4E:
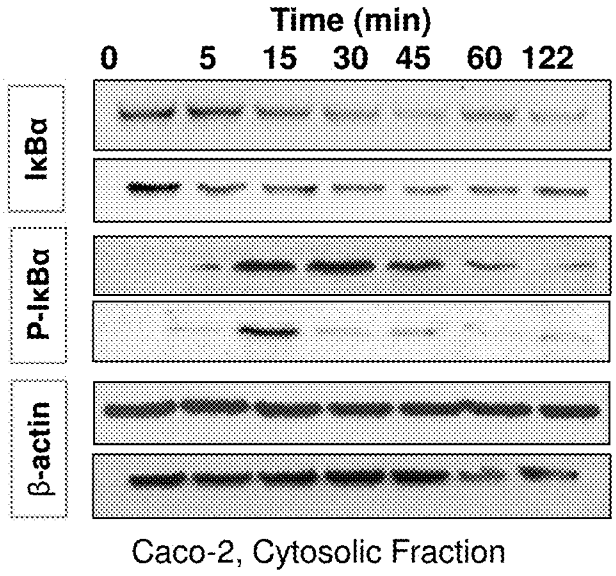
Figure 4F:
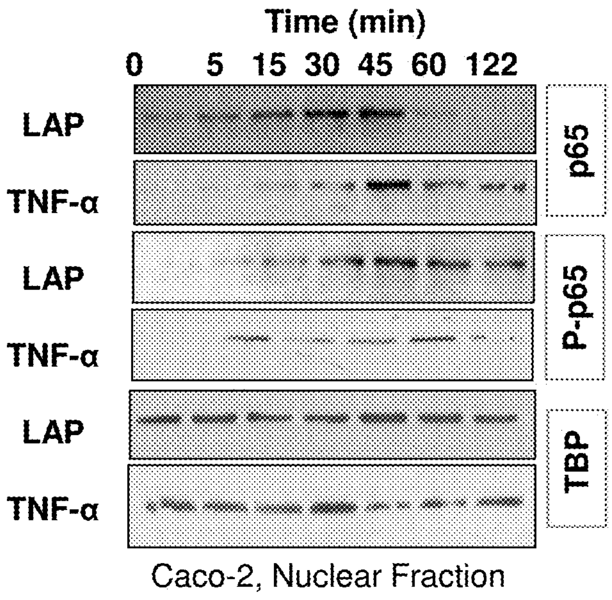
Figure 4G:
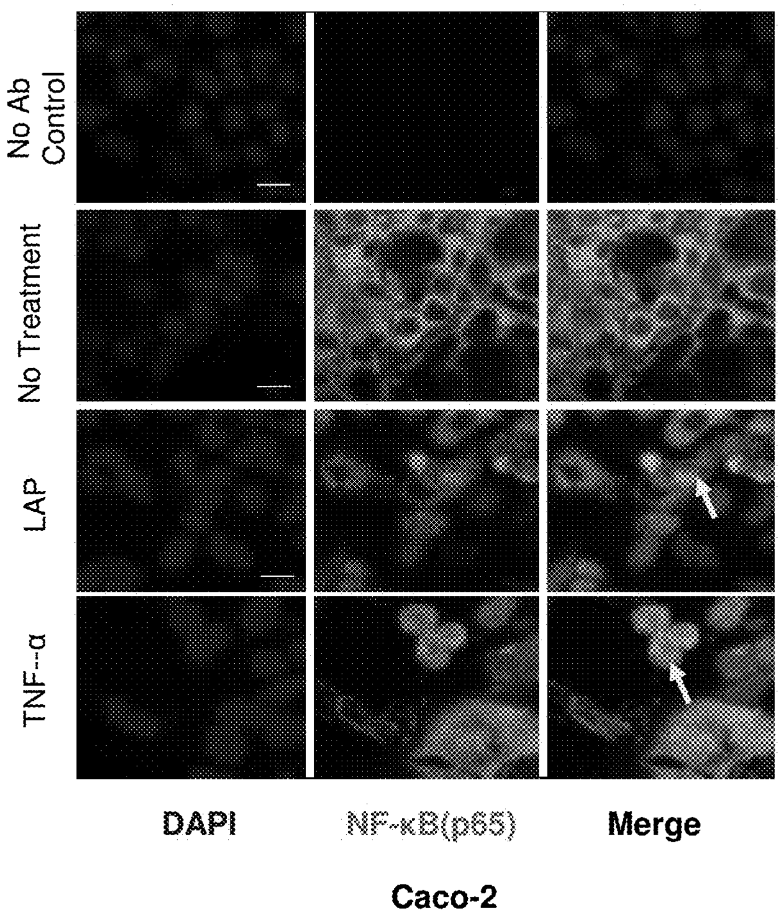
Figure 4H:
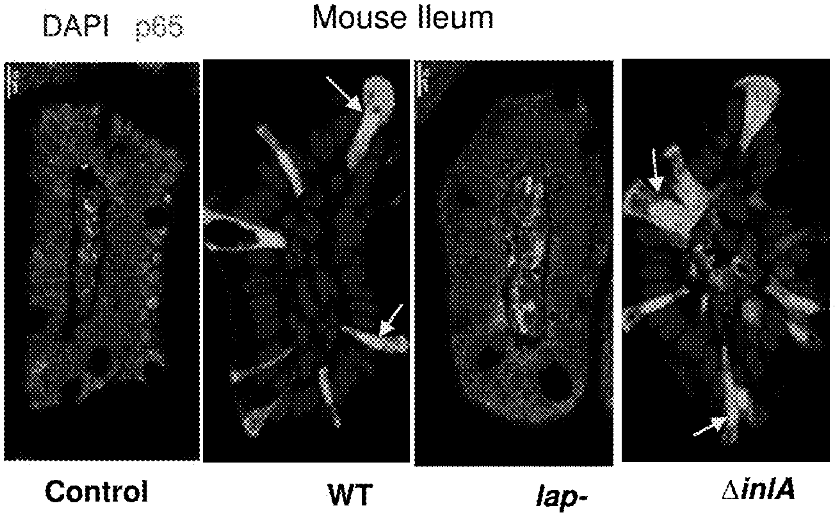
Figure 4I:
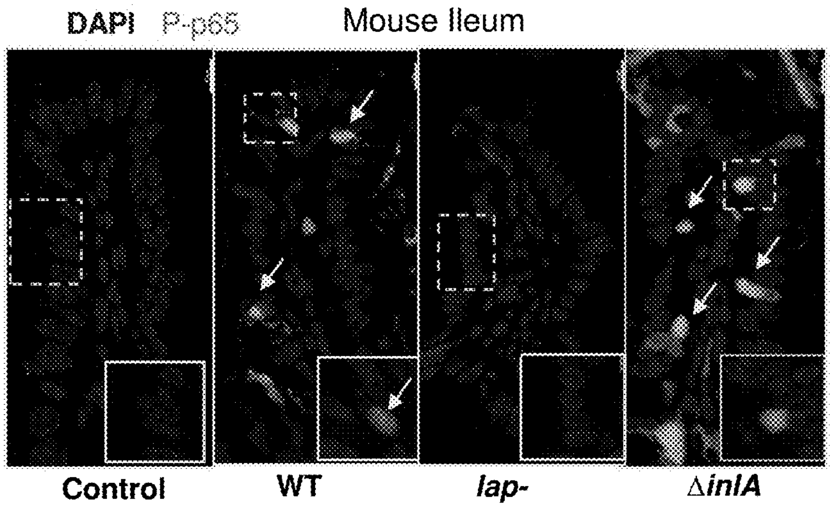
Figure 4J:
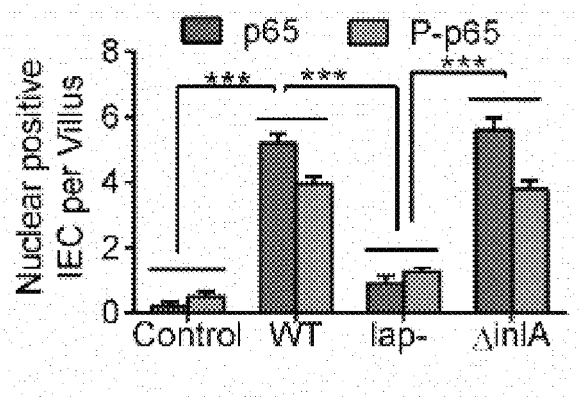

NF-κB is inactive in unstimulated cells and remains associated with the inhibitors of κB (IκB, IκBα and IκBβ) in the cytoplasm. Thus, we determined the kinetics of IκBα degradation in LAP-treated Caco-2 cells. LAP produced a rapid degradation of IκBα within 15 min and that most IκBα was degraded within 45 min (FIG. 4E). The appearance of cytoplasmic phospho-IκBα (Ser32) (P-IκBα) was concomitantly observed at 15 min (FIG. 4E). The degradation of IκBα paralleled with a significant increase in nuclear p65 and P-p65 at 30 min pi compared to untreated cells (FIG. 4F). Purified human TNF-α exhibited similar IκBα degradation kinetics, with P-IκB—a appearing at 15 min and a concomitant increase in nuclear p65 and P-p65 appearing at 30 min (FIGS. 4E and 4F). These results were consistent with confocal microscopic observations, where p65 was sequestered in the cytoplasm of the control cells and in the nucleus after 30 min of LAP or TNF-α treatment (FIG. 4G). These data clearly demonstrate that LAP-treatment in Caco-2 cells stimulated the degradation of IκBα and facilitated rapid translocation of p65 to the nucleus, which is a hallmark of NF-κB activation. To investigate whether LAP contributed to NF-κB activation in mice, we determined the p65 and P-p65 levels in the ileal mucosa by immunostaining. Mice infected with the WT or ΔinlA strain exhibited increased basal NF-κB activity in intestinal epithelial cells (IECs), as determined by the nuclear abundance of p65 and P-p65 (FIGS. 4H-4J). In contrast, a trace amount of nuclear positive p65 and P-p65 epithelial cells was found in the ileal mucosa and most of the p65 was sequestered in the cytoplasm of the intestinal epithelial cells in mice infected with the $lap^-$ strain.

NF-κB/Rel pathways are the most dominant host responses in macrophages that are the major resident cells in the lamina propria; therefore, we examined the ability of LAP to activate NF-κB in the murine macrophage RAW 264.7-NF-κB-luciferase reporter cell line for further verification. Treatment of RAW 264.7 cells with purified LAP lead to NF-κB activation in a concentration-dependent manner. Likewise, purified recombinant InlB protein activated NF-κB in RAW 264.7 cells, but InlA was neutral. LPS as a positive control was a strong NF-κB activator. Heat treatment (100° C., 10 min) abolished the NF-κB activation ability, and polymyxin-B treatment retained the NF-κB activation ability of LAP and InlB. Similarly, proteinase-K treatment abolished LAP and InlB activities, which confirmed their abilities to activate NF-κB but InlA was neutral. These results indicated that LAP and InlB were susceptible to thermal denaturation, and LPS was heat-resistant. Further, the recombinant LAP and InlB preparations were free of LPS contamination. Pretreatment of LAP with an anti-LAP mAb significantly reduced LAP-mediated NF-κB response. Taken together, these results suggest that LAP activates NF-κB in Caco-2 cells, the ileal mucosa of mice and murine macrophage cell lines, while InlA is unresponsive. InlB does not activate NF-κB in epithelial cell lines (Caco-2, HeLa, Hep G2, LoVo), however, it activates NF-κB in macrophage. Likewise, among the other *Listeria* virulence proteins, LLO activated NF-κB in HEK293 cell line and in endothelial cells of transgenic mice, while InlC interfered with NF-κB activation in macrophages.

Figure 4K:
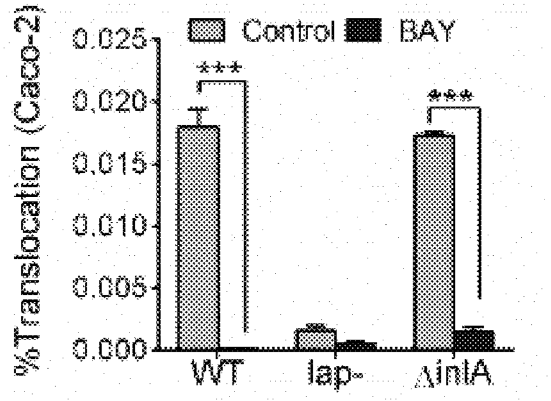
Figure 4L:
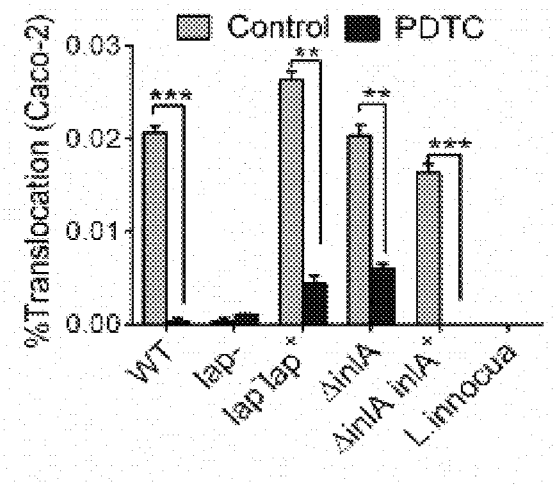

We next examined whether LAP-mediated epithelial permeability could be prevented by pretreatment of Caco-2 cells with the pharmacological NF-κB inhibitors, BAY 11-7085 (BAY) or pyrrolidine dithiocarbamate (PDTC). Treatment of Caco-2 cells with BAY or PDTC inhibited LAP-mediated NF-κB activation and restored Caco-2 TEER. Furthermore, pretreatment with BAY or PDTC significantly reduced the translocation abilities of WT and the isogenic ΔinlA strains across Caco-2 monolayers grown on transwell inserts by 80-90%, but no apparent effect on the lap strain (FIGS. 4K and 4L). Both inhibitors independently did not affect Caco-2 TEER. Importantly, treatment with BAY or PDTC did not affect the intracellular invasion capability of the WT strain in Caco-2 cells. As a positive control, Caco-2 cells were treated with an inhibitor of actin polymerization, cytochalasin D, which blocks *Listeria* invasion and cell-to-cell spread. Cytochalasin D induced a very low TEER and increased the translocation of WT by approximately 2.5-fold despite a low observed invasion. Taken together, these data demonstrate that LAP-mediated NF-κB activation is critical during *L. monocytogenes*-induced epithelial paracellular permeability.

Figure 5A:
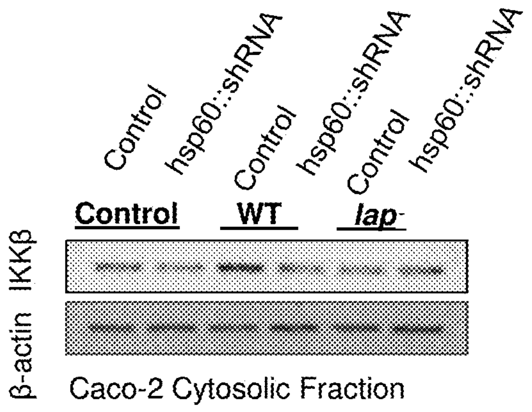
FIGS. 5A-5F show that LAP-induced NF-κB activation is Hsp60 receptor dependent.
Figure 5A:
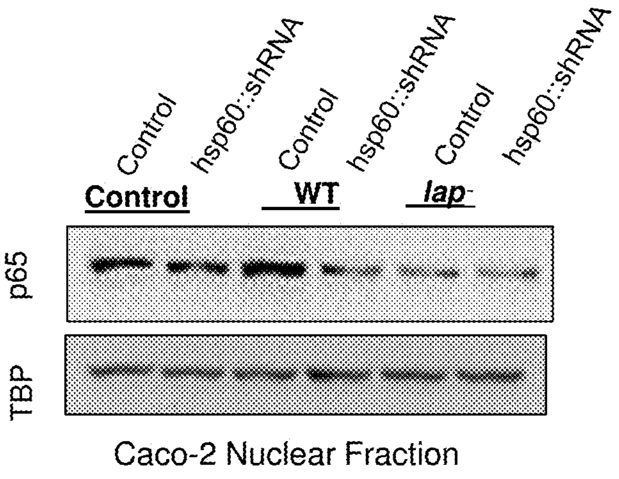
Figure 5B:
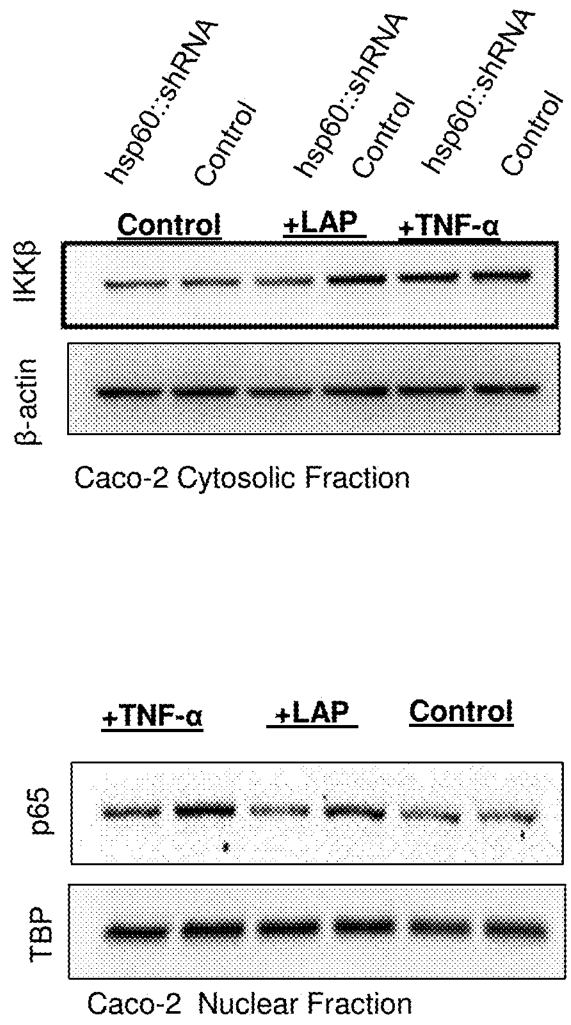
Figure 5C:
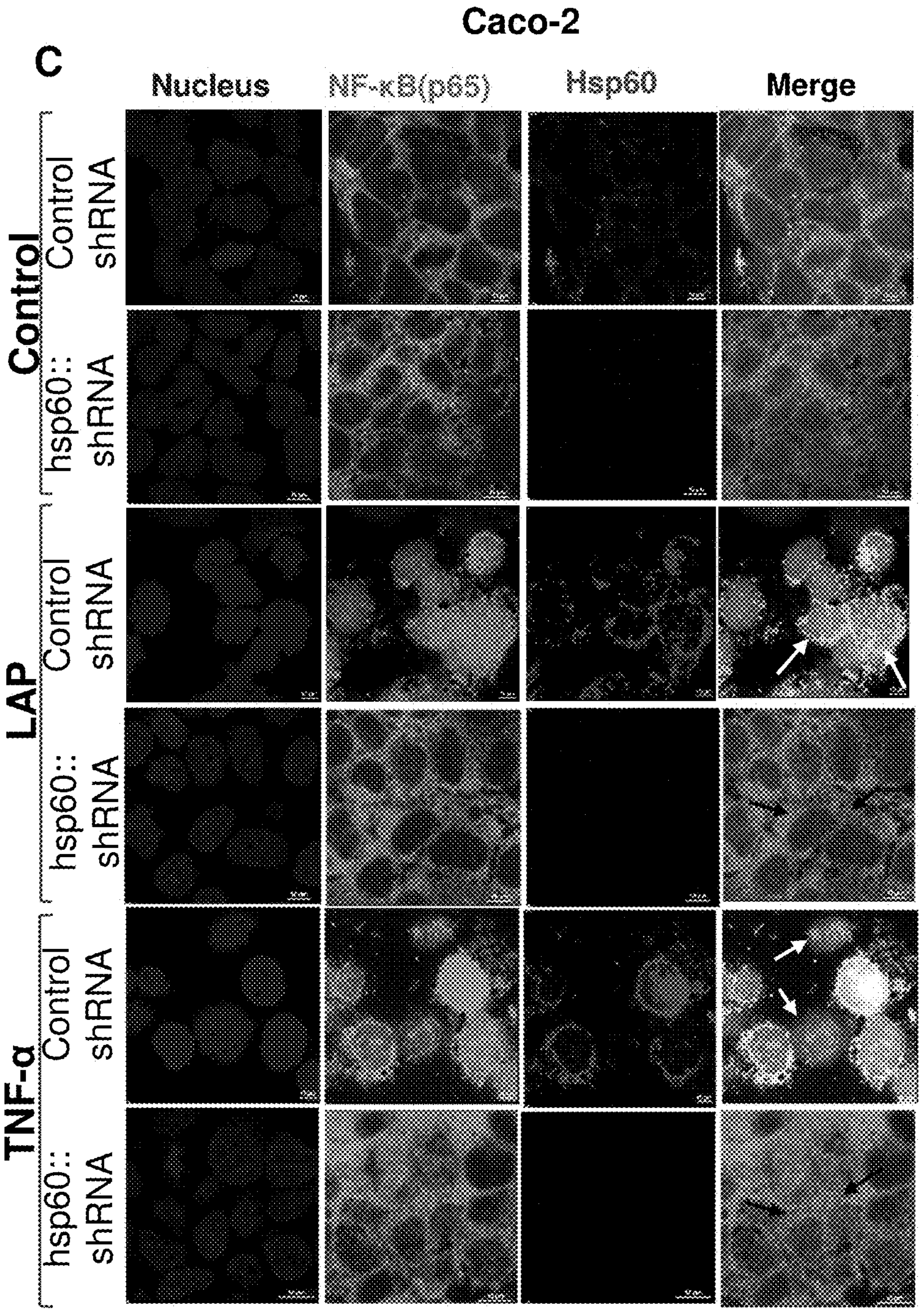
Figure 5D:
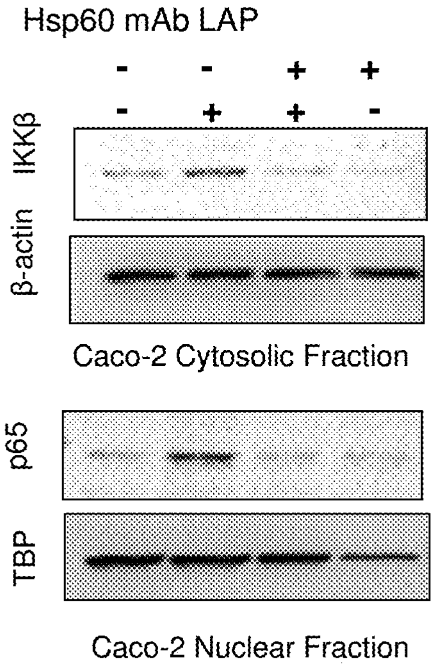

LAP-mediated activation of NF-κB is dependent on the Hsp60 receptor. Researchers have identified Hsp60 as an IKK-interacting protein and suggested that Hsp60 mediates NF-κB-dependent signaling via interaction with IKKα/β in the cytoplasm. To determine the contribution of Hsp60, the receptor for LAP, in *Listeria*-mediated NF-κB activation in Caco-2 cells, we used previously developed Caco-2 cells with Hsp60 knocked-down (hsp60::shRNA, ~70% knockdown) (Burkholder K M, et al., 2010) and determined the levels of IKK-β in the cytoplasmic fraction and p65 in the nuclear fraction in *Listeria*-infected cells. Relative to uninfected shRNA vector control Caco-2 cells, infection with the WT strain significantly increased the protein expression levels of IKK-β (54±8%) and p65 (62±5%) (FIG. 5A). However, the protein expression levels of IKK-β and p65 were significantly decreased in WT-infected Hsp60 knocked-down cells, $lap^-$ strain-infected vector control cells and $lap^-$ strain-infected Hsp60 knocked-down cells (FIG. 5A). Additionally, shRNA vector control cells treated with purified LAP significantly increased protein expression levels of IKK-β (52±8%) and p65 (54±8%) (FIG. 5B). In contrast, Hsp60 knocked-down cells treated with purified LAP displayed basal protein expression levels of IKK-β and p65 (FIG. 5B). Furthermore, confocal microscopy confirmed the nuclear translocation of p65 in shRNA vector control cells treated with LAP, but the Hsp60 knocked-down cells treated with LAP retained p65 within the cytoplasm (FIG. 5C). Notably, TNF-α treatment also produced a slight reduction in the nuclear translocation of p65 in the Hsp60 knocked-down cells (FIG. 5C). To delineate the contribution of membrane-associated Hsp60 in LAP-mediated NF-κB activation, we pretreated Caco-2 monolayers with an anti-Hsp60-specific mAb to neutralize only the surface expressed membrane Hsp60 prior to LAP treatment. Caco-2 cells treated with purified LAP significantly increased protein expression levels of IKK-β (53±2%) and p65 (63±5%) (FIG. 5D). However, pretreatment of Caco-2 cells with anti-Hsp60 mAb prior to LAP treatment, significantly reduced protein expression of IKK-β and p65 to basal levels suggesting that the membrane-associated Hsp60 contributes to LAP-mediated NF-κB activation. Altogether, these data clearly suggest that the LAP (ligand) and Hsp60 (receptor) interaction significantly contributes to *Listeria*-induced NF-κB activation in Caco-2 cells.

Figure 5E:
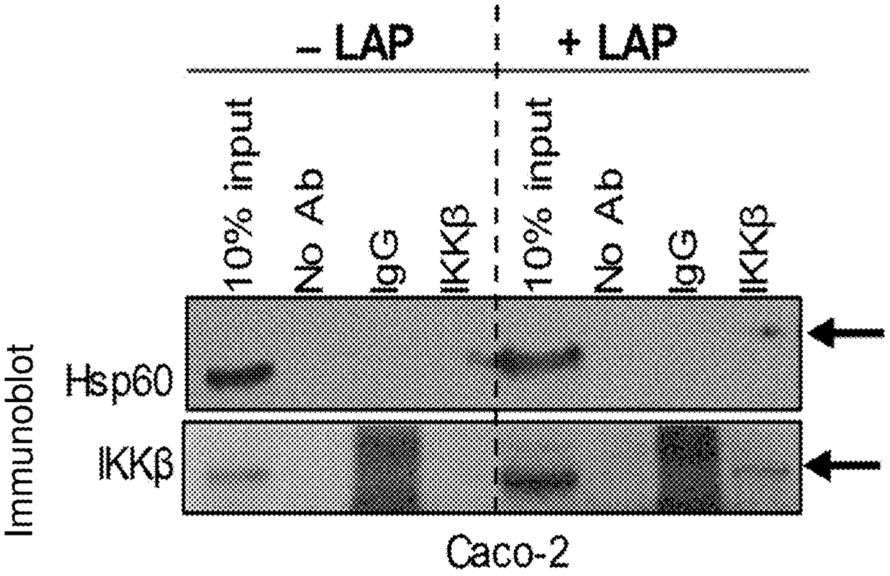
Figure 5F:
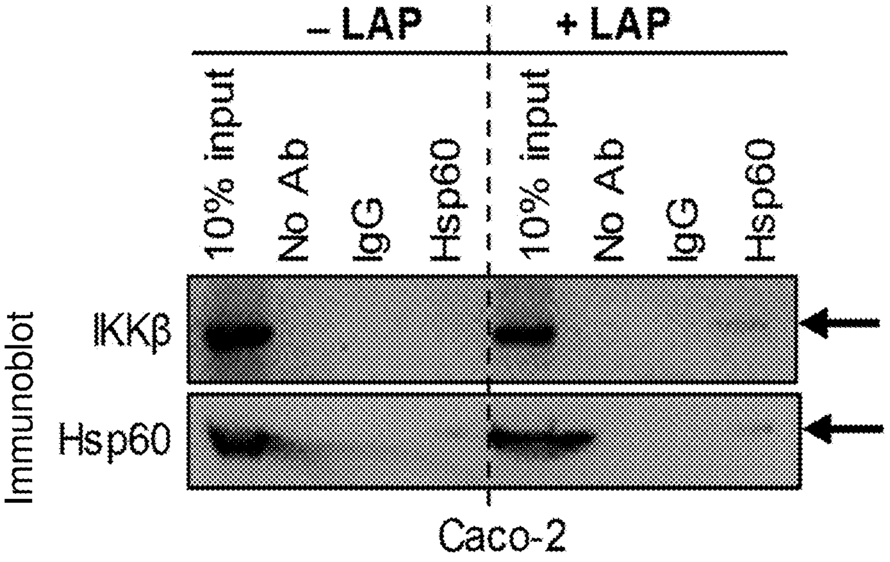

To examine the possible interactions between Hsp60 and IKK in Caco-2 cells, we next immunoprecipitated IKKβ from purified LAP-treated or -untreated Caco-2 cell lysates using an anti-IKKβ antibody and immunoblotted these lysates with anti-IKKβ and anti-Hsp60 antibodies. The immunoblots confirmed precipitation of IKKβ (FIG. 5E). Immunoblotting the lysates with an anti-Hsp60 mAb resulted in Hsp60 co-precipitation in LAP-treated cells but not in cells that used the rabbit IgG isotype as a control (FIG. 5E, arrows). Reverse immunoprecipitation using an anti-Hsp60 antibody also co-precipitated IKK-β and Hsp60 in the LAP-treated cells (FIG. 5F, arrows). These data suggest that Hsp60 ultimately resides in the IKK complex in LAP-treated Caco-2 cells.

Figure 6A:
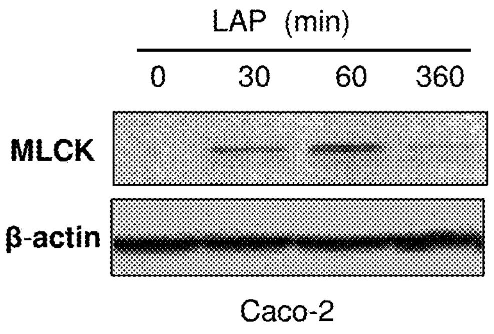
FIGS. 6A-6H demonstrate that LAP promotes cell-cell junctional protein dysregulation through MLCK activation.
Figure 6B:
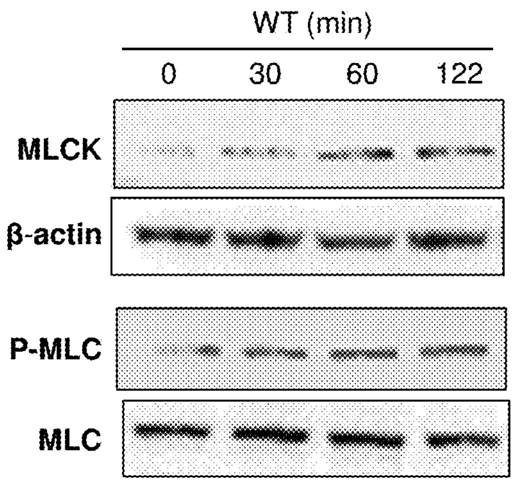

LAP promotes junctional protein dysregulation for paracellular permeability and *L. monocytogenes* translocation. Several groups have shown that MLCK phosphorylates myosin II regulatory light chain (MLC) which regulates paracellular permeability via cytoskeleton rearrangement, and modulates TJ protein expression. Pro-inflammatory cytokines, such as TNF-α and IL-10, induce tight junction dysfunction via activation of MLCK in cultured epithelial cells and mouse intestine (Ma, T Y, et al., *Am. J. Physiol. Gastrointest. Liver Physiol.* 2005, 288, G422-G430). We observed a time-dependent increase of MLCK protein expression levels (249±9%; 60 min pi) in Caco-2 cells treated with purified LAP (FIG. 6A). Likewise, *L. monocytogenes* WT infection also significantly increased MLCK and P-MLC protein expression levels in Caco-2 cells (184±26% and 134±12%, respectively; 60 min pi) (FIG. 6B). Next, we used detergent solubility-based cell fractionation to analyze the time-dependent distribution of TJ (claudin-1, occludin, ZO-1) and AJ (E-cadherin and β-catenin) proteins in the detergent-insoluble and detergent-soluble fractions from Caco-2 cells infected with the WT strain. Relative to uninfected cells, we observed a significant decrease in occludin and claudin-1 (40±8% and 50±10%, respectively) protein expression levels in the detergent-insoluble fractions at 45 min pi and concomitant increase (74±8% and 40±10%, respectively) in the expression of these proteins in the detergent-soluble fraction at 120 min pi. Notably, the expression of E-cadherin was also significantly decreased (60±8%) in the detergent-insoluble fraction at 45 min pi, while the expression of ZO-1 and β-catenin did not change significantly in the detergent-insoluble fraction.

Figure 6C:
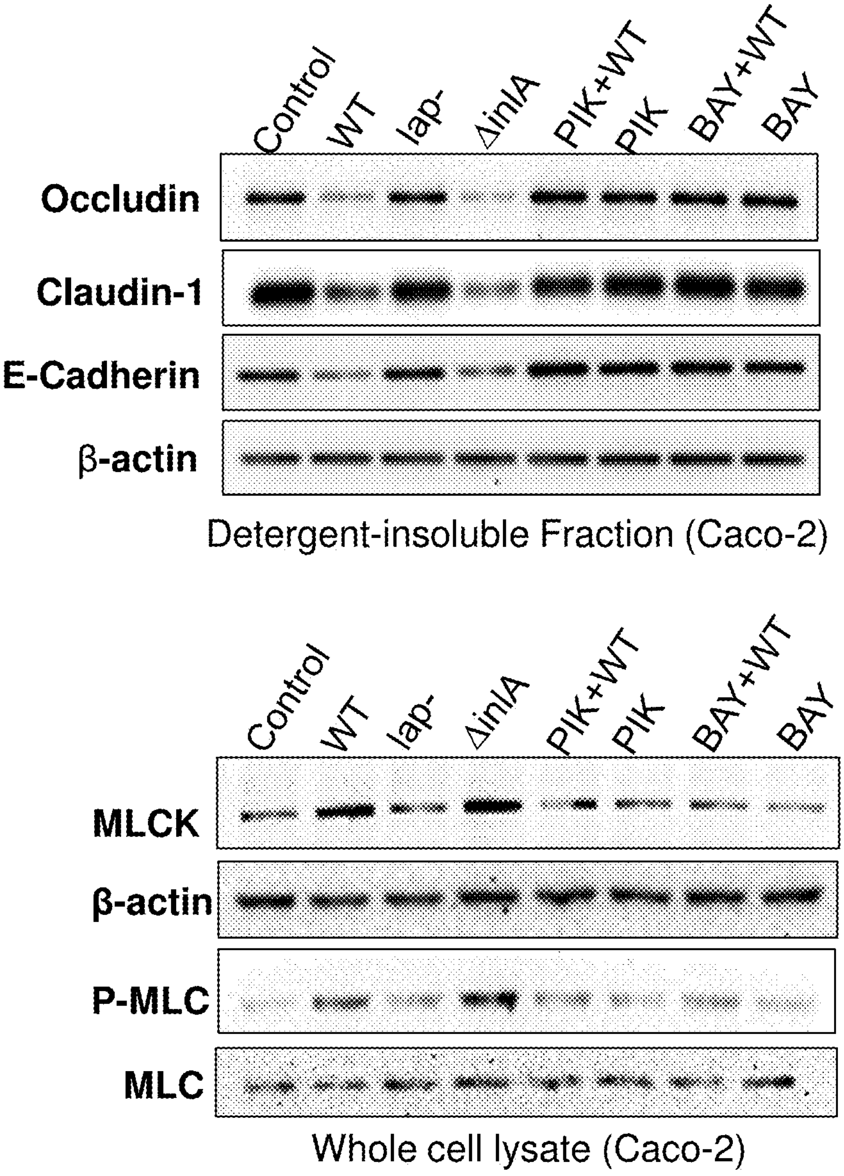

To determine the contribution of LAP in the regulation of TJ and AJ proteins, we analyzed the levels of cell junction proteins in the detergent-insoluble fractions of Caco-2 cells infected with the WT, $lap^-$ or the ΔinlA strains at 45 min pi. Relative to uninfected cells, Caco-2 cells infected with the WT or the ΔinlA strains showed significantly decreased protein expression levels of occludin (65±3%) and claudin-1 (70±5%) in the detergent-insoluble fraction (FIG. 6C) and significantly increased total cellular MLCK (270±21%) and P-MLC (218±17%) protein levels (FIG. 6C). In contrast, the expression levels of these proteins were similar to uninfected Caco-2 control cells that were infected with the lap-strain. These data suggest that LAP contributes to the sub-cellular redistribution of occludin and claudin-1, and increased expression of MLCK and P-MLC in Caco-2 cells. Notably, E-cadherin expression was significantly reduced (87±3%) in the detergent-insoluble fraction of Caco-2 cells infected with the WT strain in comparison to uninfected control cells, but E-cadherin levels were maintained similarly in the detergent-insoluble fraction in cells infected with the lap$^-$ or the ΔinlA strain (FIG. 6C). These results suggest that LAP contributes to E-cadherin redistribution and that direct interaction between InlA and E-cadherin also contributes to E-cadherin internalization in Caco-2 cells. These observations are consistent with a previous report that purified InlA induced internalization of E-cadherin in Jeg-3 cells.

Figure 6D:
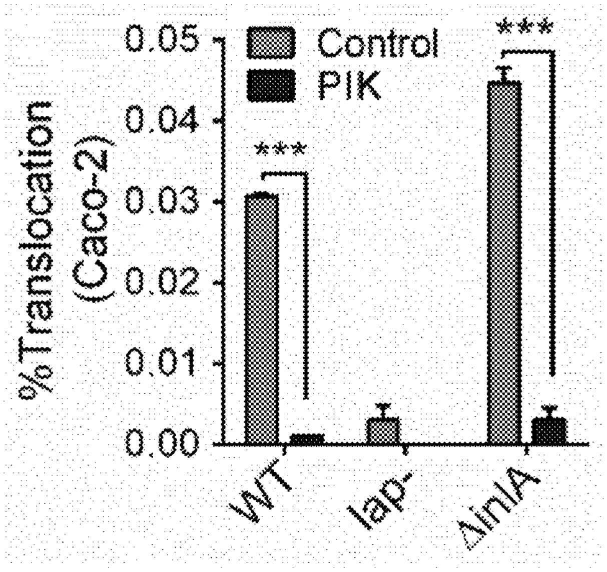
Figure 6E:
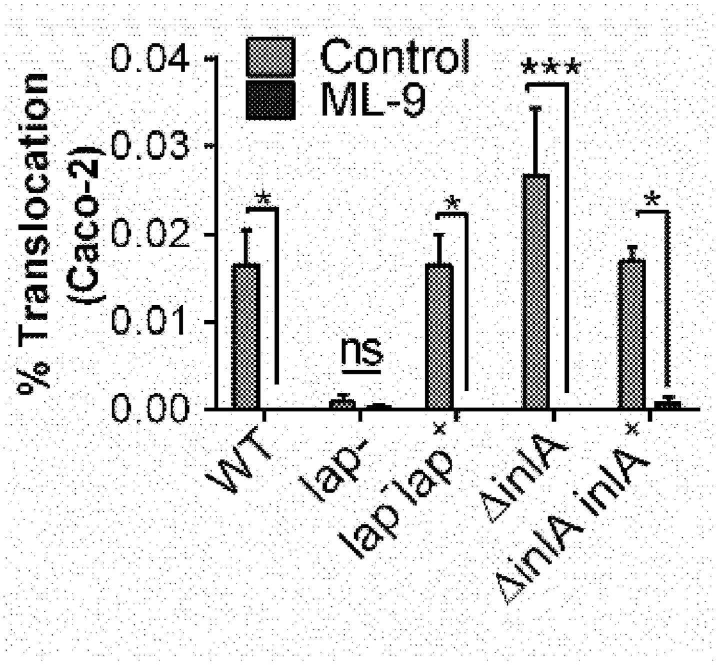

We next examined whether LAP-mediated loss of junctional proteins was prevented by the addition of the NF-κB inhibitor, BAY or the MLCK inhibitor, PIK (permeant peptide inhibitor kinase) (Zolotarevsky, Y, et al., *Gastroenterology,* 2002, 123, 163-172) in Caco-2 cells. Pharmacological inhibition of NF-κB or MLCK prevented *L. monocytogenes*-induced redistribution of occludin, claudin-1, and E-cadherin, while these inhibitors independently had no effect on the expression of these junctional proteins (FIG. 6C) or Caco-2 TEER values (FIG. 3N). Additionally, consistent with our observations with the NF-κB inhibitors, BAY and PDTC (FIGS. 3K and 3L), the MLCK inhibitors, PIK and ML-9 significantly reduced the translocation competencies of WT and ΔinlA strains across the Caco-2 cell barrier (FIGS. 6D and 6E). Most importantly, none of these inhibitors, affected the intracellular invasion capabilities of the WT strain suggesting that the reduction in the translocation competencies of *L. monocytogenes* across the Caco-2 cell barrier by pharmacological inhibition of MLCK was not due to decreased intracellular invasion.

Figure 6F:
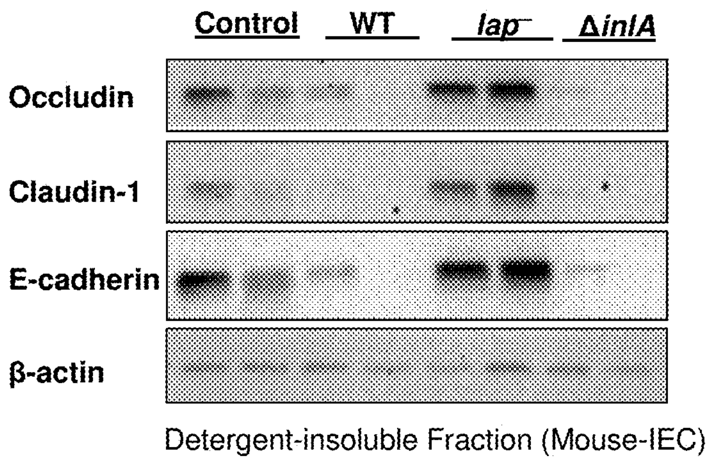
Figure 6G:
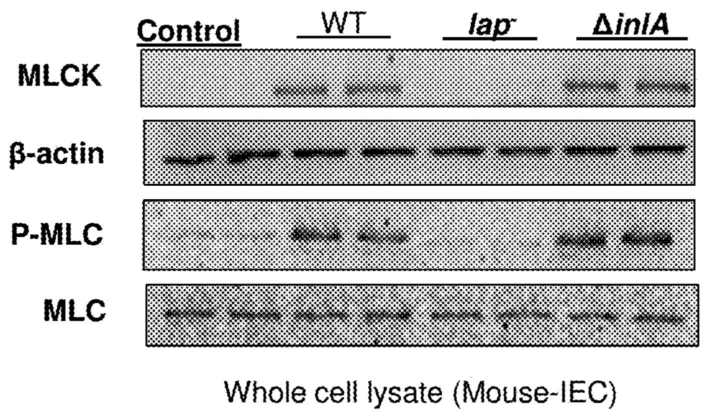
Figure 6H:
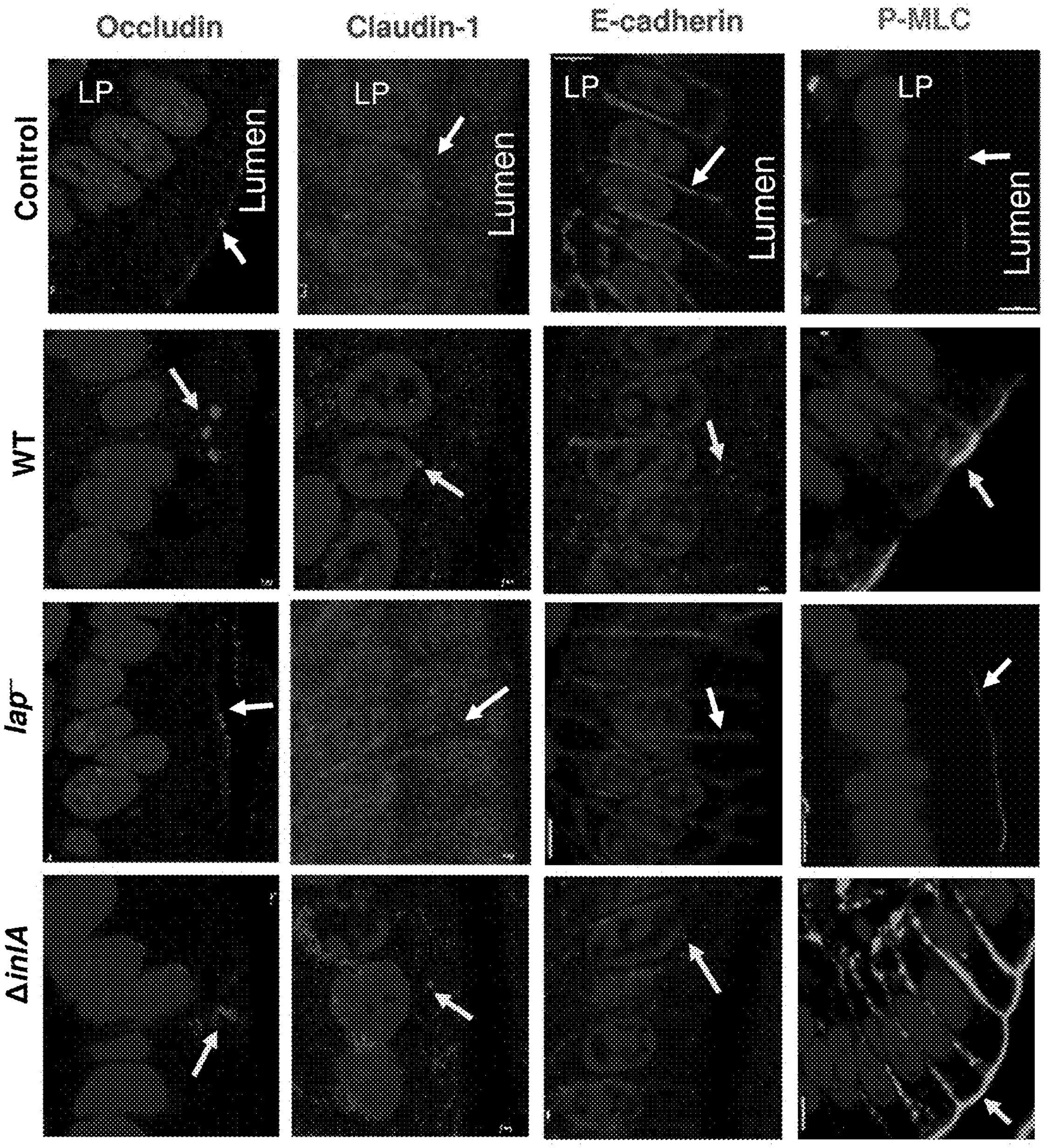

(IV) Examination of ileal epithelial cells of mice revealed significantly reduced protein expression levels of occludin (48±8%), claudin-1 (37±2%), and E-cadherin (68±10%) in the detergent-insoluble fractions (FIG. 6F) and significantly increased expression levels of total cellular MLCK (660±100%) and P-MLC (280±48%) (FIG. 6G) in mice challenged with the WT and ΔinlA strains, but not in mice challenged with the lap$^-$ strain. Immunofluorescence staining of the ileal tissue sections also confirmed membrane mislocalization of occludin, claudin-1, and E-cadherin and increased expression of P-MLC in mice challenged with the WT and ΔinlA strains, but not by the lap$^-$ strain (FIG. 6H). Collectively, these results suggest that LAP promoted enhanced MLCK levels, causing MLCK-mediated phosphorylation of MLC, which in turn induced MLCK-triggered opening of the TJ barrier via cellular redistribution (mislocalization) of occludin, claudin-1, and E-cadherin.

Figure 7A:
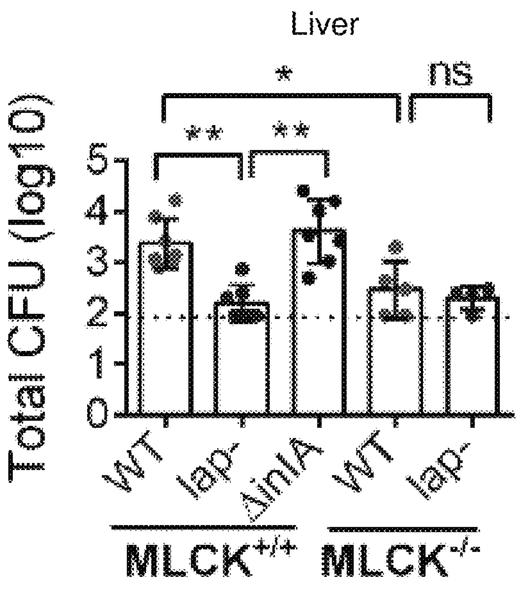
FIGS. 7A-7J demonstrate that *Listeria monocytogenes* translocation and epithelial permeability are affected in MLCK knockout mice.
Figure 7B:
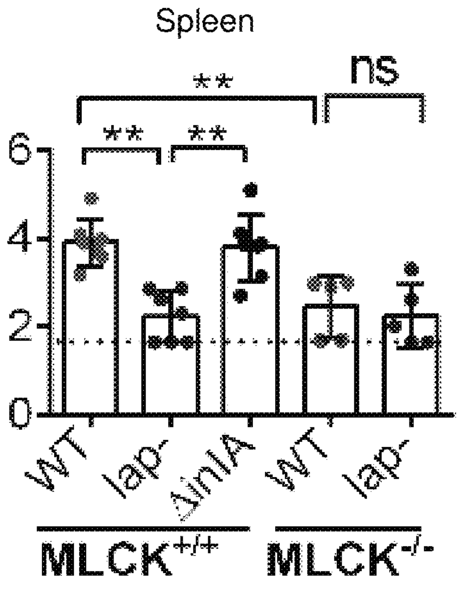
Figure 7C:
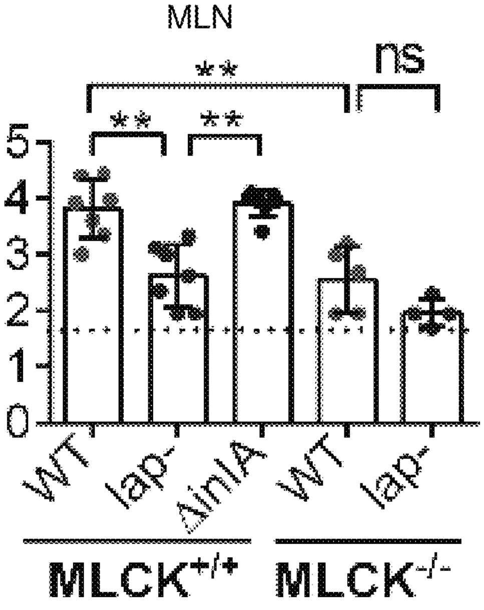
Figure 7D:
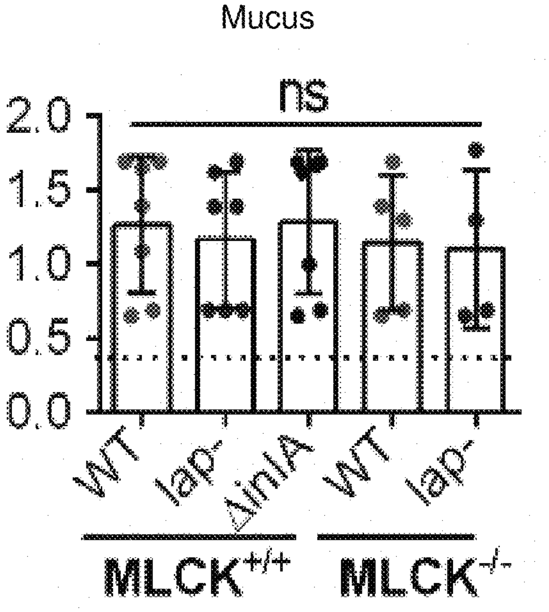
Figure 7E:
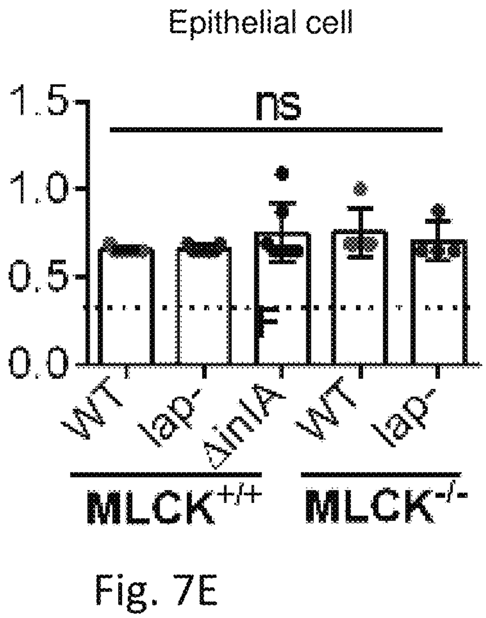
Figure 7F:
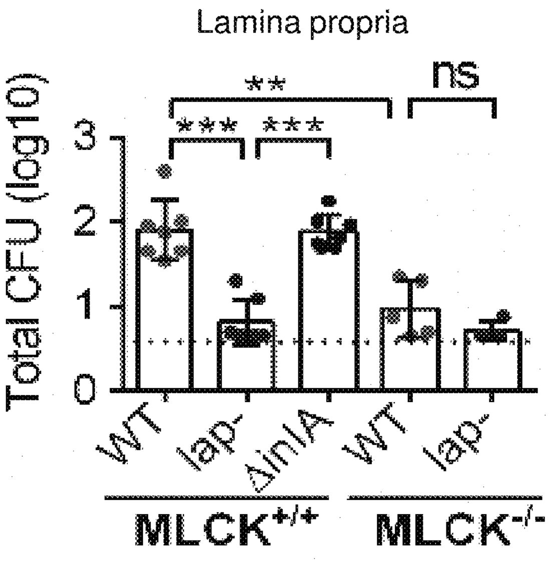
Figure 7G:
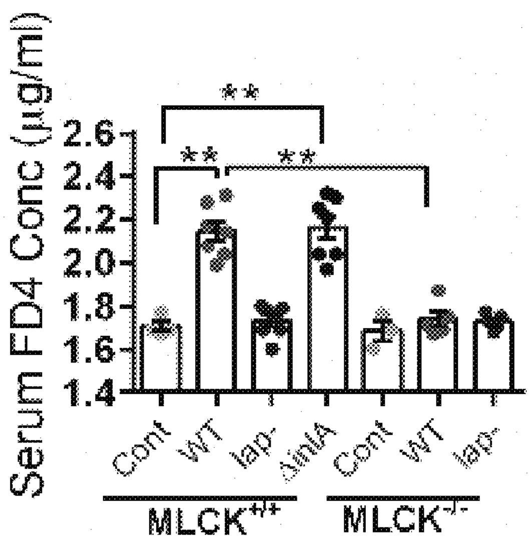
Figure 7H:
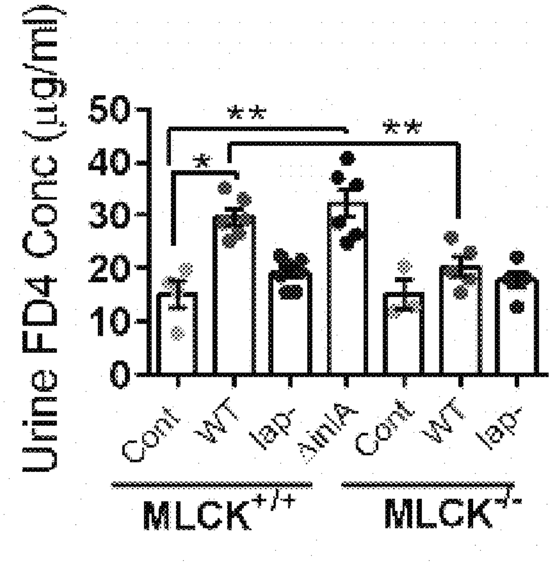
Figure 7I:
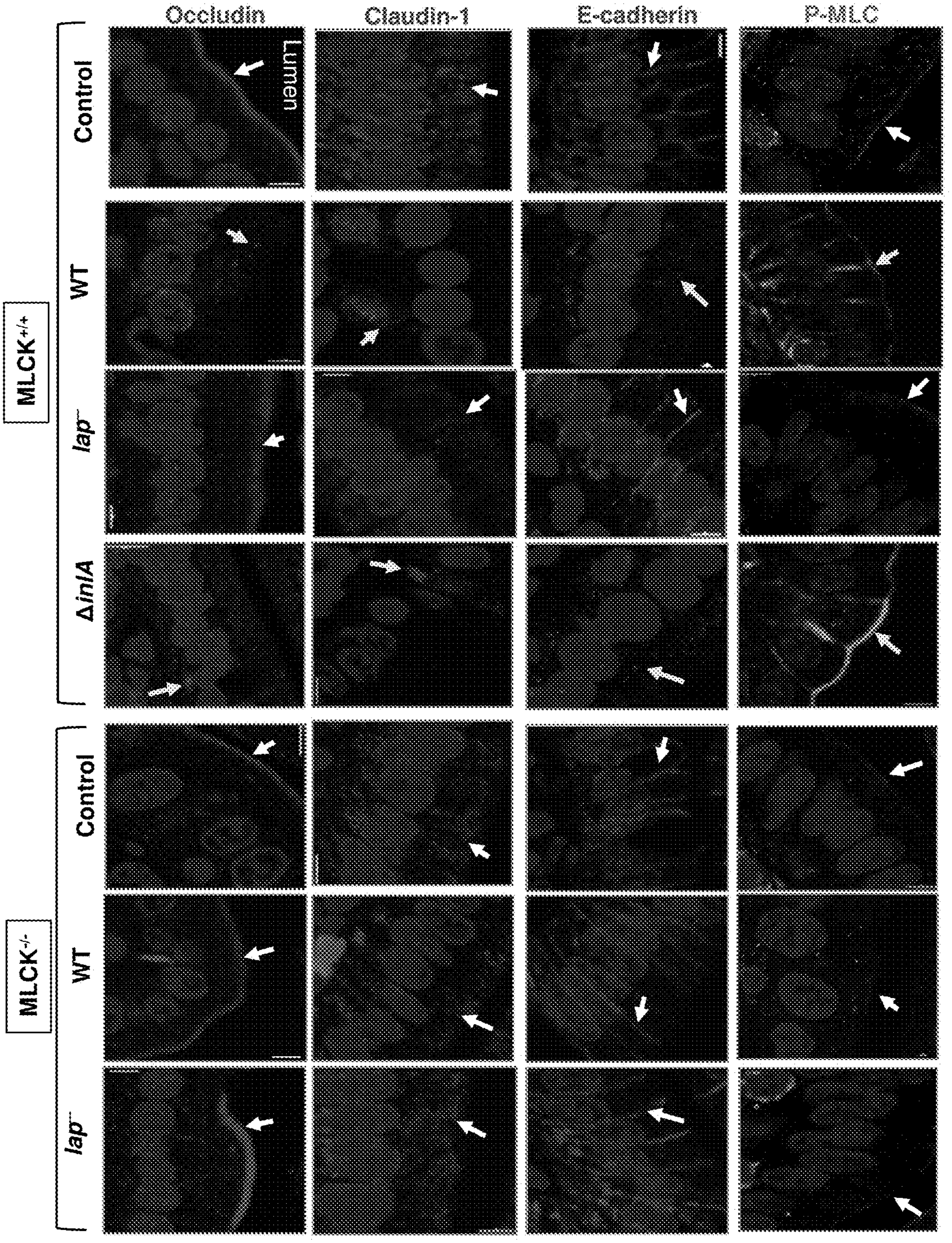
Figure 7J:
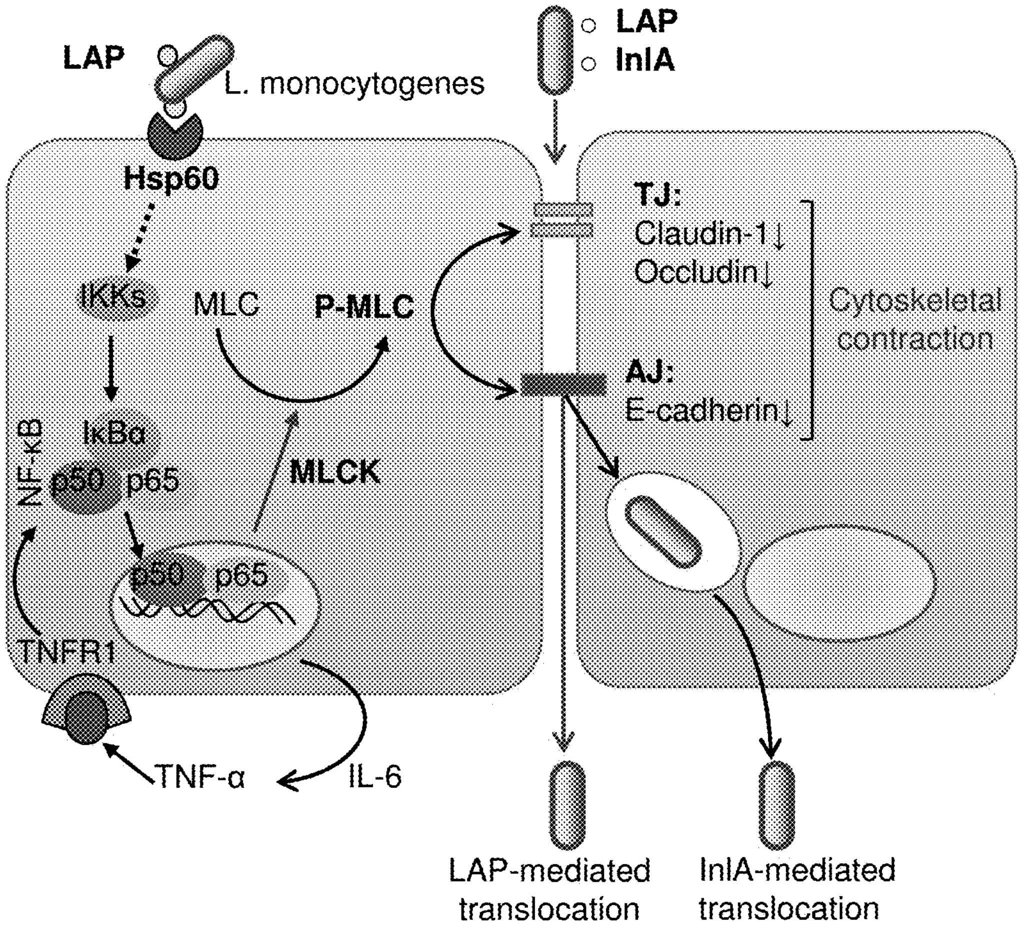

*Listeria monocytogenes* translocation and epithelial permeability are affected in MLCK knockout mice. To evaluate the role of MLCK in the mechanism of *L. monocytogenes* induced epithelial permeability, we orally challenged MLCK knockout mice lacking the 210-kDa long chain (MLCK$^{-/-}$) and its parental strain (C57BL/6 mice, MLCK$^{+/+}$) with WT, lap$^-$ or the ΔinlA strains. *Listeria* counts were enumerated in the extra-intestinal sites at 48 h pi. The bacterial burden in the liver, spleen and the MLN of the MLCK$^{+/+}$ mice challenged with the lap$^-$ strain or the MLCK$^{-/-}$ mice challenged with either the WT or the lap$^-$ strain were significantly reduced (~1.5-2.0 log) than those in the same tissues of the MLCK$^{+/+}$ mice that were challenged with WT or the ΔinlA strain (FIGS. 7A-7C). Next, we enumerated bacteria in the mucus, epithelial cells, and in the underlying lamina propria of ileal mucosa. Similar counts of WT, lap$^-$ or ΔinlA mutant strains were recovered from the mucus fraction and epithelial cells in both MLCK$^{+/+}$ and MLCK$^{-/-}$ mice (FIGS. 7D and 7E) suggesting that the epithelial intracellular invasion of *L. monocytogenes* was not affected in MLCK$^{-/-}$ mice. As expected, lap strain had significantly reduced counts in lamina propria (~1.0 log), compared to the WT or ΔinlA mutant strain in MLCK$^{+/+}$ mice; however, both lap$^-$ and WT strain showed similar but significantly reduced translocation to the lamina propria in MLCK$^{-/-}$ mice relative to MLCK$^{-/-}$ mice (FIG. 7F). These data suggest that *L. monocytogenes* in the MLCK$^{+/+}$ mice exhibited a defect in translocating from the ileal mucosa to the underlying lamina propria and systemic dissemination possibly due to decreased translocation in this mouse strain. To assess whether decreased bacterial translocation correlates with decreased paracellular permeability in MLCK$^{-/-}$ mice, we examined FD4 permeability through the intestinal epithelium. *Listeria*-infected mice that received FD4 orally 4-5 h before sacrifice displayed significantly increased FD4 concentrations approximately 25±8% in the serum and 95±30% in the urine, in WT and ΔinlA-challenged MLCK$^{+/+}$ mice compared to the uninfected control mice (FIGS. 7G and 7H). However, relative to uninfected control mice, FD4 concentrations did not significantly increase in the serum and urine of MLCK$^{+/+}$ mice challenged with the lap$^-$ strain or the MLCK$^{-/-}$ mice challenged with either the WT or the lap$^-$ strain (FIGS. 7G and 7H). Immunofluorescence staining of the ileal tissue sections revealed membrane mis-localization of occludin, claudin-1 and E-cadherin, and increased expression of P-MLC in MLCK$^{-/-}$ mice challenged with the WT and ΔinlA strains, but not in the MLCK$^{+/+}$ mice challenged with the lap$^-$ strain or the MLCK$^{-/-}$ mice challenged with either the WT or lap$^-$ strain (FIG. 7I). Collectively, these results demonstrate that the lap$^-$ strain defect in translocating to the lamina propria is also observed in the C57BL/6 mouse strain (besides A/J strain) and that the MLCK contributes to *Listeria*-induced junctional protein dysregulation in vivo.

We have demonstrated that *Listeria* adhesion protein (LAP, 94 kDa), a bi-functional alcohol acetaldehyde dehydrogenase from *Listeria monocytogenes* or a nonpathogenic *Listeria* binds to host Hsp60 (receptor) and promotes the translocation of *L. monocytogenes* across the intestinal barrier into the lamina propria. LAP (lmo1634) is a moonlighting protein that exhibits adhesion properties in pathogenic *Listeria*. Our results demonstrate that LAP or its peptide derivative binding to Hsp60 directly activates canonical NF-κB signaling, which facilitates myosin light-chain kinase (MLCK)-mediated opening of the intestinal epithelial barrier via the cellular redistribution of the major tight junction (TJ) proteins; claudin-1 and occludin, and adherens junction (AJ) protein, E-cadherin.

Figure 8A:
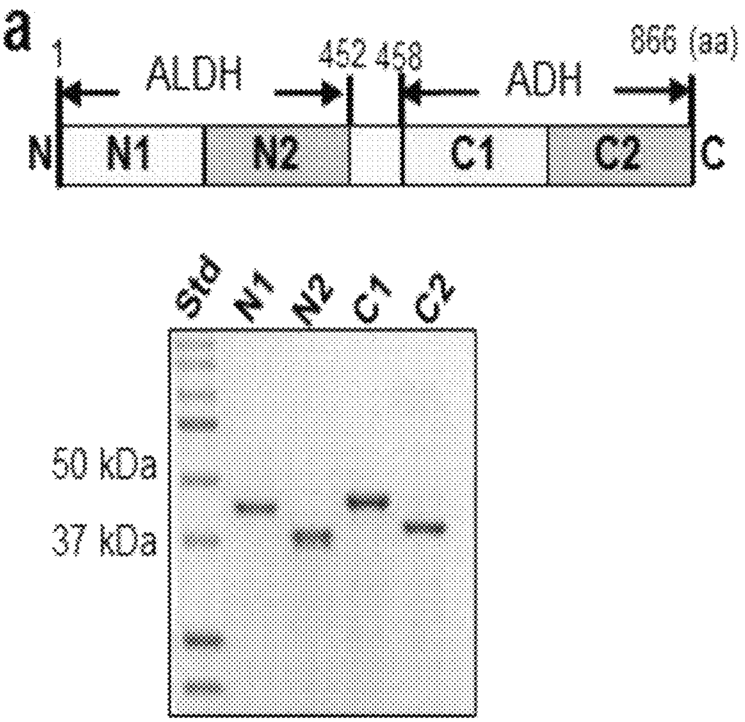
FIGS. 8A-8B show schematic representation and activity of LAP and its domains.
Figure 8B:
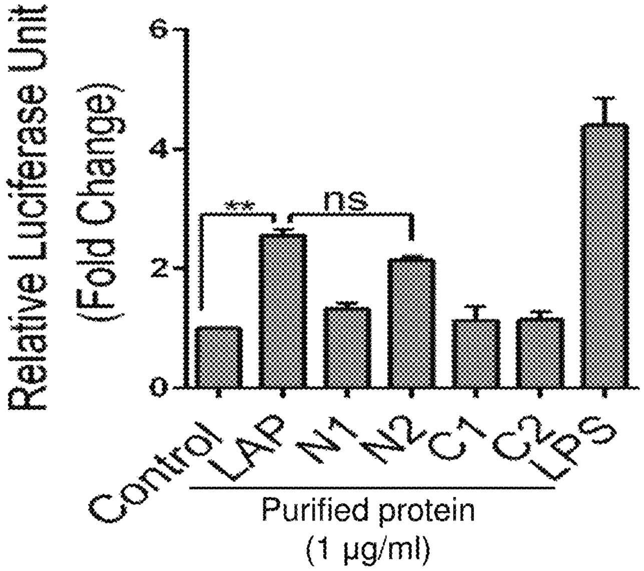

We next tested the LAP domains (peptide fragments—N1, N2, C1, and C2) and full-length LAP preparation devoid of any LPS contaminant for their effects on NF-κB activation in the RAW 264.7-NF-κB-luciferase reporter cell line. Only the N2 domain that interacts with Hsp60 activated NF-κB nearly as effectively as the full-length LAP, while the other domains showed activity similar to the untreated control cells. These results suggest that the N2 domain of LAP, which interacts with Hsp60, play a main role for NF-κB activation and paracellular permeability (see FIGS. 8A, 8B). Collectively, these data suggest that LAP contributes to enhanced intestinal barrier permeability and a peptide derivative (10-20 amino acid) of LAP that interacts with Hsp60 may be suitable for delivering drugs across the mucosal epithelial barrier. FIGS. 8A and 8B show schematic representation and activity of LAP and its domains. (a) (Top) Schematic representation of LAP, an alcohol acetaldehyde dehydrogenase enzyme (AAD; 866 aa) consisting of an N-terminal acetaldehyde dehydrogenase (ALDH) and a C-terminal alcohol dehydrogenase region (ADH). (Bottom)

Purity of recombinant LAP domains; N1, N2, C1 and C2 (2 pig/lane) was determined by SDS-PAGE and Coomassie blue staining. (b) Analysis of NF-κB stimulating ability of LAP domains using RAW 264.7 NF-κB luciferase reporter cell line. Cells were stimulated with LAP, N1, N2, C1 and C2 (1 μg/mL, each) for 6 h and analyzed for luciferase activity. Bars indicate fold induction compared with unstimulated cells and are represented as mean±SEM (n=6). *p<0.05, **p<0.01; and ns: not significant.

Experimental Model and Subject Details

Mice.

A/J mice (female, 8-10 week-old; Jackson Laboratory) that are highly sensitive to oral *L. monocytogenes* challenge were used. The use of A/J mice allowed us to use a $10^8$ CFU (10-fold lesser inoculum) to cause a systemic infection. For experiments with C57BL/6 mice, 6-8 week-old, male or female, wild-type C57BL/6 ($MLCK^{+/+}$), or the 210-kDa $MLCK^{-/-}$ mice, bred in our facility were used. Mice were housed in individual cages, provided ad libitum feed and water, and acclimatized for 5 days (A/J) before the experiments. On the day of the challenge, food and water were removed from the cages 5 h prior to oral gavage to prevent mechanical blockage of the *Listeria* inoculum by food in the stomach, which may cause the inoculum to aspirate into the lungs. The 6-h grown *L. monocytogenes* WT, $lap^-$, and ΔinlA strains, each resuspended in 200 μl of phosphate-buffered saline (PBS, pH 7.4) containing approximately $1\times10^8$ CFU for A/J mice and $1\times10^9$ CFU for C57BL/6 $MLCK^{+/+}$ or the $MLCK^{-/-}$ mice were administered orally to randomly selected mice using a stainless steel ball-end feeding needle (Popper). The control mice received only PBS. The food was returned 1 h pi, and the mice were sacrificed 24 h and 48 h pi using $CO_2$ asphyxiation. All animal procedure (IACUC Protocol no. 1201000595A002) was approved by the Purdue University Animal Care and Use Committee, who adheres to the recommendations of the Guide for the Care and Use of Laboratory Animals published by the National Institutes of Health.

Bacterial Strains and Growth Conditions.

*L. monocytogenes* F4244 (WT) serovar 4b, the isogenic lap-deficient insertion mutant KB208 ($lap^-$), the lap-complemented CKB208 ($lap^-$ $lap^+$), the ΔinlA in-frame deletion mutant (AKB301) and its complement (ΔinlA $inlA^+$; AKB302), the 10403s WT strain serovar 1/2a, and the in-frame deletion mutant strains, Δhly (DP-L2161) and the ΔinlB (DP-L4406) were used. 10403s and its derivative strains were kindly provided by Dr. Portnoy at UC-Berkeley. All of the *L. monocytogenes* strains were grown in Tryptic soy broth containing 0.6% yeast extract (TSBYE; BD Bioscience) at 37° C. with shaking for 12-16 h unless otherwise indicated. The $lap^-$ strain was grown in TSBYE containing erythromycin (Em; 5 μg/mL) at 42° C., the $lap^-$ $lap^+$ strain in TSBYE containing Em (5 μg/mL) and chloramphenicol (Cm; 5 μg/mL) at 37° C., and the ΔinlA $inlA^+$ strain in TSBYE containing Cm (5 μg/mL) at 37° C. *L. innocua* F4248 was grown in TSBYE at 37° C. for 12-16 h.

Cell Lines.

The human colon carcinoma Caco-2 cell line (ATTC # HTB37) from 25-35 passages were cultured in Dulbecco's Modified Eagle's medium (DMEM) (Thermo Fisher Scientific) supplemented with 4 mM L-glutamine, 1 mM sodium pyruvate and 100% fetal bovine serum (FBS; Atlanta Biologicals). Caco-2 cells presenting stable suppression of hsp60 mRNA and Caco-2 presenting a non-targeting control shRNA vector were previously developed using shRNA and cultured in DMEM supplemented with 4 mM L-glutamine, 1 mM sodium pyruvate, 10% FBS and 800 μg/mL Geneticin; G418. The NF-κB luciferase reporter cell line (Novus Biologicals) was cultured in DMEM supplemented with 4 mM L-glutamine, 1 mM sodium pyruvate, 10% FBS, 100 U/mL penicillin, 100 μg/mL streptomycin and 3 μg/mL puromycin. All cell-lines were maintained at 37° C. with 5% $CO_2$.

Enumeration of *L. monocytogenes* in Mouse Organs.

The organs were harvested aseptically and homogenized using a tissue homogenizer in 4.5 ml (spleen, MLN, kidney) or 9 ml (liver) of buffered—*Listeria* enrichment broth (BLEB) containing 0.1% Tween 20 and selective antimicrobial agents (Neogen). To enumerate *Listeria,* the samples were serially diluted in PBS and plated onto modified Oxford (MOX; Neogen) agar plates. In specific experiments, small sections of liver, spleen and ileal tissue samples (1 cm) were cut into two parts, with one part fixed overnight in 10% formalin for histopathology or immunofluorescence and the other stored in RNAlater (Thermo Fisher Scientific) for gene expression analysis. Urine excreted voluntarily during $CO_2$ asphyxiation was collected from the bag. Blood was collected using a 1 ml syringe with a 21G needle by cardiac puncture. To enumerate the *Listeria* in the blood, 50 μl of blood was diluted with 450 μl of BLEB immediately following collection and samples were serially diluted and plated as above.

To enumerate bacteria in the mucus, epithelial cell and the lamina propria fractions from the ileal tissue. Briefly, for separation of the mucus fraction, the ileum section (10 cm) was first flushed with sterile PBS, visible payer's patches were removed and cut longitudinally. The tissue sections were then washed three times by incubating for 2 min in a tube containing 3 ml of 6 mM N-acetylcysteine (Sigma-Aldrich), and then shaken vigorously before transferring to a fresh tube. The washes (9 ml) were pooled and centrifuged for 20 min at 12,000×g. The pellets were resuspended in 0.5 ml of PBS, vortexed and serial dilutions were plated on MOX agar plates. To enumerate bacteria in the epithelial fraction, the ileal tissue from above were cut into small pieces (1 cm each) with a scalpel and incubated at 37° C. with shaking in a tube containing 5 ml of RPMI (Invitrogen) supplemented with 5 mM EDTA, and 1 mM DTT for a total of 3 times. Each time, the tissues were transferred to fresh tubes containing 5 ml of RPMI supplemented with 5 mM EDTA, and 1 mM DTT. The combined three washes (15 ml) was centrifuged at low speed (1,200×g) to pellet the cells. The cell pellets and the supernatant fluids were processed separately to enumerate the intracellular and extracellular bacteria in the epithelial fraction. To enumerate intracellular bacteria, the pellet from either the epithelial fraction or the lamina propria fraction (extraction protocol mentioned below) was suspended in 5 ml of RPMI-5 containing 25 μg/mL gentamicin and the single cell suspension was incubated at 37° C. with 5% $CO_2$ for 30 min to kill any extracellular *L. monocytogenes*. The single cell suspension was then centrifuged at low speed (1,200×g) to pellet the cells and the pellets were washed twice in PBS. The pellets were then suspended in 0.5 ml PBS, vortexed to lyse the cells, serially diluted and plated on MOX agar plates. To quantify extracellular bacteria the supernatant from the washes of the epithelial cell fraction or the lamina propria fraction (extraction protocol mentioned below) was pooled and centrifuged at 12,000×g for 20 min. The pellets were then resuspended in 0.5 ml PBS, vortexed and plated on MOX agar plates. To enumerate bacteria in the lamina propria fraction, the DTT and EDTA from the intestinal pieces were removed by two successive washes in 25 ml sterile PBS. The tissue pieces were then incubated in a sterile tube of digestion solution containing 4 ml of RPMI supplemented with 5% FBS and 1 mg/mL type IV collagenase and 40 μg/mL DNAse I (both from Worthington) at 37° C. for 40 min with shaking. This step was repeated in a fresh tube containing the digestion solution until the tissue pieces were completely dissolved. The combined digestion solution was centrifuged at low speed (1,200×g) to pellet the cells. The pellet and the supernatant were processed as described above to enumerate the intracellular and extracellular bacteria in the lamina propria fraction.

Immunofluorescence Staining and Confocal Microscopy.

The mouse ileal-tissue sections were fixed with 10% formalin and embedded in paraffin. The tissues were sectioned (5 μm thick), deparaffinized, and rehydrated for antigen retrieval by immersing the slides in boiling sodium citrate buffer (10 mM, pH 6.0) for 10 min. The tissue sections were permeabilized and blocked with PBS containing 0.3% Triton X-100 (Sigma-Aldrich) and 3% normal goat serum (Cell signaling) and immunostained with specific antibodies by incubating overnight at 4° C. Following antibody incubation, slides were rinsed with PBS (3 cycles, 5 min), and were incubated with FITC or Alexa Fluor 555-conjugated secondary antibody for 2 h at room temperature followed by washing three times with PBS (3 cycles, 5 min). The nuclei were stained with DAPI (500 ng/mL; Cell signaling) and slides were mounted in ProLong antifade reagent (Cell Signaling). The p65 and P-p65 nuclear positive cells were counted and expressed as average nuclear positive cells per villus.

For antibody labeling in cells, Caco-2 cells, were grown to 40-50% confluence in four-chambered slides (Millipore). At the end of the treatment, the cells were fixed with 3.7% formaldehyde in PBS for 20 min and permeabilized and blocked with PBS containing 0.3% Triton X-100 and 3% BSA (Sigma-Aldrich) for 1 h at room temperature and then incubated with respective antibodies overnight at 4° C. Following antibody incubation, the cells were washed with PBS (3 cycles, 5 min) and incubated with FITC or Alexa Fluor 555-conjugated secondary antibody for 2 h at room temperature. The nuclei were stained with DAPI (500 ng/ml; Cell signaling) and slides were mounted in ProLong antifade reagent (Cell Signaling).

All images were acquired using a Nikon A1R MP Multiphoton (Nikon) Confocal fluorescence microscope using a 60× oil immersion objective equipped with the Nikon Elements software (Nikon) at the Purdue Bioscience Imaging Facility. The X-Z and Y-Z cross-sections were produced by orthogonal reconstructions from z-stack scanning at 0.15 μm intervals taken with 60× objective in 5 μm thick paraffin embedded tissue section. Three-dimensional reconstructions were performed using Nikon elements software (Nikon).

Analysis of In Vivo Intestinal Permeability.

The mice were orally gavaged with non-metabolizable 4 kDa FITC-labeled dextran (FD4; 15 mg/100 μl, Sigma-Aldrich) 4-5 h prior to sacrifice. Serum and urine (50 μl each), collected above, were mixed with an equal volume of PBS, and fluorescence was measured (Em: 485 nm; Ex: 520 nm; Spectramax, Molecular Devices) and the FD4 concentration was calculated using a standard curve generated by serially diluting FD4 in PBS. The serum and urine from the mice that were uninfected and not administered FD4 were used to determine the background levels.

Epithelial Permeability, Bacterial Translocation, Invasion and Pharmacological Inhibitors.

Caco-2 cells were grown as monolayers on Transwell inserts with 3.0 μm pores (Corning-Costar) for up to 14-21 days. TEER was measured to monitor the monolayer integrity (Millicells Voltmeter, Millipore). A TEER value of at least 200 Ω/cm$^2$ (±10) was used as the basal value to monitor the monolayer integrity. Bacterial cells were washed three times in PBS and resuspended in DMEM-FBS (10%) at a MOI of ~50 and were added to the apical side of the Transwell system, and after 2 h incubation period at 37° C. in 5% $CO_2$, the liquid was collected from the basal well, and then translocated bacteria were enumerated by plating (Burkholder and Bhunia, 2010). For analysis of FD4 flux, non-metabolizable 4 kDa FITC-labeled dextran (FD4; 5 mg/ml, Sigma-Aldrich) was added with bacteria (MOI, ~50) resuspended in DMEM-FBS (10%) and added to the apical side. After 2 h incubation at 37° C. in 5% $CO_2$, the liquid was collected from the basal well and fluorescence was measured (Em: 485 nm; Ex: 520 nm; Spectramax, Molecular Devices). For pharmacological inhibition treatments, PDTC (100 μM for 30 min pre-treatment; R&D Systems), Bay-11-7085 (10 μM for 30 min pre-treatment; Sigma-Aldrich), ML-9 (20 μM for 30 min pre-treatment; Sigma-Aldrich), PIK (150 μM, 30 min-pre-treatment and kept during 2-h infection) (Zolotarevsky et al., 2002), and Cytochalasin D (1 μg/mL for 1 h; Sigma-Aldrich) were used separately.

For re-association of externally added LAP to the lap$^-$ mutant, bacteria were harvested from 1 ml of overnight grown culture, and the pellet was washed three times in PBS before the addition of 1 or 2 μg/mL of purified LAP. The mixture was incubated for 30 min at 30° C. with continuous shaking and then pelleted, washed five times in the PBS, resuspended in DMEM, and used in the aforementioned translocation assay.

To determine the effect of LAP on Caco-2 permeability at specified time points (0, 24, 48 and 72 h) following incubation with recombinant purified LAP, 100 μl of FD4 (1 mg/mL in DMEM) was added to the apical side and the fluorescence readings (Em: 485 nm; Ex: 520 nm; Spectramax, Molecular Devices) for the basal medium (100 μl) were measured. Human TNF-α (10 ng/mL, R&D Systems) was added to both apical and basal sides and used as a positive control.

For bacterial invasion analysis, monolayers were washed with PBS after 1 h of infection (MOI, ~50) and incubated with DMEM-FBS (10%) containing gentamicin (50 μg/mL) for 1 h. Caco-2 cells were lysed with 0.1% Triton X, and the internalized bacteria were enumerated by plating.

Caco-2 cell viability assay. To determine Caco-2 viability, cell culture supernatants from Caco-2 cells infected with WT, lap$^-$, lap$^-$lap$^+$, ΔinlA and ΔinlA inlA$^+$ strains (MOI 50, 2 h) grown on Transwell inserts or treated with the purified recombinant LAP for 24 or 48 h were assayed for lactate dehydrogenase release (Thermo Fisher Scientific). Two controls were included for calculation of percent cytotoxicity (LDH release). Low control consisted of supernatant from untreated Caco-2 cells with no exposure to bacteria. High control was from cells treated with 0.1% Triton X-100 for one minute.

Recombinant Protein Purification.

Recombinant proteins (LAP and InlB) containing endogenous His, S and Trx tags derived from the pET-32a/pET28 cloning vector (Novagen) from *E. coli* BL21 or ClearColi (Lucigen) were purified using a Ni-affinity column. In ClearColi, LPS lacks secondary acyl chain thus eliminating endotoxicity. Briefly, for LAP purification, *E. coli* BL21 or ClearColi were each grown in 1 L LB broth (BD) with ampicillin (50 μg/mL) for 3 h at 37° C. For InlB purification, *E. coli* pET28b-1 was grown in 1 L LB containing 30 μg/mL of kanamycin at 37° C. for 3 h, and IPTG (1 mM) induced at 20° C. for 12 h. After sonication (total 7 min, with cycles of 30 sec sonication and 15 sec pulse; Branson Sonifier), the supernatants were purified by Ni-column. The Toxin-Eraser Endotoxin Removal Kit (Genscript) was used to remove LPS and the Toxin-Sensor Chromogenic LAL Endotoxin Assay Kit (Genscript) was used to detect any residual LPS in the samples. Protein concentrations were measured by Bradford assay, and the purity was monitored by SDS-PAGE (12.5%-acrylamide). Purified recombinant InlA was provided by Marcelo Mendonça (University of Pelotas, Brazil).

Cytokine Array and ELISA.

A semi-quantitative membrane-based RayBio Human Inflammation Antibody Array kit (Ray Biotech) was used to analyze a panel of 40 inflammatory mediators in Caco-2 cell supernatant infected either with the WT or $lap^-$ strain (MOI, ~50) at 37° C. for 1 h. After killing the extracellular bacteria by gentamicin (50 μg/mL), the Caco-2 cells were incubated for an additional 7 h at 37° C. Recombinant LAP (1 μg/mL) from ClearColi was incubated for 8 h with Caco-2 cells. After immunoblotting, the reaction intensity was quantified using NIH ImageJ software. The data were normalized and expressed as the mean fold changes as a ratio of $lap^-$/WT±SEM. For the ELISA, Caco-2 cell supernatants were centrifuged (2,000 rpm at 4° C. for 10 min) following treatment as above, and the quantification of TNF-α and IL-6 in was performed using human TNF-α and IL-6 ELISA kits (Ray Biotech) as per manufacturer's instruction. The quantification of TNF-α and IL-6 protein levels was performed in the ileal tissue lysates from mice using mouse TNF-α and IL-6 ELISA kits (Ray Biotech) as per manufacturer's instruction.

RNA Preparation and qRT-PCR.

Total RNA was isolated from the mouse ileal tissues using TRIzol reagent (Thermo Fisher Scientific) according to the manufacturer's instructions and treated with the TURBO DNA-free Kit (Thermo Fisher Scientific) to remove residual genomic DNA. The transcript levels were determined using Superscript III Platinum SYBR Green One-Step qRT-PCR kit (Thermo Fisher Scientific). Primers were obtained from IDT and their recommended thermal cycling conditions were used. GAPDH was used as a housekeeping gene control for the ileal tissues. The $2^{-\Delta\Delta Ct}$ method was used to calculate the relative changes in gene expression. The relative expression in each figure refers to the induction levels of the gene of interest relative to GAPDH, and these levels were then compared with that of an untreated control calibrator sample.

Histopathology.

Thin tissue sections from above were stained with hematoxylin and eosin, and a board-certified veterinary pathologist microscopically examined the slides and the interpretations were based on standard histopathological morphologies. The pathologist, who was blinded to the bacterial strain, compared the ileal sections to the controls. To determine the extent of the mouse ileal lesions, a semi-quantitative method was used that included the amount of inflammatory infiltrate and percentage of goblet cells that composed the villous epithelium. Similarly, the mouse livers and spleens were evaluated based on the extent of parenchymal necrosis and infiltrative inflammation. The histomorphological scale for the ileum was graded as follows: inflammation in the lamina propria of the mucosa at 3=marked amounts (sheets of granulocytes expanding the width of the villous tip), at 2=moderate amounts (sheets of granulocytes at the base of the villous), at 1=mild amounts (multifocal scattering), at 0-=none observed. Goblet cell counts were graded as follows: 3=50% or greater, 2=25-50%, 1=11-25%, 0 to <10%. Higher goblet cell scores correspond to a more likely indication of intestinal infection. The necrosis scores for the livers and spleens were as follows: 1 to 53=microscopic foci, 2 to ≥3=microscopic foci, and 3=massive necrosis. The inflammation scores of the livers and spleens were as follows: 1=mild inflammation, 2=moderate to marked inflammation associated with the foci of necrosis.

Immunoblotting.

To extract the proteins from Caco-2 cells, cells were seeded in 6-well plates for 14-21 days. Following treatment, the cells were washed, scraped from the bottom of 6-well plates, suspended in PBS, and pelleted by centrifugation. Total protein from Caco-2 cells was extracted using the M-PER Extraction Kit (Thermo Fisher Scientific). Detergent-insoluble (membrane) and detergent-soluble (cytosolic) proteins were isolated using a Mem-Per Eukaryotic Protein Extraction Kit (Thermo Fisher Scientific) while the cytosolic and nuclear proteins were extracted using NE-PER Extraction Reagent (Thermo Fisher Scientific). To extract proteins from ileal epithelial cells, the epithelial cell fraction from ileal tissues were isolated as described above and the detergent-insoluble and the detergent-soluble proteins were isolated using a Mem-Per Eukaryotic Protein Extraction Kit.

To extract total protein from intact bacterial cells, sample solvent buffer and sonication (3 cycles of 20 min each) were used. To isolate the cell wall-associated proteins bacterial pellets were resuspended in 0.5 ml protein extraction buffer (0.5% SDS, 10 mM Tris at pH 6.9), and incubated at 37° C. for 30 min with agitation. The samples were centrifuged (14,000×g, 10 min, 4° C.), and the supernatants (containing cell wall-associated proteins) were retained. Halt proteases and phosphatase inhibitors (Thermo Fisher Scientific) were used during all of the protein extraction procedures. The protein concentrations were determined by BCA assay (Thermo Fisher Scientific), and separated on SDS-PAGE gels (10-12.5% polyacrylamide) and electro-transferred to polyvinylidene difluoride (PVDF) membrane (Millipore). The membranes were then blocked in 5% nonfat dry milk (NFDM) in 0.1 M Tris-buffered saline, pH 7.5 (TBS) containing 0.1% Tween 20 (TBST) for at least 1 h. All of the primary antibodies were diluted in 5% bovine serum albumin (BSA) or 5% NFDM in TBST and incubated overnight. Secondary antibodies (1:2000 in 5% NFDM in TBST) incubated for 1 h at 37° C., and a chemiluminescence method was performed using LumiGLO reagent (Cell Signaling). The membranes were exposed to X-ray films or visualized using the Chemi-Doc XRS system (Bio-Rad). To immunoprobe the same membrane with another antibody, the originally bound antibodies from the membranes were removed by incubating the membranes in Restore Western Blot Stripping Buffer (Thermo Fisher Scientific) according to the manufacturer's protocol. To compare the reaction intensities, the average band densities were determined using Quantity One software (Bio-Rad). Densitometry reports represent the mean±SEM after normalization to the loading control and is presented as % change of protein with the average for untreated cells (control) set at 100%. Immunoblots and densitometric reports are representative of 2-3 independent experiments.

Luciferase Assay.

The NF-κB Luciferase reporter RAW 264.7 cell line (Novus Biologicals), which expresses an optimized *Renilla* luciferase reporter gene (RenSP) under the transcriptional control of an NF-κB response element, was used. The cells were seeded ($1\times10^5$ cells/well) into 96-well luminometer-compatible plates for 16 h and then treated with analytes for 6 h. Media from each well were aspirated, and then 100 μL of ice-cold PBS was added to each well. The plates were then frozen solid at −80° C. overnight to completely lyse the cells, thawed back to room temperature, and luciferase assays were performed using the LightSwitch Luciferase assay kit (Novus Biologicals). Luminescence was measured as the relative luminescence units (RLU) using Spectramax (Spectramax, Molecular Devices) and reported as the relative fold change compared with that of the control cells that were treated with media alone. Recombinant human or mouse TNF-α (R&D Systems) and polymyxin B, LPS (*E. coli* Serotype R515, Re, TLR grade), and proteinase K (each from Sigma-Aldrich) were used.

Immunoprecipitation.

Caco-2 cells were treated with or without purified LAP (1 μg/mL) for 30 min, rinsed with cold PBS, and lysed in Nondiet P-40 (NP-40) lysis buffer (20 mM Tris HCl, pH 8,137 mM NaCl, 1% NP-40, 2 mM EDTA). The cell lysates were pre-cleared with 10 μl protein G agarose beads (Micro-Protein Technologies) for 1 h and the lysates were incubated with 2 μg of anti-IKKβ, 2 μg of anti-Hsp60, rabbit serum or normal mouse serum overnight at 4° C. The lysates were further mixed with 20 μL protein G agarose beads for 3 h at 4° C. The beads were washed five times with 1 ml NP-40 lysis buffer. The protein precipitates were analyzed by immunoblotting, and the complexes were visualized by chemiluminescence assay.

LAP-Drug Crosslinking:

For crosslinking of LAP with a drug, N,N'-carbonyl diimidazole (CDI) chemistry is used to create a linkage between amine group of LAP and hydroxyl group of the drug (Patel, S. K., et al., Journal of Drug Targeting, 2012, 20(10), 841-849). Paclitaxel is an anticancer drug, and often used as a model drug for various efficacy testing. Ring of a paclitaxel is functionalized with different functional groups including a hydroxyl group (OH) at C-1 position. CDI activates the hydroxyl group by creating either a zero-length amide bond or one-carbon-length N-alkyl carbamate linkages between the LAP and paclitaxel. Briefly, paclitaxel (1.0 mg) and CDI (1.5 mg) are dissolved in dimethylformamide and stirred at 30° C. for 3 h. Subsequently, purified LAP or its peptide derivatives dissolved in phosphate-buffered saline (PBS) is added to the paclitaxel solution, and is stirred at 30° C. overnight. The mixture is dialyzed against distilled water at 4° C. for 24 h and the resulting LAP-drug linker can be used for biological testing in a cell culture model or animal model (Sakamoto, S., et al., Talanta, 2017, 168, 67-72.)

Conjugation of LAP with Protein/Peptide Drugs

Chemical Modification.

Chemical approach is used to cross-link LAP or it fragments with a protein/peptide drug. Briefly, EDC/NHS [1-ethyl-3-(3-dimethylaminopropyl) carbodiimide hydrochloride/N-hydroxysuccinimide] cross-linking is performed by mixing 2 M EDC with 20 mM NHS in MES (2-ethanesulfonic acid)-buffered saline (50 mM MES, 150 mM NaCl), pH 6.0. The cross-linker mix is then added to an equal volume of the mixture of LAP and a peptide drug for 30 min, before the reaction is quenched with an equal volume of 1 M glycine (pH 7.4) for 10 min. The resulting protein conjugates can be verified by SDS-polyacrylamide gel electrophoresis (SDSPAGE) analysis.

Molecular Cloning.

Briefly, co-expression of LAP and a peptide drug is achieved by recombinant DNA technology (Ikeno, S., et al., *PloS One,* 2013, 8(12), e82824). The gene for the peptide drug and LAP will be sub cloned in a plasmid expression vector containing two different cloning sites and introduced in *E. coli.* The construction of the expression vector is verified by DNA sequencing. After induction, the co-expressed recombinant protein is analyzed by SDS-PAGE and Western blotting.

List of related protein and peptide sequences disclosed in this invention:

```
Listeria Adhesion Protein (LAP) sequences of alcohol acetaldehyde
dehydrogenase of Listeria monocytogenes (SEQ ID NO: 1)
  1   MAIKENAAQE VLEVQKVIDR LADNGQKALK AFESYNQEQV DNIVHAMALA GLDQHMPLAK

 61   LAVEETGRGL YEDKCIKNIF ATEYIWNNIK NNKTVGVINE DVQTGVIEIA EPVGVVAGVT

121   PVTNPTSTTL FKAIIAIKTR NPIIFAFHPS AQRCSSAAAK VVYDAAIAAG APEHCIQWVE

181   KPSLEATKQL MNHDKVALVL ATGGAGMVKS AYSTGKPALG VGPGNVPAYI DKTAKIKRSV

241   NDIILSKSFD QGMICASEQA VIVDKEVAKE VKAEMEANKC YFVKGAEFKK LESYVINPEK

301   GTLNPDVVGK SPAWIANQAG FKVPEDTKIL VAEIKGVGDK YPLSHEKLSP VLAFIEAANQ

361   AFAFDRCEEM LVYGGLGHSA VIHSTDKEVQ KAFGIRMKAC RIIVNAPSAQ GGIGDIYNGF

421   IPSLTLGCGS YGKNSVSQNV SATNLLNVKR IADRRNNMQW FKLPPKIFFE KYSTQYLQKM

481   EGVERVFIVT DPGMGSFKYV DVVIEHLKKR GNDVAYQVFA DVEPDPSDVT VYKGAELMKD

541   FKPDTIIALG GGSAMDAAKG MWLFYEHPEA SFFGLKQKFL DIRKRTFKYP KLGGKAKFVA

601   IPTTSGTGSE VTPFAVITDK ENNIKYPLAD YELTPDVAIV DAQYVTTVPA HITADTGMDV

661   LTHAIESYVS VMASDYTRGL SIRAIELVFE NLRESVLTGD PDAREKMHNA SALAGMAFAN

721   AFLGINHSLA HKIGPEFHIP HGRANAILMP HVIRYNALKP KKHALFPRYE SFRADEDYAR

781   ISRIIGFPAA TTEEGVKSLV DEIIKLGKDV GIDMSLKGQN VAKKDLDAVV DTLADRAFMD

841   QCTTANPKQP LVSELKEIYL EAYKGV
```

-continued

LAP fragment N2 ($Gly_{224}$-$Gly_{411}$) (SEQ ID NO: 2)
GNVPAYI DKTAKIKRSV NDIILSKSFD QGMICASEQA VIVDKEVAKE VKAEMEANKC YFVKGAEFKK

LESYVINPEK GTLNPDVVGK SPAWIANQAG FKVPEDTKIL VAEIKGVGDK YPLSHEKLSP VLAFIEAANQ

AEAFDRCEEM LVYGGLGHSA VIHSTDKEVQ KAFGIRMKAC RIIVNAPSAQ G

N2 domain fused with histidine tag for ease of production and separation (SEQ ID NO: 3):
HHHHHHGNVPAYI DKTAKIKRSV

NDIILSKSFD QGMICASEQA VIVDKEVAKE VKAEMEANKC YFVKGAEFKK LESYVINPEK

GTLNPDVVGK SPAWIANQAG FKVPEDTKIL VAEIKGVGDK YPLSHEKLSP VLAFIEAANQ

AEAFDRCEEM LVYGGLGHSA VIHSTDKEVQ KAFGIRMKAC RIIVNAPSAQ GHHHHHH

LAP fragment N1 ($Met_1$-$Pro_{223}$): (SEQ ID NO: 4)
MAIKENAAQE VLEVQKVIDR LADNGQKALK AFESYNQEQV DNIVHAMALA GLDQHMPLAK

LAVEETGRGL YEDKCIKNIF ATEYIWNNIK NNKTVGVINE DVQTGVIEIA EPVGVVAGVT

PVTNPTSTTL FKAIIAIKTR NPIIFAFHPS AQRCSSAAAK VVYDAAIAAG APEHCIQWVE

KPSLEATKQL MNHDKVALVL ATGGAGMVKS AYSTGKPALG VGP

LAP fragment C1 ($Gly_{412}$-$Val_{648}$) (SEQ ID NO: 5)
GGIGDIYNGF IPSLTLGCGS YGKNSVSQNV SATNLLNVKR IADRRNNMQW FKLPPKIFFE

KYSTQYLQKM EGVERVFIVT DPGMGSFKYV DVVIEHLKKR GNDVAYQVFA DVEPDPSDVT

VYKGAELMKD FKPDTIIALG GGSAMDAAKG MWLFYEHPEA SFFGLKQKFL DIRKRTFKYP

KLGGKAKFVA IPTTSGTGSE VTPFAVITDK ENNIKYPLAD YELTPDVAIV DAQYVTTV

LAP fragment C2 ($Pro_{649}$-$Val_{866}$) (SEQ ID NO: 6)
PA HITADTGMDV LTHAIESYVS VMASDYTRGL SIRAIELVFE NLRESVLTGD PDAREKMHNA

SALAGMAFAN AFLGINHSLA HKIGPEFHIP HGRANAILMP HVIRYNALKP KKHALFPRYE

SFRADEDYAR ISRIIGFPAA TTEEGVKSLV DEIIKLGKDV GIDMSLKGQN VAKKDLDAVV

DTLADRAFMD QCTTANPKQP LVSELKEIYL EAYKGV

For the convenience of production and isolation of targeted polypeptides, histidine tags are attached to the primary sequence of targeted polypeptides during recombination expression. Here are the histidine tagged sequences of LAP domains:

LAP fragment N1 domain(SEQ ID NO: 7):
HHHHHHMAIKENAAQE VLEVQKVIDR LADNGQKALK AFESYNQEQV

DNIVHAMALA GLDQHMPLAK LAVEETGRGL YEDKCIKNIF

ATEYIWNNIK NNKTVGVINE DVQTGVIEIA EPVGVVAGVT

PVTNPTSTTL FKAIIAIKTR NPIIFAFHPS AQRCSSAAAK

VVYDAAIAAG APEHCIQWVE KPSLEATKQL MNHDKVALVL

ATGGAGMVKS AYSTGKPALG VGPHHHHHH

C1 domain(SEQ ID NO: 8):
HHHHHH GGIGDIYNGF IPSLTLGCGS YGKNSVSQNV SATNLLNVKR

IADRRNNMQW FKLPPKIFFE KYSTQYLQKM EGVERVFIVT

DPGMGSFKYV DVVIEHLKKR GNDVAYQVFA DVEPDPSDVT

VYKGAELMKD FKPDTIIALG GGSAMDAAKG MWLFYEHPEA

SFFGLKQKFL DIRKRTFKYP KLGGKAKFVA IPTTSGTGSE

VTPFAVITDK ENNIKYPLAD YELTPDVAIV DAQYVTTV HHHHHH

C2 domain (SEQ ID NO: 9):

-continued

HHHHHHPA HITADTGMDV LTHAIESYVS VMASDYTRGL

SIRAIELVFE NLRESVLTGD PDAREKMHNA SALAGMAFAN

AFLGINHSLA HKIGPEFHIP HGRANAILMP HVIRYNALKP

KKHALFPRYE SFRADEDYAR ISRIIGFPAA TTEEGVKSLV

DEIIKLGKDV GIDMSLKGQN VAKKDLDAVV DTLADRAFMD

QCTTANPKQP LVSELKEIYL EAYKGV HHHHHH

Histidine-tagged LAP Sequence (SEQ ID NO: 10):
HHHHHH MAIKENAAQEVLEVQKVIDRLADNGQKALKAFESYNQEQVDNI

VHAMALAGLDQHMPLAKLAVEETGRGLYEDKCIKNIFATEYIWNNIKNNK

TVGVINEDVQTGVIEIAEPVGVVAGVTPVTNPTSTTLFKAIIAIKTRNPI

IFAFHPSAQRCSSAAAKVVYDAAIAAGAPEHCIQWVEKPSLEATKQLMNH

DKVALVLATGGAGMVKSAYSTGKPALGVGPGNVPAYIDKTAKIKRSVNDI

ILSKSFDQGMICASEQAVIVDKEVAKEVKAEMEANKCYFVKGAEFKKLES

YVINPEKGTLNPDVVGKSPAWIANQAGFKVPEDTKILVAEIKGVGDKYPL

SHEKLSPVLAFIEAANQAEAFDRCEEMLVYGGLGHSAVIHSTDKEVQKAF

GIRMKACRIIVNAPSAQGGIGDIYNGFIPSLTLGCGSYGKNSVSQNVSAT

NLLNVKRIADRRNNMQWFKLPPKIFFEKYSTQYLQKMEGVERVFIVTDPG

MGSFKYVDVVIEHLKKRGNDVAYQVFADVEPDPSDVTVYKGAELMKDFKP

DTIIALGGGSAMDAAKGMWLFYEHPEASFFGLKQKFLDIRKRTFKYPKLG
GKAKFVAIPTTSGTGSEVTPFAVITDKENNIKYPLADYELTPDVAIVDAQ
YVTTVPAHITADTGMDVLTHAIESYVSVMASDYTRGLSIRAIELVFENLR
ESVLTGDPDAREKMHNASALAGMAFANAFLGINHSLAHKIGPEFHIPHGR
ANAILMPHVIRYNALKPKKHALFPRYESFRADEDYARISRIIGFPAATTE
EGVKSLVDEIIKLGKDVGIDMSLKGQNVAKKDLDAVVDTLADRAFMDQCT
TANPKQPLVSELKEIYLEAYKGV HHHHHH

Other closely related LAP sequences of alcohol acetaldehyde dehydrogenase:

```
Listeria ivanovii (SEQ ID NO: 11):
  1 MAIKENAAQE VLEVQKVIDR LADNGQKALK AFENYDQEQV DNIVHAMALA GLDQHMPLAK
 61 LAVEETGRGL YEDKCIKNIF ATEYIWNNIK NNKTVGVTNE DVQTGVIEIA EPVGVVAGVT
121 PVTNPTSTTL FKAIIAIKTR NPIIFAFHPS AQGCSSAAAK VVYDAAIAAG APEHCIQWVE
181 KPSLEATKQL MNHEKVALVL ATGGAGMVKS AYSTGKPALG VGPGNVPAYI DKTAXIKRSV
241 SDIILSKSFD QGMICASEQA VIVDKEVAKE VKAEMEANKC YFVKGAEFKK LESYVINPEK
301 GTLNPDVVGK SPAWIANQAG FKIPEDTKIL VAEIKGVGDK YPLSHEKLSP VLAFIEAANQ
361 TEAFDRCEEM LVYGGLGHSA VIHSTDKEVQ KAFGIRMKAC RIIVNAPSAQ GGIGDIYNGF
421 IPSLTLGCGS YGKNSVSQNV SATNLLNVKR IADRRNNMQW FKLPPKIFFE KYSTQYLQKM
481 EGVERVFIVT DPGMVQFKYV DVVIEHLKKR GNDVSYQVFA DVEPDPSDVT VYKGAELMKD
541 FKPDTIIALG GGSAMDAAKG MWLFYEHPEA SFFGLKQKFL DIRKRTFKYP KLGGKAKFVA
601 IPTTSGTGSE VTPFAVITDK ENNIKYPLAD YELTPDVAIV DAQYVTTVPA HITADTGMDV
661 LTHAIESYVS VMASDYTRGV SIRAIELVFE NLRDSVLKGD PDAREKMHNA SALAGMAFAN
721 AFLGINHSLA HKIGPEFHIP HGRANAILMP HVIRYNALKP RKHALFPRYE SFRADEDYAR
781 ISRIIGFPAA TTEEGVKSLV DEIIKLGKDV GIDMSLKGQN VAKKDLDAVV DTLADRAFMD
841 QCTTANPKQP LVSELKEIYL EAYKGV

Listeria seeligeri (SEQ ID NO: 12):
  1 MAIKENAAQE VLEVQKVIDR LADNGQKALK AFENYDQEQV DNIVHAMALA GLDQHMPLAK
 61 LAVEETGRGL YEDKCIKNIF ATEYIWNNIK NNKTVGVTNE DVQTGVIEIA EPVGVVAGVT
121 PVTNPTSTTL FKAIIAIKTR NPIIFAFHPS AQGCSSAAAK VVYDAAIAAG APEHCIQWVE
181 KPSLEATKQL MNHEKVALVL ATGGAGMVKS AYSTGKPALG VGPGNVPAYI DKTAKIKRSV
241 NDIILSKSFD QGMICASEQA VIVDKEVAKE VKAEMEANNC YFVKGAEFKK LESYVINPEK
301 GTLNPDVVGK SPAWIANQAG FKVPEDTKIL VAEIKGVGDK YPLSHEKLSP VLAFIEAANQ
361 AEAFDRCEEM LVYGGLGHSA VIHSTDKEVQ KAFGIRMKAC RIIVNAPSAQ GGIGDIYNGF
421 IPSLTLGCGS YGKNSVSQNV SATNLLNVKR IADRRNNMQW FKLPPKIFFE KYSTQYLQKM
481 EGVERVFIVT DPGMVQFKYV DVVIEHLXKR GNDVSYQVFA DVEPDPSDVT VYKGAELMKD
541 FKPDTIIALG GGSAMDAAKG MWLFYEHPEA SFFGLKQKFL DIRKRTFKYP KLGGKAKFVA
601 IPTTSGTGSE VTPFAVITDK ENNIKYPLAD YELTPDVAXV DAQYVTTVPA HITADTGMDV
661 LTHAIESYVS VMAGDYTRGL SIRAIELVFE NLRDSVLKGD PDAREKMHNA SALAGMAFAN
721 AFLGINHSLA HKIGPEFHIP HGRANAILMP HVIRYNALKP KKHALFPRYE SFRADEDYAR
781 ISRIIGFPAA TTEEGVKSLV DEIIKLGKDV GIDMSLKGQN VDKKDLDAVV DTLADRAFMD
841 QCTTANPKQP LVSELKEIYL EAYKGV

Listeria welshimeri (SEQ ID NO: 13):
  1 MAIKENAAQE VLEVQKVINR LADNGQQALK AFENYDQEQV DNIVHAMALA GLDQHMPLAK
 61 LAVEETGRGL YEDKCIKNIF ATEYIWNNIK NNKTVGVIHE DVQTGVIEIA EPVGVVAGVT
121 PVTNPTSTTL FKAIIAIKTR NPIIFAFHPS AQRCSAAAAK VVYDAAVAAG APEHCIQWVE
```

-continued

181KPSLEATKQL MNHDKVALVL ATGGAGMVKS AYSTGKPALG VGPGNVPAYI DKTAKIKRSV

241NDIILSKSFG QGMICASEQA VIVDKEVAKE VKAEMEANKC YFVKGAEFKK LESYVINPEK

301GTLNPDVVGK SPAWIANQAG FKVPEDTKIL VAEIKGVGDK YPLSHEKLSP VLAFIEAANQ

361AEAFDRCEEM LVYGGLGHSA VIHSTDKEVQ KAFGIRMKAC RIIVNAPSAQ SGIGDIYNGF

421IPSLTLGCGS YGKNSVSQNV SATNLLNVKR IADRRNNMQW FKLPPKIFFE KYSTQYLQKM

481EGVERVFIVT DPGMVQFKYV DVVIEHLKKR GNDVAYQVFA DVEPDPSDVT VYKGAELMKD

541FKPDTIIALG GGSAMDAAKG MWLFYEHPEA SFFGLKQKFL DIRKRTFKYP KLGGKAKFVA

601IPTTSGTGSE VTPFAVITDK ENNIKYPLAD YELTPDVAIV DAQYVTTVPA HITADTGMDV

661LTHAIESYVS VMASDYTRGL SIRAIELVFE NLRESVLTGD PDAREKMHNA SALAGMAFAN

721AFLGINHSLA HKIGPEFHIP HGRANAILMP HVIRYNALKP KKHALFPRYE SFRADEDYAR

781ISRIIGLPAA TTEEGVKSLV DAIIKLGKDV GIDMSLKGQN VAKKDLDAVV DTLADRAFMD

841QCTTANPKQP LVSELKEIYL EAYKGV

*Listeria innocua* (SEQ ID NO: 14):

1MAIKENAAQE VLEVQKVIDR LADNGQKALK AFESYNQEQV DNIVHAMALA GLDQHMPLAK

61LAVEETGRGL YEDKCIKNIF ATEYIWNNIK NNKTVGVINE DTQTGVIEIA EPVGVVAGVT

121PVTNPTSTTL FKAIIAIKTR NPIIFAFHPS AQRCSSEAAK VVYDAAVAAG APEHCIQWVE

181KPSLEATKQL MNHDKVALVL ATGGAGMVKS AYSTGEPALG VGPGNVPAYI DKTAKIKRSV

241NDIILSKSFD QGMICASEQA VIVDKEVAKE VKAEMEANKC YFVKGAEFKK LESYVINPEK

301GTLNPDVVGK SPAWIANQAG FKVPEDTKIL VAEIKGVGDK YPLSHEKLSP VLAFIEAATQ

361AEAFDRCEEM LVYGGLGESA VIHSTDKEVQ KAFGIRMKAC RIIVNAPSAQ GGIGDIYNGF

421IPSLTLGCGS YGKNSVSQNV SATNLLNVKR IADRRNNMQW FKLPPKIFFE KYSTQYLQKM

481EGVERVFIVT DPGMVQFKYV DVVIEHLKKR GNDVAYQVFA DVEPDPSDVT VYKGAELMKD

541FKPDTIIALG GGSAMDAAKG MWLFYEHPEA SFFGLKQKFL DIRKRTFKYP KLGGKAKFVA

601IPTTSGTGSE VTPFAVITDK ENNIKYPLAD YELTPDVAIV DAQYVTTVPA HITADTGMDV

661LTHAIESYVS VMASDYTRGL SIRAIELVFE NLRESVLTGD PDAREKMHNA SALAGMAFAN

721AFLGINHSLA HKIGPEFHIP HGRANAILMP HVIRYNALKP KKHALFPRYE SFRADEDYAR

781ISRIIGFRAA TTEEGVKSLV DEIIKLGKDV GIDMSLKGQN VAKKDLDAVV DTLADRAFMD

841QCTTANPKQP LVSELKEIYL EAYKGV

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A method for enhancing delivery efficiency of a drug to systemic circulation comprising incorporating a polypeptide selected from SEQ ID NO: 1, SEQ ID NO:2, and a polypeptide comprising 90% or more sequence identity to SEQ ID NO:1 or SEQ ID NO:2, by physical mixing or covalent attachment, to the drug to be delivered.

2. The method according to claim 1, wherein the polypeptide is SEQ ID NO:2 or a polypeptide having 90% or more sequence identity to SEQ ID NO: 2.

3. The method according to claim 1, wherein the polypeptide of SEQ ID NO: 1 or 90% or more sequence identity to SEQ ID NO: 1 is covalently linked to the drug to be delivered.

4. The method according to claim 1, wherein the polypeptide of SEQ ID NO: 2 or 90% or more sequence identity to SEQ ID NO: 2 is co-formulated together with the drug to be delivered.

5. The method according to claim 1, wherein the route of drug delivery is via an epithelial surface.

6. The method according to claim 5, wherein the route of drug delivery is per oral, via submucosal, vaginal or rectal route.

7. A pharmaceutical composition for enhancing delivery efficiency of a drug to systemic circulation comprising one or more polypeptides of claim 1, or a pharmaceutically acceptable salt thereof, in combination with one or more drugs, together with one or more diluents, excipients or carriers.

8. The pharmaceutical composition of claim 7, wherein the polypeptide comprises SEQ ID NO: 1 or 90% or more sequence identity to SEQ ID NO: 1.

9. The pharmaceutical composition of claim 7, wherein the polypeptide comprises SEQ ID NO: 2 or 90% or more sequence identity to SEQ ID NO: 2.

10. A method for enhancing delivery efficiency of a drug to systemic circulation comprising incorporating a polypeptide comprising SEQ ID NO: 2 or 90% or more identity to SEQ ID NO: 2, by physical mixing or covalent attachment, to the drug to be delivered.

11. The method according to claim 10, wherein the polypeptide of SEQ ID NO: 2 or 90% or more identity to SEQ ID NO: 2 is covalently linked to the drug to be delivered.

12. The method according to claim 10, wherein the polypeptide of SEQ ID NO: 2 or 90% or more identity to SEQ ID NO: 2 is co-formulated together with the drug to be delivered.

13. The method according to claim 10, wherein the route of drug delivery is via an epithelial surface.

14. The method according to claim 13, wherein the route of drug delivery is per oral, via submucosal, vaginal or rectal route.

15. A pharmaceutical composition for enhancing delivery efficiency of a drug to systemic circulation comprising one or more polypeptides comprising SEQ ID NO: 2, 90% or more identity to SEQ ID NO: 2 or a pharmaceutically acceptable salt thereof, in combination with one or more therapeutically effective compounds drugs, together with one or more diluents, excipients or carriers.

16. A method for enhancing delivery efficiency of a drug to systemic circulation comprising incorporating a polypeptide comprising SEQ ID NO: 3 or 90% or more identity to SEQ ID NO: 3, by physical mixing or covalent attachment, to the drug to be delivered.

17. The method according to claim 16, wherein the polypeptide of SEQ ID NO: 3 or 90% or more identity to SEQ ID NO: 3 is covalently linked to the drug to be delivered.

18. The method according to claim 16, wherein the polypeptide of SEQ ID NO: 3 or 90% or more identity to SEQ ID NO: 3 is co-formulated together with the drug to be delivered.

19. The method according to claim 10, wherein the route of drug delivery is via an epithelial surface.

20. The method according to claim 13, wherein the route of drug delivery is per oral, via submucosal, vaginal or rectal route.

* * * * *